United States Patent
Phares

(10) Patent No.: US 12,098,116 B2
(45) Date of Patent: Sep. 24, 2024

(54) CRYSTALLINE PROSTACYCLIN (IP) RECEPTOR AGONIST AND USES THEREOF

(71) Applicant: United Therapeutics Corporation, Silver Spring, MD (US)

(72) Inventor: Kenneth Phares, Hillsborough, NC (US)

(73) Assignee: UNITED THERAPEUTICS CORPORATION, Silver Spring, MD (US)

( * ) Notice: Subject to any disclaimer, the term of this patent is extended or adjusted under 35 U.S.C. 154(b) by 0 days.

(21) Appl. No.: 18/169,016

(22) Filed: Feb. 14, 2023

(65) Prior Publication Data

US 2023/0406815 A1  Dec. 21, 2023

Related U.S. Application Data

(60) Provisional application No. 63/310,469, filed on Feb. 15, 2022.

(51) Int. Cl.
  *C07C 271/28* (2006.01)

(52) U.S. Cl.
  CPC ........ *C07C 271/28* (2013.01); *C07B 2200/13* (2013.01)

(58) Field of Classification Search
  CPC .................. C07C 271/28; C07B 2200/13
  See application file for complete search history.

(56) References Cited

U.S. PATENT DOCUMENTS

| | | |
|---|---|---|
| 5,849,919 A | 12/1998 | Hamanaka et al. |
| 6,746,729 B1 | 6/2004 | Cherkaoui et al. |
| 7,115,746 B2 | 10/2006 | Snoonian et al. |
| 7,202,253 B2 | 4/2007 | Lloyd et al. |
| 7,226,550 B2 | 6/2007 | Hou et al. |
| 8,895,776 B2 | 11/2014 | Tran et al. |
| 8,940,891 B2 | 1/2015 | Tran et al. |
| 9,012,478 B2 | 4/2015 | Tran et al. |
| 10,138,210 B2 | 11/2018 | Tran et al. |
| 10,214,518 B2 | 2/2019 | Tran et al. |
| 10,537,546 B2 | 1/2020 | Glicklich |
| 10,668,033 B2 | 6/2020 | Tran et al. |
| 10,688,076 B2 | 6/2020 | Glicklich |
| 10,689,372 B2 | 6/2020 | Tran et al. |
| 10,793,529 B2 | 10/2020 | Trans et al. |
| 11,000,500 B2 | 5/2021 | Glicklich |
| 11,098,034 B2 | 8/2021 | Tran et al. |
| 11,123,298 B2 | 9/2021 | Shao et al. |
| 11,426,377 B2 | 8/2022 | Glicklich |
| 2003/0144350 A1 | 7/2003 | Stevenson et al. |
| 2004/0048844 A1 | 3/2004 | Nugiel et al. |
| 2006/0063930 A1 | 3/2006 | Agoston et al. |
| 2006/0258728 A1 | 11/2006 | Tani et al. |
| 2011/0224262 A1 | 9/2011 | Tran et al. |
| 2012/0225937 A1 | 9/2012 | Blackburn et al. |
| 2013/0217706 A1 | 8/2013 | Tran et al. |
| 2015/0126527 A1 | 5/2015 | Tran et al. |
| 2015/0191454 A1 | 7/2015 | Tran et al. |
| 2019/0321328 A1 | 10/2019 | Behan et al. |
| 2020/0368190 A1 | 11/2020 | Adams et al. |
| 2020/0375930 A1 | 12/2020 | Tran et al. |
| 2020/0385357 A1 | 12/2020 | Tran et al. |
| 2021/0212979 A1 | 7/2021 | Adams |
| 2021/0378965 A1 | 12/2021 | Shao et al. |
| 2022/0354819 A1 | 11/2022 | Glicklich |
| 2023/0121825 A1 | 4/2023 | Tran et al. |
| 2023/0172898 A1 | 6/2023 | Glicklich |
| 2023/0404954 A1 | 12/2023 | Tran et al. |
| 2024/0002334 A1 | 1/2024 | Batra et al. |

FOREIGN PATENT DOCUMENTS

| | | |
|---|---|---|
| CA | 2125074 A1 | 12/1994 |
| CN | 1418187 A | 5/2003 |
| CN | 1516690 A | 7/2004 |
| CN | 1735598 A | 2/2006 |
| CN | 1829712 A | 9/2006 |
| CN | 1882532 A | 12/2006 |
| EP | 0028829 A1 | 5/1981 |
| EP | 0442448 A2 | 8/1991 |
| EP | 1013639 A1 | 6/2000 |
| EP | 1046631 A1 | 10/2000 |
| EP | 1716087 A1 | 11/2006 |
| JP | H03160438 A | 7/1991 |
| JP | H06329598 A | 11/1994 |
| JP | H11269138 A | 10/1999 |
| JP | 2005104853 A | 4/2005 |
| JP | 2006083085 A | 3/2006 |
| JP | 2006137856 A | 6/2006 |

(Continued)

OTHER PUBLICATIONS

Caira, Crystalline Polymorphism of Organic Compounds, (Topics in Current Chemistry, 198, p. 163-205). (Year: 1998).*
Descamps, et al. Perspectives on teh amorphisation/million relationship in pharmaceutical materials, Advanced Drug Delivery Reviews, 100, 51-66. (Year: 2016).*
Aguilar et al. Epoprostenol (prostacyclin) therapy in HIV-associated pulmonary hypertension. Am. J. Respir. Crit. Care Med. 162:1846-1850 (2000).
Arehart et al., Prostacyclin, atherothrombosis, and cardiovascular disease. Curr. Med. Chem. 14:2161-2169 (2007).

(Continued)

*Primary Examiner* — Matthew P Coughlin
*Assistant Examiner* — Meghan C Heasley
(74) *Attorney, Agent, or Firm* — WILSON SONSINI GOODRICH & ROSATI

(57) ABSTRACT

Described herein are crystalline forms of a prostacyclin (IP) receptor agonist compound, as well as pharmaceutical compositions thereof, and methods of use thereof in the treatment of diseases or conditions that would benefit from treatment with a prostacyclin (IP) receptor agonist compound.

18 Claims, 35 Drawing Sheets

(56) References Cited

FOREIGN PATENT DOCUMENTS

| | | | | |
|---|---|---|---|---|
| JP | 2007161867 | A | 6/2007 | |
| JP | 2011515396 | A | 5/2011 | |
| JP | 2014210774 | A | 11/2014 | |
| JP | 2016028062 | A | 2/2016 | |
| JP | 2018035194 | A | 3/2018 | |
| WO | WO-9524393 | A1 | 9/1995 | |
| WO | WO-02055484 | A1 | 7/2002 | |
| WO | WO-2007051255 | A1 | 5/2007 | |
| WO | WO-2007133653 | A2 | 11/2007 | |
| WO | WO-2009117095 | A1 * | 9/2009 | ............ A61K 31/17 |
| WO | WO-2010077275 | A1 | 7/2010 | |
| WO | WO-2011037613 | A1 | 3/2011 | |
| WO | WO-2020048299 | A1 | 3/2020 | |
| WO | WO-2023158634 | A1 | 8/2023 | |

OTHER PUBLICATIONS

Asada et al., Discovery of a series of acrylic acids and their derivatives as chemical leads for selective EP3 receptor antagonists, Bioorganic & Medicinal Chemistry, Pergamon, GB 17(18):6567-6582 (2009).

Badesch et al., Continuous intravenous epoprostenol for pulmonary hypertension due to the scleroderma spectrum of disease. A randomized, controlled trial. Ann. Intern. Med. 132:425-434 (2000).

Badesch et al., Prostanoid therapy for pulmonary arterial hypertension. Journal of the American College of Cardiology 43(12 Suppl. S):56S-61S (2004).

Baradia et al., Inhalation therapy to treat pulmonary arterial hypertension. Pharm. Pat. Analyst 1(5):577-588 (2012).

Berge et al. Pharmaceutical Salts. Journal of Pharmaceutical Sciences 66(1):1-19 (Jan. 1977).

Caira: Crystalline Polymorphism of Organic Compounds. Topics in Current Chemistry. 198:163-208 (1998) XP001156954.

Cheng et al., Role of prostacyclin in the cardiovascular response to thromboxane A2. Science 296:539-541 (2002).

Czeslick et al., Inhibition of intracellular tumour necrosis factor (TNF)-alpha and interleukin (IL)-6 production in human monocytes by iloprost. Eur. J. Clin. Invest. 33:1013-1017 (2003).

Dogan et al., Effect of the prostacyclin analogue, iloprost, on infarct size after permanent focal cerebral ischemia. Gen. Pharmacol. 27:1163-1166 (1996).

Driscoll et al., Medical therapy for pulmonary arterial hypertension. Expert Opin. Pharmacother. 9:65-81 (2008).

Fang et al, Induction of prostacyclin/PGI2 synthase expression after cerebral ischemia-reperfusion. J. Cereb. Blood Flow Metab. 26:491-501 (2006).

Fetalvero et al., Cardioprotective prostacyclin signaling in vascular smooth muscle. Prostaglandins Other Lipid Mediat. 82:109-118 (2007).

Fetalvero et al., The prostacyclin receptor induces human vascular smooth muscle cell differentiation via the protein kinase A pathway. Am. J. Physiol. Heart. Circ. Physiol. 290:H1337-H1346 (2006).

Fujiwara et al., A stable prostacyclin analogue reduces high serum TNF-alpha levels in diabetic patients. Exp. Clin. Endocrinol. Diabetes 112:390-394 (2004).

Gainza et al., Role of prostacyclin (epoprostenol) as anticoagulant in continuous renal replacement therapies: efficacy, security and cost analysis. J. Nephrol. 19:648-655 (2006).

Gao et al., A 7-day oral treatment of patients with active rheumatoid arthritis using the prostacyclin analog iloprost: cytokine modulation, safety, and clinical effects. Rheumatol. Int. 22:45-51 (2002).

Goya et al., Effects of the prostaglandin I2 analogue, beraprost sodium, on vascular cell adhesion molecule-1 expression in human vascular endothelial cells and circulating vascular cell adhesion molecule-1 level in patients with type 2 diabetes mellitus. Metabolism Clinical and Experimental 52:192-198 (2003).

Guillory. Chapter 5: Generation of Polymorphs, Hydrates, Solvates, and Amorphous Solids. Polymorphism in Pharmaceutical Solids pp. 183-226 (Brittain, H.G., ed., 1999).

Harada et al., Role of neutrophil elastase in development of pulmonary vascular injury and septic shock in rats. Shock 30(4):379-387 (2008).

Hattori et al. Discovery of diphenylcarbamate derivatives as highly potent and selective IP receptor agonists: orally active prostacyclin mimetics. Part 3. Bioorg Med Chem Lett 15:3091-3095 (2005).

Higuchi et al.Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).

Hoyng et al., Iloprost, a stable prostacyclin analog, reduces intraocular pressure. Invest. Ophthalmol Vis. Sci. 28:470-476 (1987).

Humbert et al., Combination of bosentan with epoprostenol in pulmonary arterial hypertension: Breathe-2. Eur Respir J 24:353-359 (2004).

Humbert et al, Short-term and long-term epoprostenol (prostacyclin) therapy in pulmonary hypertension secondary to connective tissue diseases: results of a pilot study Eur. Respir. J. 13:1351-1356 (1999).

Indian Patent Application No. IN1995DE00358 358/DEL/1995.

Jozefowski et al., Exogenous but not endogenous prostanoids regulate cytokine secretion from murine bone marrow dendritic cells: EP2, DP, and IP but not EP1, EP3, and FP prostanoid receptors are involved. Int. Immunopharmcol. 3:865-878 (2003).

Le Bas et al., Radioiodinated analogs of EP 00652218 for the exploration of the tachykinin NK1 receptor by spect. J Labelled Compd. Radiopharm 44:S280-S282 (2001).

Liu et al., Treatments for pulmonary arterial hypertension. Respiratory Medicine, Baillier Tindall, London, GB 100(5):765-774 (2006).

McCormick et al., Prostacyclin analogues: the next drug-eluting stent? Biochem. Soc. Trans. 35:910-911 (2007).

McGoon et al., Screening, early detection, and diagnosis of pulmonary arterial hypertension: ACCP evidence-based clinical practice guidelines. Chest 126:14S-34S (2004).

McLaughlin et al, Pulmonary arterial hypertension. Pulmonary arterial hypertension. Circulation 114(13):1417-1431 (2006).

Moss. Basic terminology of stereochemistry (IUPAC Recommendations 1996). Pure & Appl. Chem. 68(12):2193-2222 (1996).

Muller et al., Iloprost has potent anti-inflammatory properties on human monocyte-derived dendritic cells. Clinical & Experimental Allergy, Department of Pneumology, University of Freiburg, Germany 40:1214-1221 (2010).

Naeije et al., Expert opinion on available options treating pulmonary arterial hypertension. Expert Opin. Pharmacother. 8:2247-2265 (2007).

PCT/US2023/013032 International Search Report and Written Opinion dated Apr. 3, 2023.

Potapov. Stereochemistry. 2nd Ed [Textbook for Chemistry Majors]. USSR. (1988), p. 202, Publisher (Khimiya, Moscow, USSR) (English translation).

Rabinovitch. Pathobiology of pulmonary hypertension. Annu. Rev. Pathol. Mech. Dis. 2:369-399 (2007).

Robbins et al, Epoprostenol for treatment of pulmonary hypertension in patients with systemic lupus erythematosus. Chest 117:14-18 (2000).

Rosenkranz. Pulmonary hypertension: Current diagnosis and treatment. Clin. Res. Cardiol. 96(8):527-541 (2007).

Rosenzweig. Emerging treatments for pulmonary arterial hypertension. Expert Opin. Emerging Drugs 11(4):609-619 (2006).

Rosenzweig et al., Long-term prostacyclin for pulmonary hypertension with associated congenital heart defects. Circulation 99:1858-1865 (1999).

Sato et al., Effect of OP-2507, a novel prostacyclin analogue on ischemia and reperfusion induced arrhythmias in isolated perfused rat heart. Journal of Molecular and Cellular Cardiology, Academic Press, GB, 22:S74 (1990).

Seiler et al., 2-[3-[2-(4,5-Diphenyl-2-oxazolyl) ethyl] phenoxy] acetic acid (BMY 42393): a new, structurally-novel prostacyclin partial agonist: 1). Inhibition of platelet aggregation and mechanism of action. Thrombosis Research 74(2):115-123 (1994).

Simonneau et al., Clinical classification of pulmonary hypertension. J. Am. Coll. Cardiol. 43:5S-12S (2004).

(56) References Cited

OTHER PUBLICATIONS

Strauss et al., Prostanoid therapy for pulmonary arterial hypertension. Clin. Chest. Med. 28:127-142 (2007).
Takamura et al. Metabolism investigation leading to novel drug design 2: orally active prostacyclin mimetics. Part 5. Bioorg Med Chem Lett 16:4475-4478 (2006).
Zhu et al, Synthesis and mode of action of (125)I- and (3)H-labeled thieno[2,3-c]pyridine antagonists of cell adhesion molecule expression. J. Org. Chem. 67:943-948 (2002).
Co-pending U.S. Appl. No. 17/747,917, inventors Tran; Thuy-Anh et al., filed May 18, 2022.
Co-pending U.S. Appl. No. 18/335,052, inventors Adams; John W. et al., filed Jun. 14, 2023.
Co-pending U.S. Appl. No. 18/491,524, inventor Glicklich; Alan, filed Oct. 20, 2023.
Co-pending U.S. Appl. No. 18/491,529, inventors Shao; Zezhi Jesse et al., filed Oct. 20, 2023.

\* cited by examiner

CRYSTALLINE PROSTACYCLIN (IP) RECEPTOR AGONIST AND USES THEREOF

CROSS-REFERENCE TO RELATED APPLICATIONS

This application claims the benefit of U.S. Provisional Application No. 63/310,469, filed Feb. 15, 2022, which is incorporated herein by reference in its entirety.

FIELD OF THE INVENTION

Described herein are solid state forms of the prostacyclin (IP) receptor agonist ralinepag, as well as pharmaceutical compositions thereof, and methods of use thereof in the treatment of diseases or conditions that would benefit from treatment with ralinepag.

BACKGROUND

The prostacyclin (IP) receptor is expressed on platelets and on the smooth muscle cells of several tissues, including lung, heart, aorta, liver, kidney, and blood vessels. Activation of the IP receptor results in increased cellular cyclic adenosine monophosphate (cAMP) followed by vasodilation in arteries and inhibition of aggregation in platelets. Improved hemodynamics, exercise capacity, and survival have been demonstrated for $PGI_2$ replacement therapies for the treatment of, for example, pulmonary arterial hypertension (PAH).

SUMMARY

The present disclosure relates to various solid state forms of the prostacyclin (IP) receptor agonist ralinepag. Such forms of ralinepag are useful for modulating the activity prostacyclin (IP) receptor agonist in mammals that would benefit from such activity.

In one aspect, described herein is crystalline form of ralinepag that is characterized as having: an X-Ray powder diffraction (XRPD) pattern substantially the same as shown in FIG. 1 as measured using Cu Kα.radiation; or an X-Ray powder diffraction (XRPD) pattern substantially the same as shown in FIG. 2 as measured using Cu Kα.radiation; or an X-Ray powder diffraction (XRPD) pattern substantially the same as shown in FIG. 3 as measured using Cu Kα.radiation; or an X-Ray powder diffraction (XRPD) pattern substantially the same as shown in FIG. 4 as measured using Cu Kα.radiation.

In another aspect, described herein is a crystalline form of ralinepag (Form 1) that is characterized as having an X-Ray powder diffraction (XRPD) pattern substantially the same as shown in FIG. 1 as measured using Cu Kα.radiation; or an XRPD pattern with peaks at 8.8±0.2°2-Theta, 11.7±0.2°2-Theta, 16.2±0.2°2-Theta, 21.3±0.2°2-Theta, 33.8±0.2°2-Theta as measured using Cu Kα.radiation In some embodiments, described herein is a crystalline form of ralinepag (Form 1) that is characterized as having an X-Ray powder diffraction (XRPD) pattern substantially the same as shown in any one of FIG. 12a, FIG. 12b, FIG. 12c, FIG. 12d, FIG. 12e, FIG. 12f, FIG. 13a, FIG. 13b, FIG. 13c, FIG. 13d, FIG. 13e, FIG. 14a, FIG. 14b, FIG. 14c, FIG. 14d, FIG. 14e, FIG. 14f, FIG. 14g, FIG. 15a, FIG. 15b, FIG. 15c, FIG. 16, FIG. 17a, or FIG. 17b as measured using Cu Kα.radiation.

In some embodiments, the crystalline form of ralinepag (Form 1) is further characterized as having: a Thermogravimetric/Differential Thermal Analysis (TGA/DTA) thermogram substantially the same as shown in FIG. 6; or a Differential Scanning Calorimetry (DSC) thermogram substantially the same as shown in FIG. 7.

In some embodiments, the crystalline form of ralinepag (Form 1) is further characterized as having: a Differential Thermal Analysis (DTA) thermogram showing a sharp endothermic event having an onset at about 127.2° C.; a Differential Scanning Calorimetry (DSC) thermogram with a sharp endothermic event having an onset at about 127.5° C.

In some embodiments, the crystalline form of ralinepag (Form 1) is further characterized as having a reversible water uptake of 0.1% (w/w) between 0% and 90% Relative Humidity (RH).

In some embodiments, the crystalline Form 1 of ralinepag is further characterized as having an unchanged XRPD after Dynamic Vapour Sorption (DVS) analysis between 0% and 90% RH.

In another aspect, described herein is a crystalline form of ralinepag (Form 1) that is characterized as having unit cell parameters substantially equal to the following at 100 K:

| | |
|---|---|
| Crystal System | triclinic |
| Space Group | P-1 |
| a (Å) | 10.1269(9) |
| b (Å) | 10.7838(8) |
| c (Å) | 11.1906(8) |
| α (°) | 80.888(3) |
| β (°) | 71.953(3) |
| γ (°) | 68.331(4) |
| Volume (Å$^3$) | 1078.51(15) |
| Z, Z' | 2, 1 |
| Calculated Density (g/cm$^3$) | 1.330 |
| Absorption coefficient (mm$^{-1}$) | 1.858 |
| F(000) | 456.0 |

In yet another aspect, described herein is a crystalline form of ralinepag (Form 2) that is characterized as having an X-Ray powder diffraction (XRPD) pattern substantially the same as shown in FIG. 2 as measured using Cu Kα.radiation; or an XRPD pattern with peaks at 4.1±0.2°2-Theta, 15.5±0.2°2-Theta, 16.9±0.2°2-Theta, 17.9±0.2°2-Theta, 22.8±0.2°2-Theta, 23.7±0.2°2-Theta as measured using Cu Kα.radiation.

In some embodiments, the crystalline form of ralinepag (Pattern 2) is further characterized as having a Thermogravimetric/Differential Thermal Analysis (TGA/DTA) thermogram substantially the same as shown in FIG. 8. In some embodiments, the crystalline form of ralinepag (Pattern 2) is further characterized as having a Differential Thermal Analysis (TGA/DTA) thermogram showing weak endothermic and exothermic events from 81 to 89° C. and a broad endothermic event having an onset at about 124.7° C. In some embodiments, the crystalline form of ralinepag (Pattern 2) is further characterized as having an XRPD that converts to crystalline form of ralinepag (Form 1) on heating. In some embodiments, the crystalline form of ralinepag (Pattern 2) is further characterized as a dimethylsulfoxide solvate.

In yet another aspect, described herein is a crystalline form of ralinepag (Form 3) that is characterized as having an X-Ray powder diffraction (XRPD) pattern substantially the same as shown in FIG. 3 as measured using Cu Kα.radiation; or an XRPD pattern with peaks at 3.6±0.2°2-Theta, 18.7±0.2°2-Theta, 22.2±0.2°2-Theta, 24.2±0.2°2-Theta, 24.3±0.2°2-Theta as measured using Cu Kα.radiation.

In some embodiments, the crystalline form of ralinepag (Form 3) is further characterized as having a Thermogravimetric/Differential Thermal Analysis (TGA/DTA) thermogram substantially the same as shown in FIG. 9. In some embodiments, the crystalline form of ralinepag (Form 3) is further characterized as having a Thermogravimetric Analysis (TGA) trace showing mass loss of about 17.8% from the onset of heating up to approximately 238° C. In some embodiments, the crystalline form of ralinepag (Form 3) is further characterized as having a Differential Thermal Analysis (DTA) thermogram showing a sharp endothermic event having an onset at about 74.6° C. In some embodiments, the crystalline form of ralinepag (Form 3) is further characterized as a hydrate.

In yet another aspect, described herein is a crystalline form of ralinepag (Pattern 4) that is characterized as having an X-Ray powder diffraction (XRPD) pattern substantially the same as shown in FIG. 4 as measured using Cu Kα.radiation; or an XRPD pattern with peaks at 15.0±0.2°2-Theta, 16.7±0.2°2-Theta, 18.0±0.2°2-Theta, 18.7±0.2°2-Theta, 18.9±0.2°2-Theta as measured using Cu Kα.radiation.

In some embodiments, the crystalline form of ralinepag (Pattern 4) is further characterized as having a Thermogravimetric/Differential Thermal Analysis (TGA/DTA) thermogram substantially the same as shown in FIG. 10. In some embodiments, the crystalline form of ralinepag (Pattern 4) is further characterized as having a Differential Thermal Analysis (DTA) thermogram showing a broad endothermic event having an onset at about 29.0° C., a sharp endothermic event having an onset at about 127.8° C., or both. In some embodiments, the crystalline form of ralinepag (Pattern 4) is further characterized as having an XRPD that converts to crystalline form of ralinepag (Form 1) on drying. In some embodiments, the crystalline Pattern 4 of ralinepag is further characterized as having an XRPD that converts to amorphous ralinepag on drying.

In yet another aspect, described herein is amorphous ralinepag that is characterized as having an X-Ray powder diffraction (XRPD) pattern showing a lack of crystallinity. In some embodiments, the amorphous ralinepag is further characterized as converting to crystalline form of ralinepag (Form 1) on drying.

Also described herein is a pharmaceutical composition comprising the crystalline ralinepag that is described herein, and at least one pharmaceutically acceptable excipient. In some embodiments, the pharmaceutical composition is formulated in the form of a solid form pharmaceutical composition that is suitable for administration to a subject by oral administration, intranasal administration, or inhalation. In some embodiments, the pharmaceutical composition is formulated in the form of a solid form pharmaceutical composition for oral administration to a mammal. In some embodiments, the pharmaceutical composition is in the form of a tablet, a pill, or a capsule. In some embodiments, the pharmaceutical composition is administered with a dry powder inhaler (DPI) or metered dose inhaler (MDI).

Also described herein is a pharmaceutical composition comprising amorphous ralinepag and at least one pharmaceutically acceptable excipient. In some embodiments, the pharmaceutical composition is formulated in the form of a solid form pharmaceutical composition that is suitable for administration to a subject by oral administration, intranasal administration, or inhalation. In some embodiments, the pharmaceutical composition is formulated in the form of a solid form pharmaceutical composition for oral administration to a mammal. In some embodiments, the pharmaceutical composition is in the form of a tablet, a pill, or a capsule. In some embodiments, the pharmaceutical composition is administered with a dry powder inhaler (DPI) or metered dose inhaler (MDI).

In one aspect, described herein is a method of treating pulmonary arterial hypertension (PAH) in a subject in need thereof, comprising administering crystalline ralinepag or amorphous ralinepag, or a pharmaceutical composition comprising crystalline ralinepag or amorphous ralinepag. In some embodiments, the PAH is selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH) in a patient. In some embodiments, the PAH is a World Health Organization (WHO) Group 1 PAH. In some embodiments, the subject has WHO/NYHA functional class II to IV symptoms.

In one aspect, described herein is a method of synthesizing an amorphous ralinepag, wherein the amorphous ralinepag is characterized as having an X-Ray powder diffraction (XRPD) pattern showing a lack of crystallinity, the method comprising converting ralinepag of Form 1, Form 3, Pattern 2, or Pattern 4 into an amorphous form. In some embodiments, the method comprises drying ralinepag of crystalline Pattern 4. In some embodiments, the method comprises lyophilizing a ralinepag solution in an organic solvent. In some embodiments, the organic solvent is 1,4-dioxane. In some embodiments, a concentration of the ralinepag solution is at most 5 mg/mL. In some embodiments, a concentration of the ralinepag solution is at most 3 mg/mL.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

DETAILED DESCRIPTION

Figure 1:
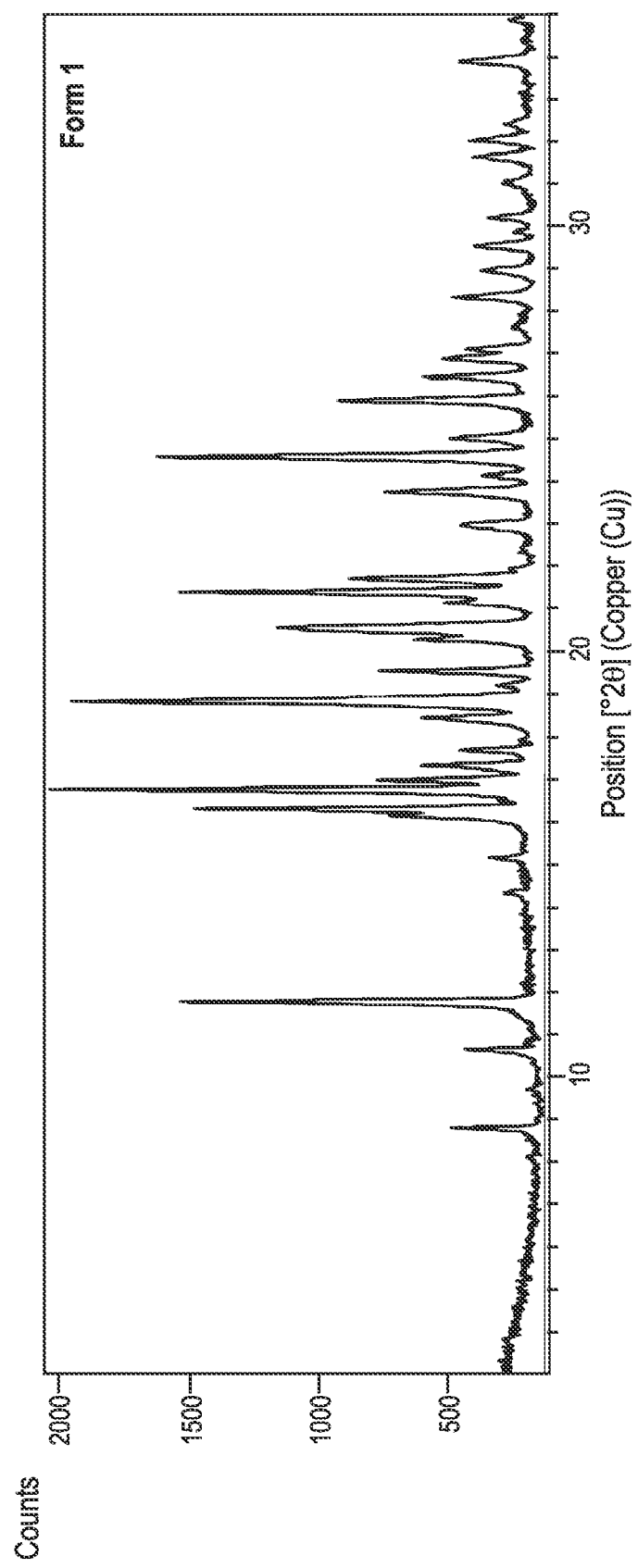
FIG. 1 displays the X-Ray Powder Diffraction (XRPD) pattern of crystalline Form 1 of ralinepag.

While small molecule inhibitors are often initially evaluated for their activity when dissolved in solution, solid state characteristics such as polymorphism are also important.

Polymorphic forms of a drug substance can have different physical properties, including melting point, apparent solubility, dissolution rate, optical and mechanical properties, vapor pressure, and density. These properties can have a direct effect on the ability to process or manufacture a drug substance and the drug product. Moreover, differences in these properties can and often lead to different pharmacokinetics profiles for different polymorphic forms of a drug. Therefore, polymorphism is often an important factor under regulatory review of the 'sameness' of drug products from various manufacturers.

Pulmonary Arterial Hypertension (PAI), $PGI_2$, and IP Receptor Agonists

Pulmonary hypertension (PH) is a rare, progressive disease characterized by elevated pulmonary vascular resistance (PVR) that can lead to right ventricular enlargement, hypertrophy, heart failure and ultimately death. There are five different groups of PH based on different causes according to the current World Health Organization (WHO) classification. These are referred to as PH WHO Groups. Group 1 is pulmonary arterial hypertension (PAH), which is characterized by a thickening and stiffening of the pulmonary vasculature. Although management of PAH has improved significantly in the past 15 years, the mortality rate is still unacceptably high, with a median life expectancy of 7 years after diagnosis. WHO Group 2 includes PH due to left heart disease. In these patients, problems with the heart, rather than the pulmonary vasculature, are primarily responsible for the disease state. WHO Group 3 includes PH due to chronic lung disease and/or hypoxia (low oxygen levels). Group 3 includes pulmonary hypertension associated with interstitial lung disease (PH-ILD) and PH associated with pulmonary fibrosis. WHO Group 4 is called chronic thromboembolic pulmonary hypertension (CTEPH). WHO Group 5 is where PH is secondary to other diseases in ways that are not well understood. Treatment depends on the form of PH. For example, PAH is frequently treated with prostacyclins. Regardless of classification, PH is a serious and often fatal disease.

Severity of PH, including PAH, is graded by four functional classes according to a system originally developed for heart failure by the New York Heart Association (NYHA) and then modified by the WHO for patients with PAH. Patients are usually asymptomatic in the earliest stages of the disease (ie, functional class I), but as the disease progresses, their symptoms, which include exertional dyspnea, fatigue, peripheral edema, and syncope, can be indistinguishable from other cardiorespiratory diseases. Many patients are not diagnosed until they have developed symptoms of WHO/NYHA functional class II or III.

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al., J. Am. Coll. Cardiol., 2004, 43:13 S-24S.)

The compounds disclosed herein are useful in the treatment of pulmonary arterial hypertension (PAH) and symptoms thereof. PAH shall be understood to encompass all forms of pulmonary arterial hypertension described in the 2003 World Health Organization (WHO) clinical classification of pulmonary arterial hypertension. Those forms include idiopathic PAH (IPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HIV infection, PAH associated with drugs or toxins, or PAH associated with Other, and PAH associated with significant venous or capillary involvement.

Idiopathic PAH refers to PAH of undetermined cause.

Familial PAH refers to PAH for which hereditary transmission is suspected or documented.

PAH associated with collagen vascular disease shall be understood to encompass PAH associated with scleroderma, PA H associated with CREST (calcinosis cutis, Raynaud's phenomenon, esophageal dysfunction, sclerodactyl, and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis.

PAH associated with congenital systemic-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of aminorex, PAH associated with ingestion of a fenfluramine compound (e.g., PAH associated with ingestion of fenfluramine or PAH associated with ingestion of dexfenfluramine), PAH associated with ingestion of certain toxic oils (e.g., PAH associated with ingestion of rapeseed oil), PAH associated with ingestion of pyrrolizidine alkaloids (e.g., PAH associated with ingestion of bush tea) and PAH associated with ingestion of monocrotaline.

PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy.

PAH associated with significant venous or capillary involvement shall be understood to encompass PAH associated with pulmonary veno-occlusive disease (PVOD) and PAH associated with pulmonary capillary hemangiomatosis (PCH). (See, e.g., Simonneau et al., J. Am. Coll. Cardiol., 2004, 43:5 S-12S; McGoon et al., Chest, 2004, 126:14 S-34S; Rabinovitch, Annu. Rev. Pathol. Mech. Dis., 2007, 2:369-399; McLaughlin et al., Circulation, 2006, 114:1417-1431; Strauss et al., Clin. Chest. Med., 2007, 28:127-142; Taichman et al., Clin. Chest. Med., 2007, 28:1-22.)

Evidence for the association of PAH with scleroderma and the beneficial effect of an agonist of the $PGI_2$ receptor on PAH is given by Badesch et al. (Badesch et al., Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the $PGI_2$ receptor on PAH were demonstrated by Humbert et al. (Eur. Respir. J., 1999, 13:1351-1356). Evidence for the association of PAH with CREST syndrome and the beneficial effect of an agonist of the $PGI_2$ receptor on PAH were presented by Miwa et al. (Int. Heart J., 2007, 48:417-422). Evidence for the association of PAH with SLE and the beneficial effect of an agonist of the $PGI_2$ receptor on PAH were shown by Robbins et al. (Chest, 2000, 117:14-18). Evidence for the association of PAH with HIV infection and the beneficial effect of an agonist of the $PGI_2$ receptor on PAH were illustrated by Aguilar et al. (Am. J. Respir. Crit. Care Med., 2000, 162: 1846-1850). Evidence for the association of PAH with congenital heart defects (including ASD, VSD and patent ductus arteriosus) and the beneficial effect of an agonist of the $PGI_2$ receptor on PAH were published by Rosenzweig et al. (Circulation, 1999, 99:1858-1865). Evidence for the association of PAH with fenfluramine, or dexfenfluramine, or anorexigens, was presented by Archer et al. (Am. J. Respir. Crit. Care Med., 1998, 158:1061-1067). Evidence for the association of PAH with hereditary hemorrhagic telangiectasia was demonstrated by McGoon et al. (Chest, 2004, 126:14-34). Evidence for the association of PAH with splenectomy was presented by Hoeper et al. (Ann. Intern. Med., 1999, 130:506-509). Evidence for the association of PAH with portal hypertension and the beneficial effect of an agonist of the $PGI_2$ receptor on PAH were shown by Hoeper et al. (Eur. Respir. J., 2005, 25:502-508).

Symptoms of PAH include dyspnea, angina, syncope and edema (McLaughlin et al., Circulation, 2006, 114:1417-1431). The compounds disclosed herein are useful in the treatment of symptoms of PAH.

In some embodiments, pulmonary arterial hypertension (PAH) is selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement. PAH associated with pulmonary veno-occlusive disease (PVOD); and PAH associated with pulmonary capillary hemangiomatosis (PCH) in a patient.

Studies indicate that patients with PAH have alterations in prostacyclin and thromboxane A2 activity, including increased endothelin synthesis, and reduction in the expression of nitric oxide synthase in the pulmonary arterial system, all of which contribute to vasoconstriction/vasodilation imbalance, thrombosis, cell proliferation, and remodeling of the pulmonary arterial walls. Currently available pharmacotherapy for PAH targets the prostacyclin (also termed prostaglandin $I_2$ [$PGI_2$]), endothelin, and nitric oxide pathways.

Treatment guidelines for PAH support the use of an oral endothelin receptor antagonist (ERA), a phosphodiesterase type 5 inhibitor (PDE5-I), or a soluble guanylate cyclase (sGC) stimulator as monotherapy or in combination for PAH patients with WHO/NHYA functional class III. ERAs target the endothelin pathway, whereas PDE5-Is and sGC stimulators target the nitric oxide pathway. There are three commercially available ERAs, ambrisentan, bosentan, and macitentan; two commercially available PDE5-Is, sildenafil and tadalafil; and one commercially available sGC stimulator, riociguat, which are approved for treatment of PAH. These medications can improve exercise capacity, symptoms, and/or cardiopulmonary hemodynamic variables in patients with symptomatic PAH. There is uncertainty as to whether they prolong survival time in this population.

$PGI_2$ is a metabolite of arachidonic acid and is formed via the cyclo-oxygenase pathway. Endothelial cells are the main source of $PGI_2$. The vascular effects of $PGI_2$ and its mimetics are largely mediated by activation of the $PGI_2$ (IP) receptor, and include vasodilation, the inhibition of smooth muscle cell proliferation, and the inhibition of platelet aggregation. The IP receptor is expressed on platelets and on the smooth muscle cells of several tissues, including lung, heart, aorta, liver, kidney, and blood vessels. Activation of the IP receptor results in increased cellular cyclic adenosine monophosphate (cAMP) followed by vasodilation in arteries and inhibition of aggregation in platelets. Improved hemodynamics, exercise capacity, and survival have been clearly demonstrated for $PGI_2$ replacement therapies.

Epoprostenol, a synthetic $PGI_2$ analogue, is a potent vasodilator and inhibitor of platelet aggregation, and was the first therapeutic that was approved for PAH therapy. Epoprostenol improves prognosis for patients with PAH compared to conventional therapy, validating the IP receptor as a target for PAH therapy. However, epoprostenol requires continuous infusion through a portable pump, it is unstable at room temperature, and is associated with intravenous catheter-related infections and thrombosis. Per the treatment algorithm put forth by the 5th World Symposium as well as the European Society of Cardiology/European Respiratory Society (ESC/ERS) guidelines, injectable prostacyclin analogues should be administered in patients whose PAH severity is categorized as WHO/NYHA functional class III through IV.

Subsequent $PGI_2$ analogues, such as treprostinil (continuous subcutaneous and intravenous infusion, intermittent inhalation, and oral) and iloprost (intermittent inhalation), have demonstrated efficacy through improved exercise capacity and/or delay in clinical symptom worsening. These prostacyclins are prescribed for patients with WHO/NYHA functional class II through IV PAH. Although these, prostacyclin analogs address some of the limitations associated with epoprostenol, they have drawbacks with respect to frequent dosing (iloprost) and injection site pain (subcutaneous treprostinil), in addition to typical prostacyclin-associated side effects, such as headache, nausea, flushing, diarrhea, and jaw pain.

Selexipag is an oral, selective IP receptor agonist that is approved in the US and elsewhere for treatment of PAH to delay disease progression and reduce the risk of hospitalization for PAH. The ESC/ERS guidelines recommend using selexipag to treat patients with PAH whose severity is WHO/NYHA functional class II through III. Although selexipag and its active metabolite have modes of action similar to that of endogenous prostacyclin (IP receptor agonism), they are chemically distinct from prostacyclin analogues with different pharmacologic properties. Selexipag has been shown to reduce PVR after 17 weeks of treatment, and demonstrated a reduction in a composite morbidity and mortality endpoint by 40%. However, the short effective half-life of the active metabolite of selexipag (3 to 4 hours) leads to relatively large fluctuations between peak and trough plasma concentrations after BID administration.

Despite the number of treatments available, the functional limitations and survival of patients with PAH remains unsatisfactory. The success of selexipag in delaying disease progression and reducing the risk of hospitalization of PAH supports the utility of oral prostacyclin therapies and paves the way for further optimization of nonprostanoid IP receptor agonists. Research efforts focus on optimizing nonprostanoid IP receptor activation, bioavailability, and PK aimed to provide unremitting and potent target engagement with an oral formulation that provides clinical efficacy similar to parenteral prostacyclins.

As described herein, ralinepag and crystalline forms and the amorphous phase thereof, a pharmaceutical composition thereof, may be an attractive oral alternative to the currently approved oral prostacyclin analogues and nonprostanoid IP receptor agonists to treat PAH. In some embodiments, the compounds disclosed herein are useful in the treatment PH other than PAH. For example, the compounds disclosed herein may be useful for treating forms of Group 3 PH, such as PH-ILD or PH associated with pulmonary fibrosis.

The methods and compositions of the present disclosure can also be suitable for treating other conditions such as platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or another disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

In some embodiments, the methods and compositions of the present disclosure are useful for treating chronic thromboembolic pulmonary hypertension (CTEPH). In some embodiments, the methods and compositions disclosed herein are useful for treating persistent/recurrent CTEPH (WHO Group 4) after surgical treatment. In some embodiments, the methods and compositions disclosed herein are useful for treating inoperable CTEPH to improve exercise capacity and/or WHO functional class.

Ralinepag

Ralinepag refers to "2-([(1r,4r)-4-(((4-chlorophenyl)(phenyl)carbamoyloxy)methyl)-cyclohexyl]methoxy)acetic acid", "Acetic acid, 2-((trans-4-(((((4-chlorophenyl)phenylamino)-carbonyl)oxy)methyl)cyclohexyl)methoxy)-", "2-((trans-4-((((4-Chlorophenyl)(phenyl)carbamoyl)-oxy) methyl)cyclohexyl)methoxy)acetic acid", or "APD-811". Other names may be known.

Ralinepag has the following chemical structure:

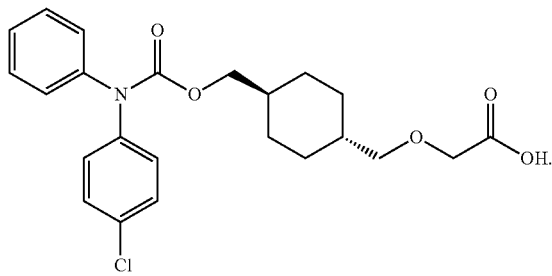 [SMILES: O=C(O)COC[C@H]1CC[C@H](COC(=O)N(c2ccccc2)c2ccc(Cl)cc2)CC1]

Ralinepag is an oral, potent, and selective IP receptor agonist being developed to treat PAH. Ralinepag has been characterized in both single- and multiple-dose studies in a healthy volunteer population. Ralinepag demonstrates a longer $t_{1/2}$ than selexipag (and its active metabolite MRE-269) with less variability in plasma concentrations between doses (peak:trough ratio). The relatively short half-life of selexipag results in the need for BID dosing.

The safety profile suggests that dose-related pharmacology at the IP receptor occurs within the lower dose range of 0.01 mg to 0.2 mg, with adverse effects consistent with those reported for IP receptor agonists. Head-to-head in vitro studies have demonstrated that ralinepag is more potent and efficacious than selexipag at increasing cellular cAMP levels, resulting in improved pulmonary artery vasodilation and better inhibition of human pulmonary artery smooth muscle cell (PASMC) proliferation.

Ralinepag results in improved vasodilation and inhibition of smooth muscle proliferation, which may be an attractive oral alternative to the currently available oral prostacyclin analogues and nonprostanoid IP receptor agonists to treat PAH.

One embodiment herein provides a method of agonizing the IP receptor comprising contacting the IP receptor with ralinepag, or a solid state form thereof, disclosed herein.

The preparation of ralinepag has been previously described (see, WO 2009/117095, U.S. Pat. Nos. 8,895,776, 10,668,033, and US 2020/0375930, each of which is incorporated by reference in its entirety).

In some embodiments, ralinepag is amorphous. As used herein, the term "amorphous" or "amorphous solid form" or "amorphous phase" refers to a solid form lacking crystallinity.

In some embodiments, ralinepag is crystalline. In some embodiments, crystallinity is determined by methods known in the art.

In some embodiments, crystallinity of a solid form is determined by X-Ray Powder Diffraction (XRPD). In some embodiments, crystallinity of a solid form is determined by solid state NMR. In some embodiments, crystallinity of a solid form is determined by Fourier Transform IR Spectroscopy (FTIR).

If multiple diffraction patterns are available, then assessments of particle statistics (PS) and/or preferred orientation (PO) are possible. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks." In general, the more data collected to determine Representative Peaks. the more confident one can be of the classification of those peaks.

"Characteristic peaks," to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° θ. Not all crystalline polymorphs of a compound necessarily have at least one characteristic peak.

The term "preferred orientation" as used herein refers to an extreme case of non-random distribution of the crystallites of a solid state form. In XRPD, the ideal sample is homogenous and the crystallites are randomly distributed in the bulk solid. In a truly random sample, each possible reflection from a given set of planes will have an equal number of crystallites contributing to it. However, when the solid state form is in a preferred orientation this is not the case. Accordingly, comparing the intensity between a randomly oriented diffraction pattern and a preferred oriented diffraction pattern can look entirely different. Quantitative analysis depending on intensity ratios are greatly distorted by preferred orientation. Careful sample preparation is important for decreasing the incidence of a preferred orientation.

Amorphous Ralinepag

Provided herein is amorphous ralinepag. Some embodiments provide a composition comprising amorphous ralinepag.

In some embodiments, amorphous ralinepag is characterized as having an X-Ray powder diffraction (XRPD) pattern showing a lack of crystallinity.

In one aspect, described herein is a method of synthesizing an amorphous ralinepag, wherein the amorphous ralinepag is characterized as having an X-Ray powder diffraction (XRPD) pattern showing a lack of crystallinity, the method comprising converting ralinepag of Form 1, Form 3, Pattern 2, or Pattern 4 into an amorphous form. In some embodiments, the method comprises drying ralinepag of crystalline Pattern 4. In some embodiments, the method comprises drying ralinepag of crystalline Form 1. In some embodiments, the method comprises lyophilizing a ralinepag solution in an organic solvent. In some embodiments, the organic solvent is 1,4-dioxane. In some embodiments, a concentration of the ralinepag solution is at most 10 mg/mL. In some embodiments, a concentration of the ralinepag solution is at most 5 mg/mL.

In some embodiments, a concentration of the ralinepag solution is at most 4 mg/mL. In some embodiments, a concentration of the ralinepag solution is at most 3 mg/mL. In some embodiments, a concentration of the ralinepag solution is at most 2 mg/mL. In some embodiments, a concentration of the ralinepag solution is at most 1 mg/mL. In some embodiments, a concentration of the ralinepag solution is about 0.1 mg/ml to about 5 mg/mL. In some embodiments, a concentration of the ralinepag solution is about 0.1 mg/ml to about 3 mg/mL. In some embodiments, a concentration of the ralinepag solution is about 0.1 mg/ml to about 4 mg/mL.

Crystalline Ralinepag

Also provided herein is crystalline ralinepag.

In some embodiments, the crystalline ralinepag is unsolvated.

In some embodiments, the crystalline ralinepag is solvated. In some embodiments, the crystalline ralinepag is a dimethylsulfoxide solvate.

In some embodiments, the crystalline ralinepag is a hydrate.

Crystalline Form 1 of Ralinepag

In some embodiments, the crystalline ralinepag is crystalline Form 1 of ralinepag. In some embodiments, described herein is a composition comprising crystalline Form 1 of ralinepag. In some embodiments, crystalline Form 1 of ralinepag is referred to as crystalline Pattern 1 of ralinepag.

In some embodiments, crystalline Form 1 of ralinepag is anhydrous. In some embodiments, crystalline Form 1 of ralinepag is not solvated. In some embodiments, crystalline Form 1 of ralinepag is not hydrated.

In some embodiments, crystalline Form 1 of ralinepag is formed from the other solid-state forms described herein. In some embodiments, crystalline Form 1 of ralinepag is the thermodynamically favored solid state form of ralinepag.

In some embodiments, crystalline Form 1 of ralinepag is characterized as having an X-Ray powder diffraction (XRPD) pattern substantially the same as shown in FIG. 1 as measured using Cu Kα.radiation.

In some embodiments, crystalline Form 1 of ralinepag is characterized as having: an XRPD pattern with peaks at 8.8±0.2°2-Theta, 11.7±0.2°2-Theta, 16.2±0.2°2-Theta, 21.3±0.2°2-Theta, 33.8±0.2°2-Theta as measured using Cu Kα.radiation.

In some embodiments, crystalline Form 1 of ralinepag is characterized as having: an XRPD pattern with peaks at 8.8±0.2°2-Theta, 11.7±0.2°2-Theta, and 16.2±0.2°2-Theta as measured using Cu Kα.radiation.

Figure 6:
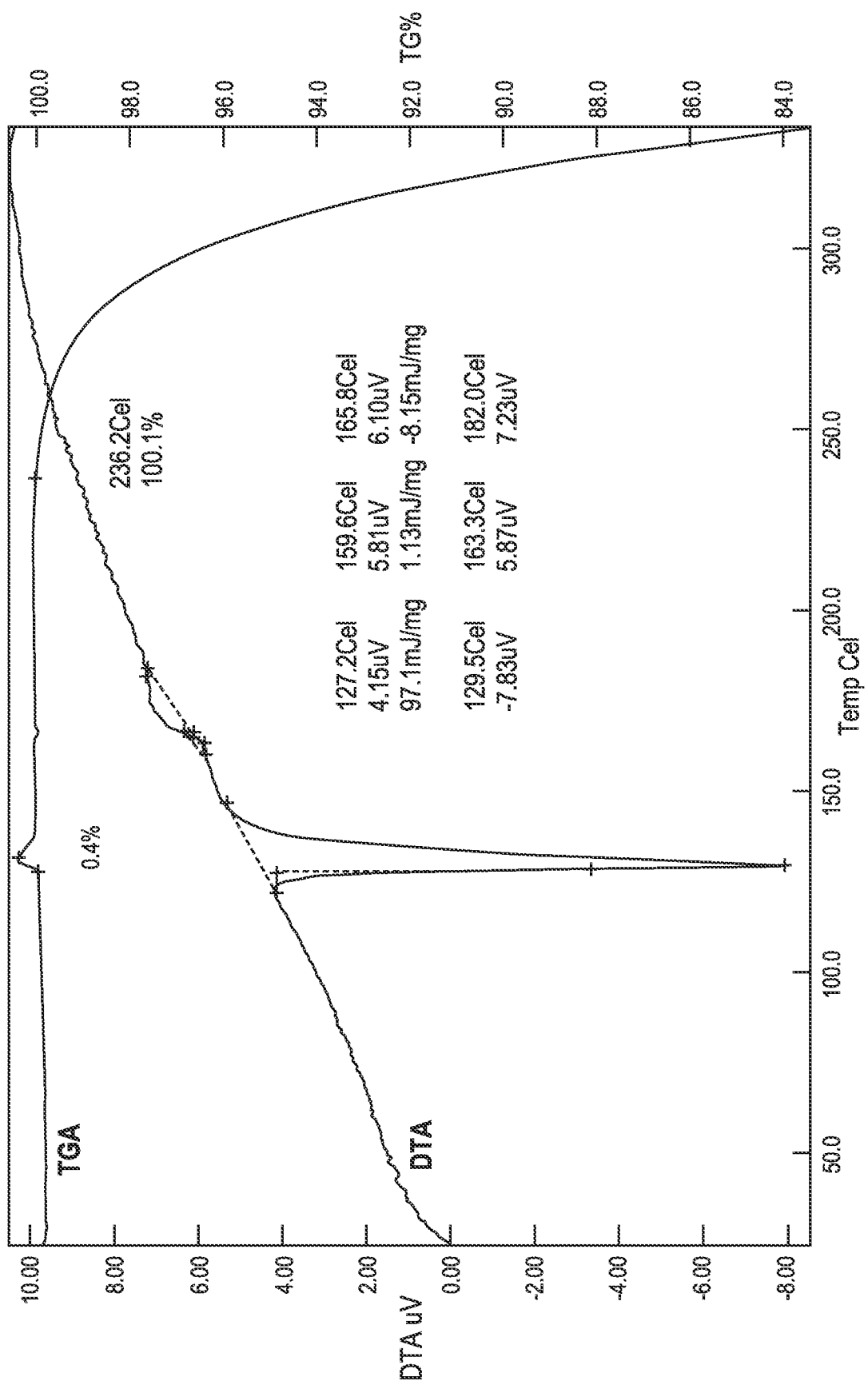
FIG. 6 displays the Thermogravimetric/Differential Thermal Analysis (TGA/DTA) thermogram of crystalline Form 1 of ralinepag.

In some embodiments, crystalline Form 1 of ralinepag is characterized as having: a Thermogravimetric/Differential Thermal Analysis (TGA/DTA) thermogram substantially the same as shown in FIG. 6.

In some embodiments, crystalline Form 1 of ralinepag is characterized as having: a Differential Thermal Analysis (DTA) thermogram showing a sharp endothermic event having an onset at about 127.2° C.

Figure 7:
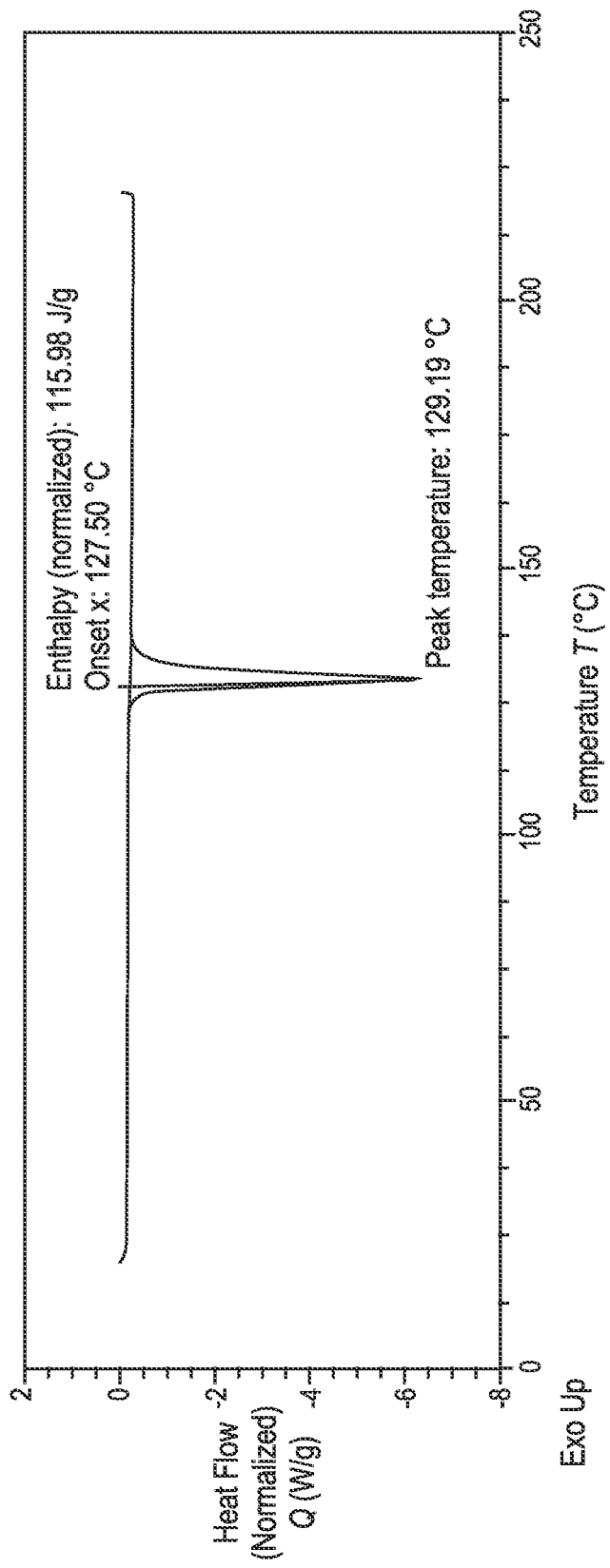
FIG. 7 displays the Differential Scanning Calorimetry (DSC) thermogram of crystalline Form 1 of ralinepag.

In some embodiments, crystalline Form 1 of ralinepag is characterized as having: a Differential Scanning Calorimetry (DSC) thermogram substantially the same as shown in FIG. 7.

In some embodiments, crystalline Form 1 of ralinepag is characterized as having: a DSC thermogram with a sharp endothermic event having an onset at about 127.5° C.

In some embodiments, crystalline Form 1 of ralinepag is characterized as having: a reversible water uptake of 0.1% (w/w) between 0% and 90% Relative Humidity (RH).

In some embodiments, crystalline Form 1 of ralinepag is characterized as having: an unchanged XRPD after Dynamic Vapour Sorption (DVS) analysis between 0% and 90% RH.

In some embodiments, crystalline Form 1 of ralinepag is characterized as having: unit cell parameters substantially equal to the following at 100 K:

| Crystal System | triclinic |
| --- | --- |
| Space Group | P-1 |
| a (Å) | 10.1269(9) |
| b (Å) | 10.7838(8) |
| c (Å) | 11.1906(8) |
| α (°) | 80.888(3) |
| β (°) | 71.953(3) |
| γ (°) | 68.331(4) |
| Volume (Å$^3$) | 1078.51(15) |
| Z, Z' | 2, 1 |
| Calculated Density (g/cm$^3$) | 1.330 |
| Absorption coefficient (mm$^{-1}$) | 1.858 |
| F(000) | 456.0 |

In some embodiments, crystalline Form 1 of ralinepag is characterized as having: an X-Ray powder diffraction (XRPD) pattern substantially the same as shown in FIG. 1 as measured using Cu Kα.radiation; and a Thermogravimetric/Differential Thermal Analysis (TGA/DTA) thermogram substantially the same as shown in FIG. 6; or a Differential Scanning Calorimetry (DSC) thermogram substantially the same as shown in FIG. 7; or both.

In some embodiments, crystalline Form 1 of ralinepag is characterized as having: an XRPD pattern with peaks at 8.8±0.2°2-Theta, 11.7±0.2°2-Theta, 16.2±0.2°2-Theta, 21.3±0.2°2-Theta, 33.8±0.2°2-Theta as measured using Cu Kα.radiation; and a Differential Thermal Analysis (DTA) thermogram showing a sharp endothermic event having an onset at about 127.2° C.; or a DSC thermogram with a sharp endothermic event having an onset at about 127.5° C.; or both.

In some embodiments, crystalline Form 1 of ralinepag is characterized as having: an XRPD pattern with peaks at 8.8±0.2°2-Theta, 11.7±0.2°2-Theta, and 16.2±0.2°2-Theta as measured using Cu Kα.radiation; and a Differential Thermal Analysis (DTA) thermogram showing a sharp endothermic event having an onset at about 127.2° C.; or a DSC thermogram with a sharp endothermic event having an onset at about 127.5° C.; or both.

In some embodiments, crystalline Form 1 of ralinepag is characterized as having a Thermogravimetric/Differential Thermal Analysis (TGA/DTA) thermogram substantially the same as shown in FIG. 6. In some embodiments, crystalline Form 1 of ralinepag is characterized as having a DTA thermogram showing a sharp endothermic event having an onset at about 127.2° C. In some embodiments, crystalline Form 1 of ralinepag is characterized as having a DTA thermogram showing a sharp endothermic event having an onset at about 127.2° C. and a peak at about 129.5° C. In some embodiments, the DTA thermogram of other solid-state forms shows an endothermic event having an onset of 125-128° C., which may be attributed to the formation of crystalline Form 1 of ralinepag through the DTA experiment. In some embodiments, crystalline Form 1 of ralinepag is characterized as having a Differential Scanning Calorimetry (DSC) thermogram substantially the same as shown in FIG. 7. In some embodiments, crystalline Form 1 of ralinepag is characterized as having a a DSC thermogram with a sharp endothermic event having an onset at about 127.5° C. In some embodiments, crystalline Form 1 of ralinepag is characterized as having a a DSC thermogram with a sharp endothermic event having an onset at about 127.5° C. and a peak at about 129.2° C. In some embodiments, the DSC thermogram of other solid-state forms shows an endothermic event having an onset of 125-128° C., which may be attributed to the formation of crystalline Form 1 of ralinepag through the DSC experiment. In some embodiments, crystalline Form 1 of ralinepag is characterized as having a reversible water uptake of 0.1% (w/w) between 0% and 90% Relative Humidity (RH). In some embodiments, crystalline Form 1 of ralinepag is characterized as having an unchanged XRPD after Dynamic Vapour Sorption (DVS) analysis between 0% and 90% RH.

In some embodiments, crystalline Form 1 of ralinepag is characterized as having unit cell parameters substantially equal to the following at 100 K:

| Crystal System | triclinic |
| --- | --- |
| Space Group | P-1 |
| a (Å) | 10.1269(9) |
| b (Å) | 10.7838(8) |
| c (Å) | 11.1906(8) |
| α (°) | 80.888(3) |
| β (°) | 71.953(3) |
| γ (°) | 68.331(4) |
| Volume (Å$^3$) | 1078.51(15) |
| Z, Z' | 2, 1 |
| Calculated Density (g/cm$^3$) | 1.330 |
| Absorption coefficient (mm$^{-1}$) | 1.858 |
| F(000) | 456.0 |

In some embodiments, crystalline Form 1 of ralinepag has an XRPD pattern displaying a preferred orientation. In some embodiments, crystalline Form 1 of ralinepag has an XRPD pattern displaying some peaks with greater intensity than observed from a sample not in a preferred orientation. In some embodiments, crystalline Form 1 of ralinepag has an XRPD pattern displaying only one or two peaks corresponding to a preferred orientation.

Crystalline Pattern 2 of Ralinepag

In some embodiments, the crystalline ralinepag is crystalline Pattern 2 of ralinepag. In some embodiments, described herein is a composition comprising crystalline Pattern 2 of ralinepag.

In some embodiments, crystalline Pattern 2 is formed from lyophilization. In some embodiments, crystalline Pattern 2 is formed only from lyophilization. In some embodiments, crystalline Pattern 2 of ralinepag has poor crystallinity.

In some embodiments, crystalline Pattern 2 of ralinepag is anhydrous. In some embodiments, crystalline Pattern 2 of ralinepag is not solvated. In some embodiments, crystalline Pattern 2 of ralinepag is not hydrated.

Figure 2:
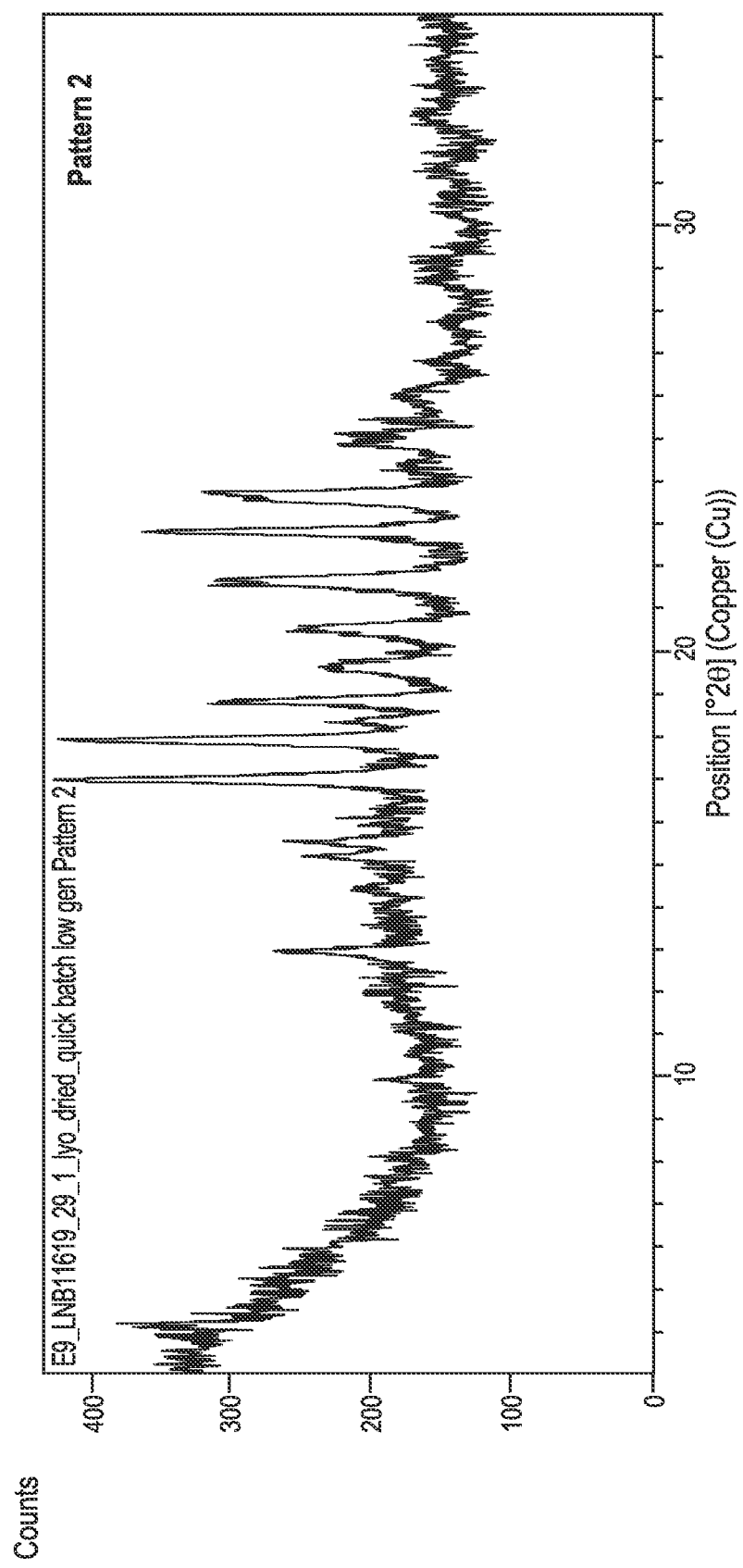
FIG. 2 displays the X-Ray Powder Diffraction (XRPD) pattern of crystalline Pattern 2 of ralinepag.

In some embodiments, the crystalline Pattern 2 of ralinepag is characterized as having an X-Ray powder diffraction (XRPD) pattern substantially the same as shown in FIG. 2 as measured using Cu Kα.radiation.

In some embodiments, the crystalline Pattern 2 of ralinepag is characterized as having an XRPD pattern with peaks at 4.1±0.2°2-Theta, 15.5±0.2°2-Theta, 16.9±0.2°2-Theta, 17.9±0.2°2-Theta, 22.8±0.2°2-Theta, 23.7±0.2°2-Theta as measured using Cu Kα.radiation. In some embodiments, the crystalline Pattern 2 of ralinepag is characterized as having an XRPD pattern with peaks at 4.1±0.2°2-Theta, 15.5±0.2°2-Theta, and 16.9±0.2°2-Theta as measured using Cu Kα.radiation.

Figure 8:
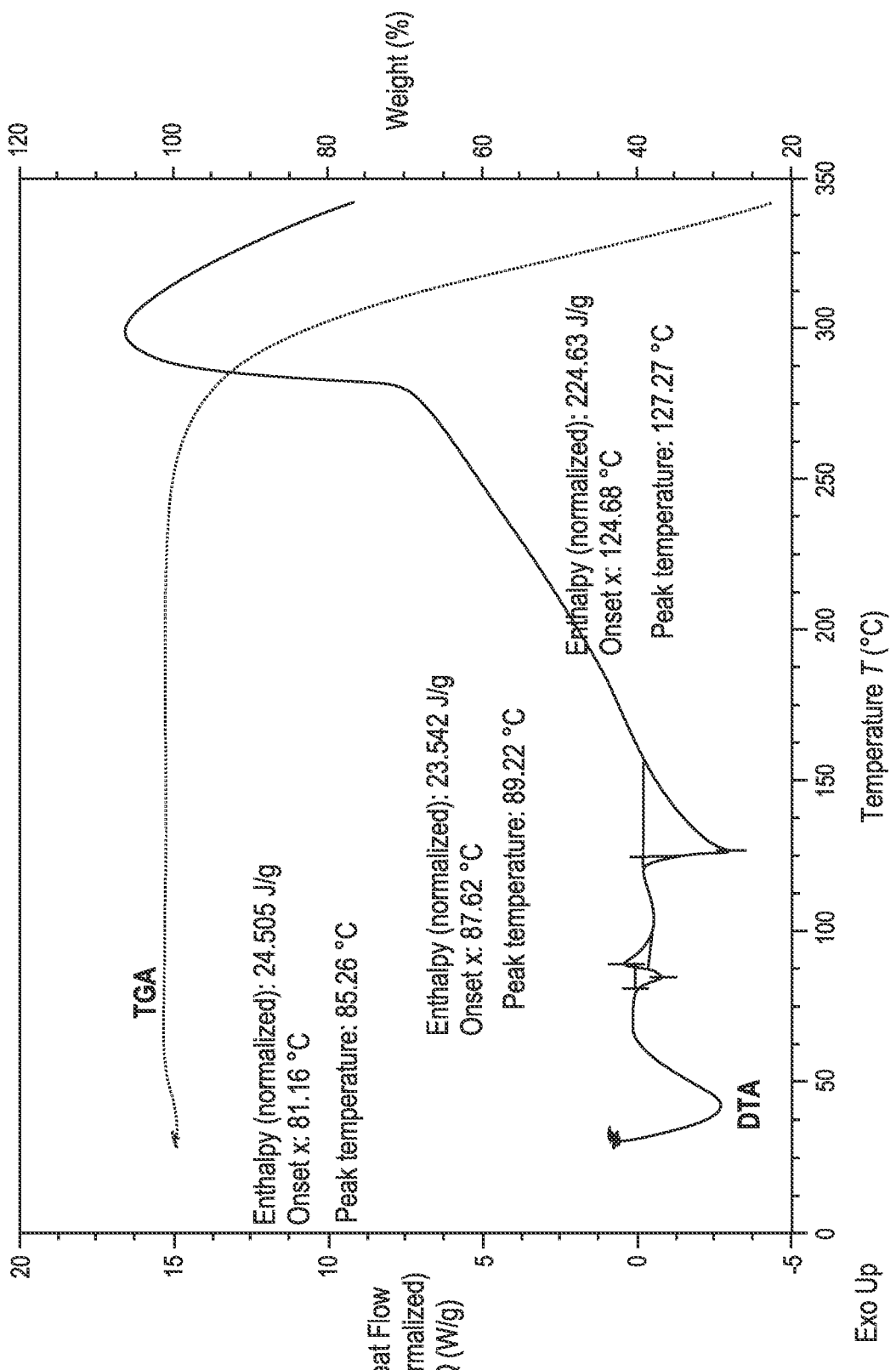
FIG. 8 displays the Thermogravimetric/Differential Thermal Analysis (TGA/DTA) thermogram of crystalline Pattern 2 of ralinepag.

In some embodiments, the crystalline Pattern 2 of ralinepag is further characterized as having a Thermogravimetric/Differential Thermal Analysis (TGA/DTA) thermogram substantially the same as shown in FIG. 8. In some embodiments, the crystalline Pattern 2 of ralinepag is further characterized as having a Differential Thermal Analysis (TGA/DTA) thermogram showing weak endothermic and exothermic events from 81 to 89° C. and a broad endothermic event having an onset at about 124.7° C. In some embodiments, the crystalline Pattern 2 of ralinepag is further characterized as having an XRPD that converts to Form 1 on heating. In some embodiments, the crystalline Pattern 2 of ralinepag is further characterized as a dimethylsulfoxide solvate.

In some embodiments, the crystalline Pattern 2 of ralinepag is characterized as having: an X-Ray powder diffraction (XRPD) pattern substantially the same as shown in FIG. 2 as measured using Cu Kα.radiation; and a Thermogravimetric/Differential Thermal Analysis (TGA/DTA) thermogram substantially the same as shown in FIG. 8.

In some embodiments, the crystalline Pattern 2 of ralinepag is characterized as having: an XRPD pattern with peaks at 4.1±0.2°2-Theta, 15.5±0.2°2-Theta, 16.9±0.2°2-Theta, 17.9±0.2°2-Theta, 22.8±0.2°2-Theta, 23.7±0.2°2-Theta as measured using Cu Kα.radiation; and a Differential Thermal Analysis (TGA/DTA) thermogram showing weak endothermic and exothermic events from 81 to 89° C. and a broad endothermic event having an onset at about 124.7° C. In some embodiments, the crystalline Pattern 2 of ralinepag is characterized as having: an XRPD pattern with peaks at 4.1±0.2°2-Theta, 15.5±0.2°2-Theta, and 16.9±0.2°2-Theta as measured using Cu Kα.radiation; and a Differential Thermal Analysis (TGA/DTA) thermogram showing weak endothermic and exothermic events from 81 to 89° C. and a broad endothermic event having an onset at about 124.7° C.

In some embodiments, crystalline Pattern 2 of ralinepag is characterized as having a Thermogravimetric/Differential Thermal Analysis (TGA/DTA) thermogram substantially the same as shown in FIG. 8. In some embodiments, crystalline Pattern 2 of ralinepag is characterized as having a DTA thermogram showing weak endothermic and exothermic events from 81 to 89° C. and a broad endothermic event having an onset at about 124.7° C. In some embodiments, crystalline Pattern 2 of ralinepag is characterized as having a DTA thermogram showing weak endothermic and exothermic events from 81 to 89° C. and a broad endothermic event having an onset at about 124.7° C. and a peak at about 127.3° C. In some embodiments, the weak endothermic and exothermic events from 81 to 89° C. may be attributed to recrystallization of crystalline Pattern 2 and formation of crystalline Form 1. In some embodiments, the broad endothermic event having an onset at about 124.7° C. may be attributed to crystalline Form 1. In some embodiments, crystalline Pattern 2 of ralinepag is characterized as having an XRPD that converts to Form 1 on heating.

Crystalline Form 3 of Ralinepag

In some embodiments, the crystalline ralinepag is crystalline Form 3 of ralinepag. In some embodiments, described herein is a composition comprising crystalline Form 3 of ralinepag. In some embodiments, crystalline Form 3 of ralinepag is referred to as crystalline Pattern 3 of ralinepag.

In some embodiments, crystalline Form 3 of ralinepag is highly crystalline. In some embodiments, crystalline Form 3 of ralinepag is partially crystalline. In some embodiments, crystalline Form 3 of ralinepag has poor crystallinity.

In some embodiments, crystalline Form 3 of ralinepag is recovered only from samples with dimethylsulfoxide. In some embodiments, crystalline Form 3 of ralinepag is solvated. In some embodiments, crystalline Form 3 of ralinepag is a dimethylsulfoxide solvate.

Figure 3:
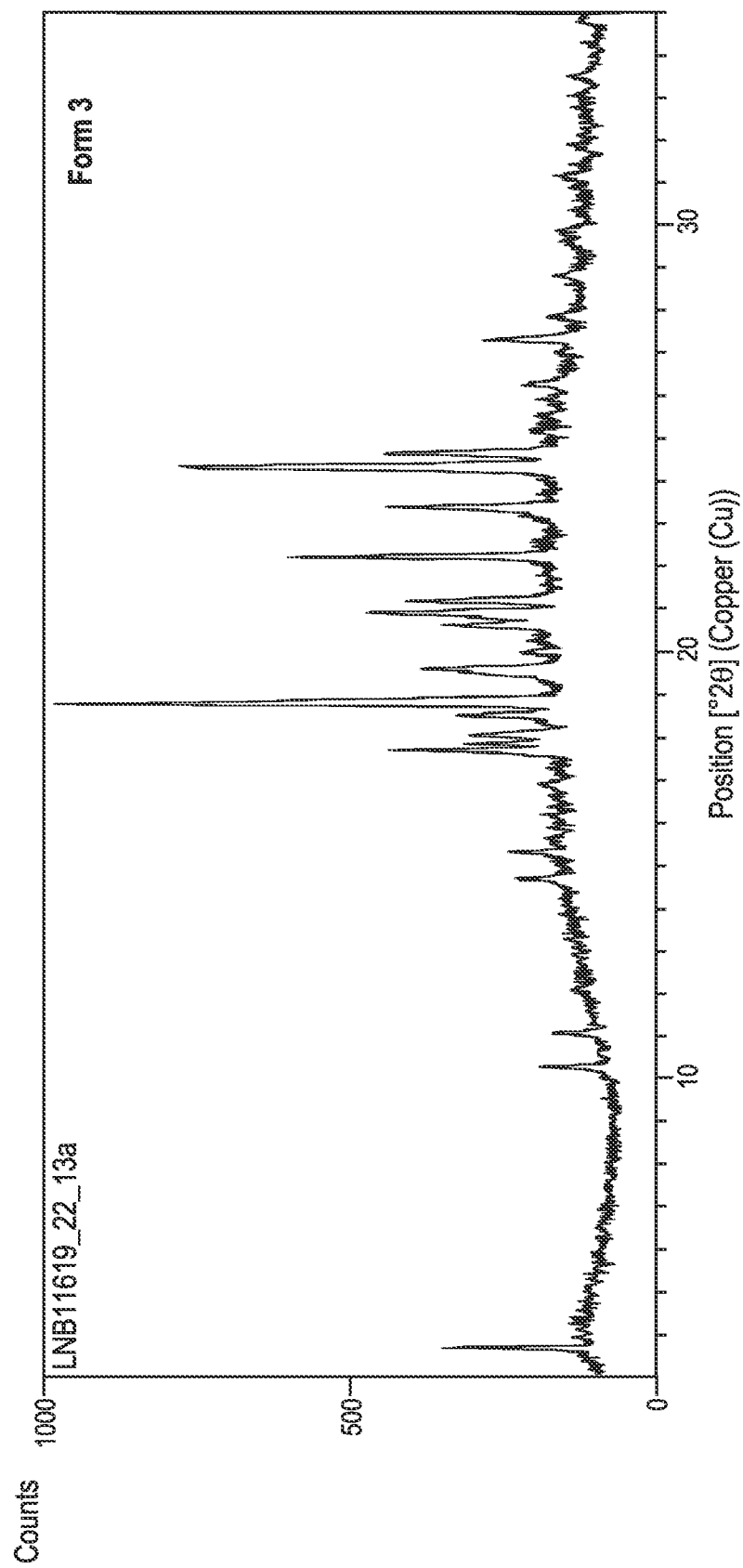
FIG. 3 displays the X-Ray Powder Diffraction (XRPD) pattern of crystalline Form 3 of ralinepag.

In some embodiments, crystalline Form 3 of ralinepag is characterized as having an X-Ray powder diffraction (XRPD) pattern substantially the same as shown in FIG. 3 as measured using Cu Kα.radiation.

In some embodiments, crystalline Form 3 of ralinepag is characterized as having an XRPD pattern with peaks at 3.6 0.2°2-Theta, 18.7±0.2°2-Theta, 22.2±0.2°2-Theta, 24.2±0.2°2-Theta, 24.3±0.2°2-Theta as measured using Cu Kα.radiation. In some embodiments, crystalline Form 3 of ralinepag is characterized as having an XRPD pattern with peaks at 3.6±0.2°2-Theta, 18.7±0.2°2-Theta, and 22.2±0.2°2-Theta as measured using Cu Kα.radiation.

Figure 9:
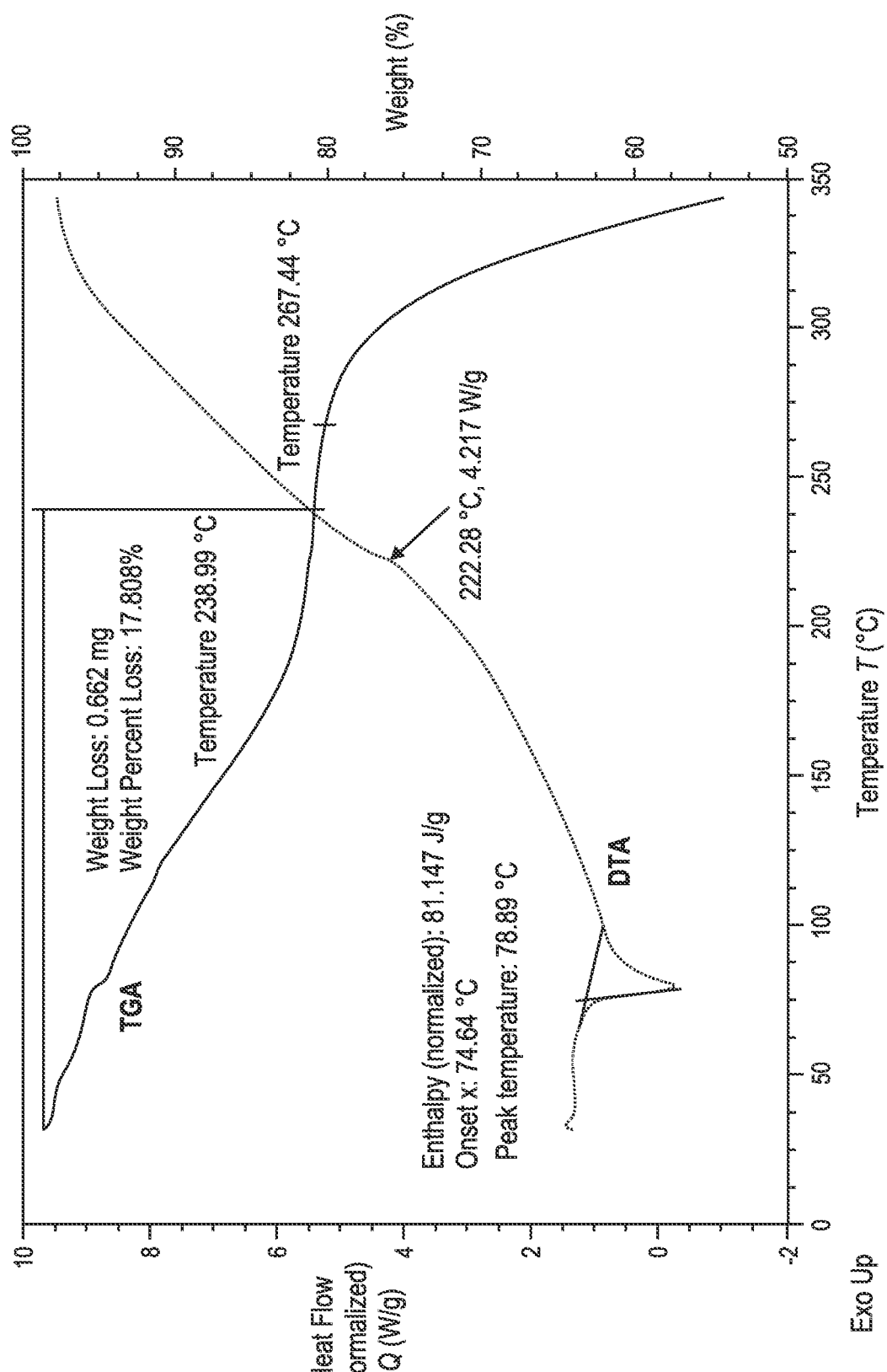
FIG. 9 displays the Thermogravimetric/Differential Thermal Analysis (TGA/DTA) thermogram of crystalline Form 3 of ralinepag.

In some embodiments, the crystalline Form 3 of ralinepag is further characterized as having a Thermogravimetric/Differential Thermal Analysis (TGA/DTA) thermogram substantially the same as shown in FIG. 9. In some embodiments, the crystalline Form 3 of ralinepag is further characterized as having a Thermogravimetric Analysis (TGA) trace showing mass loss of 17.8% from the onset of heating up to approximately 238° C. In some embodiments, the crystalline Form 3 of ralinepag is further characterized as having a Differential Thermal Analysis (DTA) thermogram showing a sharp endothermic event having an onset at about 74.6° C. In some embodiments, the crystalline Form 3 of ralinepag is further characterized as a hydrate.

In some embodiments, crystalline Form 3 of ralinepag is characterized as having an X-Ray powder diffraction (XRPD) pattern substantially the same as shown in FIG. 3 as measured using Cu Kα.radiation; and a Thermogravimetric/Differential Thermal Analysis (TGA/DTA) thermogram substantially the same as shown in FIG. 9.

In some embodiments, crystalline Form 3 of ralinepag is characterized as having: an XRPD pattern with peaks at 3.6±0.2°2-Theta, 18.7 0.2°2-Theta, 22.2±0.2°2-Theta, 24.2±0.2°2-Theta, 24.3 0.2°2-Theta as measured using Cu Kα.radiation; and a TG trace showing mass loss of 17.8% from the onset of heating up to approximately 238° C.; or a DTA thermogram showing a sharp endothermic event having an onset at about 74.6° C.; or both. In some embodiments, crystalline Form 3 of ralinepag is characterized as having: an XRPD pattern with peaks at 3.6±0.2°2-Theta, 18.7±0.2°2-Theta, and 22.2±0.2°2-Theta as measured using Cu Kα.radiation; and a TG trace showing mass loss of 17.8% from the onset of heating up to approximately 238° C.; or a DTA thermogram showing a sharp endothermic event having an onset at about 74.6° C.; or both.

In some embodiments, crystalline Form 3 of ralinepag is characterized as having a Thermogravimetric/Differential Thermal Analysis (TGA/DTA) thermogram substantially the same as shown in FIG. 9. In some embodiments, crystalline Form 3 of ralinepag is characterized as having a TGA trace showing mass loss of 17.8% from the onset of heating up to approximately 238° C. In some embodiments, crystalline Form 3 of ralinepag is characterized as having a DTA thermogram showing a sharp endothermic event having an onset at about 74.6° C.

In some embodiments, crystalline Form 3 of ralinepag is characterized as having a DTA thermogram showing a sharp endothermic event having an onset at about 74.6° C. and a peak at about 78.9° C.

In some embodiments, crystalline Form 3 of ralinepag has an XRPD pattern displaying unknown additional peaks.

Crystalline Pattern 4 of Ralinepag

In some embodiments, the crystalline ralinepag is crystalline Pattern 4 of ralinepag. In some embodiments, described herein is a composition comprising crystalline Pattern 4 of ralinepag.

In some embodiments, crystalline Pattern 4 of ralinepag is highly crystalline. In some embodiments, crystalline Pattern 4 of ralinepag is partially crystalline. In some embodiments, crystalline Pattern 4 of ralinepag has poor crystallinity.

In some embodiments, crystalline Pattern 4 of ralinepag is anhydrous. In some embodiments, crystalline Pattern 4 of ralinepag is not solvated. In some embodiments, crystalline Pattern 4 of ralinepag is not hydrated.

In some embodiments, crystalline Pattern 4 of ralinepag is recovered only from samples with water as an antisolvent. In some embodiments, crystalline Pattern 4 of ralinepag is solvated.

In some embodiments, crystalline Pattern 4 of ralinepag is a hydrate.

Figure 4:
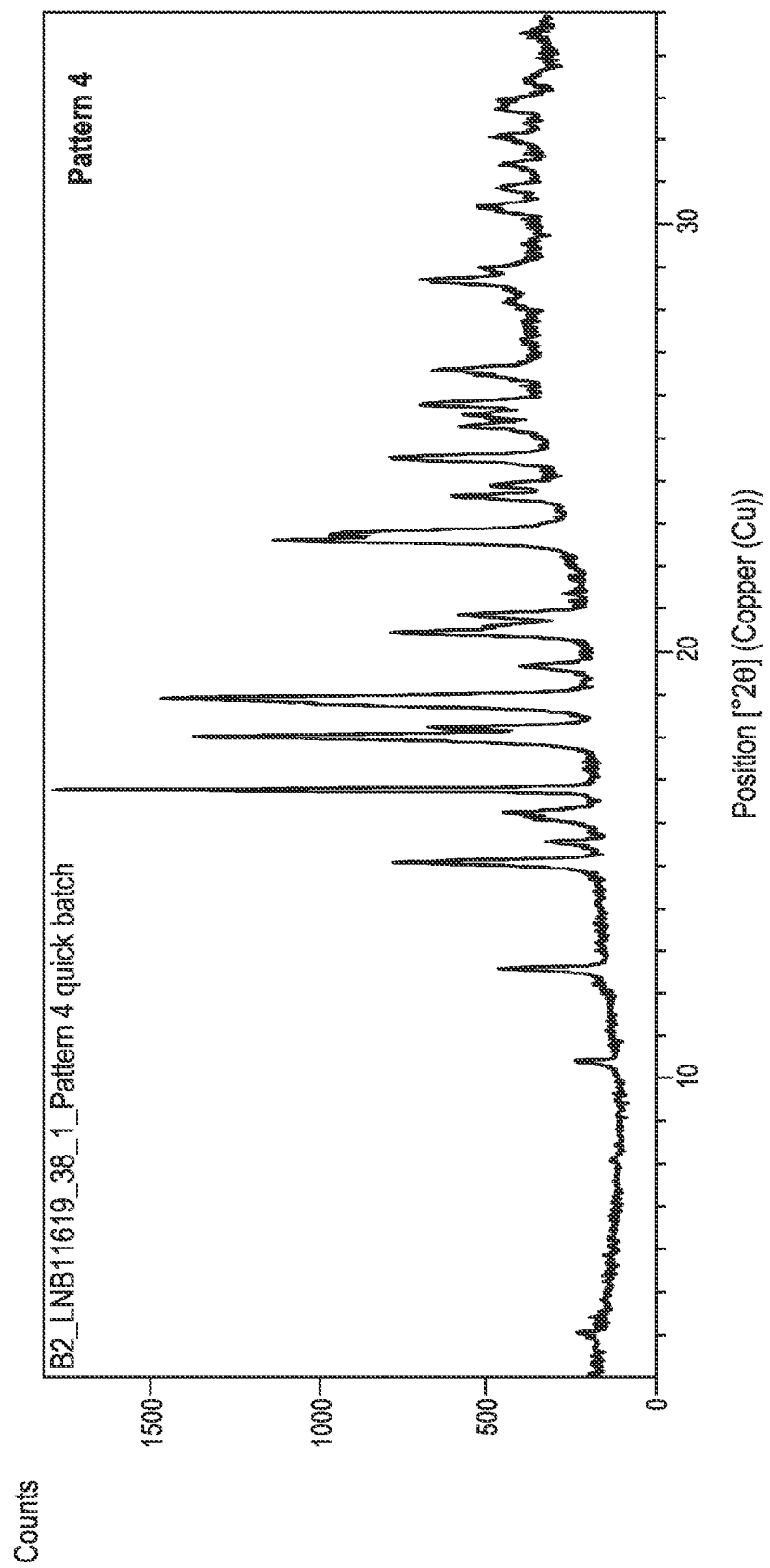
FIG. 4. displays the X-Ray Powder Diffraction (XRPD) pattern of crystalline Pattern 4 of ralinepag.

In some embodiments, crystalline Pattern 4 of ralinepag is characterized as having an X-Ray powder diffraction (XRPD) pattern substantially the same as shown in FIG. 4 as measured using Cu Kα.radiation.

In some embodiments, crystalline Pattern 4 of ralinepag is characterized as having an XRPD pattern with peaks at 15.0±0.2°2-Theta, 16.7±0.2°2-Theta, 18.0±0.2°2-Theta, 18.7±0.2°2-Theta, 18.9 0.2°2-Theta as measured using Cu Kα.radiation. In some embodiments, crystalline Pattern 4 of ralinepag is characterized as having an XRPD pattern with peaks at 15.0±0.2°2-Theta, 16.7±0.2°2-Theta, and 18.0 0.2°2-Theta as measured using Cu Kα.radiation.

Figure 10:
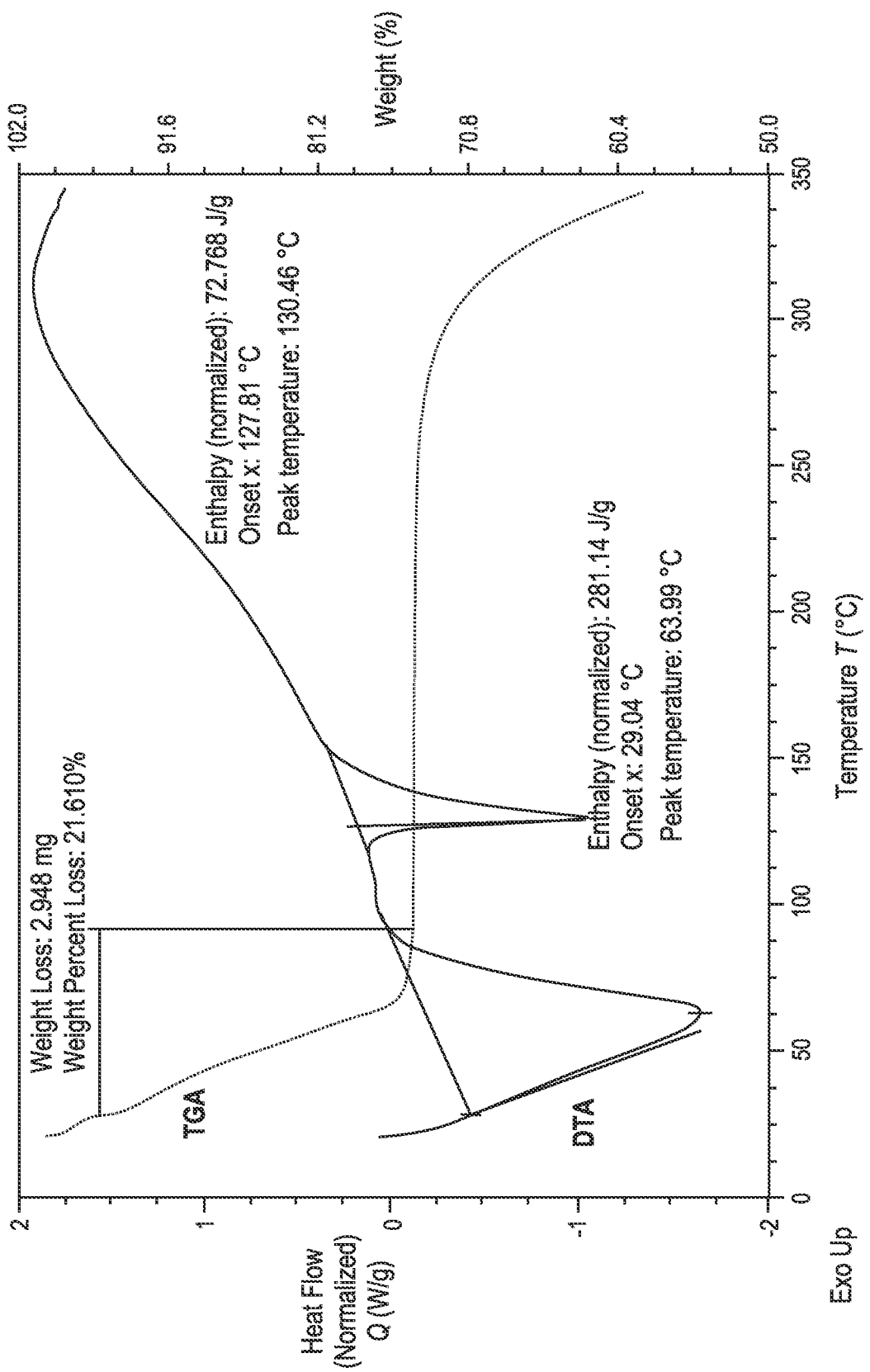
FIG. 10. displays the Thermogravimetric/Differential Thermal Analysis (TGA/DTA) thermogram of crystalline Pattern 4 of ralinepag.

In some embodiments, the crystalline Pattern 4 of ralinepag is further characterized as having a Thermogravimetric/Differential Thermal Analysis (TGA/DTA) thermogram substantially the same as shown in FIG. 10. In some embodiments, the crystalline Pattern 4 of ralinepag is further characterized as having a Differential Thermal Analysis (DTA) thermogram showing a broad endothermic event having an onset at about 29.0° C., a sharp endothermic event having an onset at about 127.8° C., or both. In some embodiments, the crystalline Pattern 4 of ralinepag is further characterized as having an XRPD that converts to Form 1 on drying. In some embodiments, the crystalline Pattern 4 of ralinepag is further characterized as having an XRPD that converts to amorphous ralinepag on drying.

In some embodiments, crystalline Pattern 4 of ralinepag is characterized as having: an X-Ray powder diffraction (XRPD) pattern substantially the same as shown in FIG. 4 as measured using Cu Kα.radiation; and a Thermogravimetric/Differential Thermal Analysis (TGA/DTA) thermogram substantially the same as shown in FIG. 10.

In some embodiments, crystalline Pattern 4 of ralinepag is characterized as having: an XRPD pattern with peaks at 15.0±0.2°2-Theta, 16.7 0.2°2-Theta, 18.0 0.2°2-Theta, 18.7±0.2°2-Theta, 18.9 0.2°2-Theta as measured using Cu Kα.radiation; and a DTA thermogram showing a broad endothermic event having an onset at about 29.0° C., and a sharp endothermic event having an onset at about 127.8° C.

In some embodiments, crystalline Pattern 4 of ralinepag is characterized as having: an XRPD pattern with peaks at 15.0 0.2°2-Theta, 16.7 0.2°2-Theta, and 18.0 0.2°2-Theta as measured using Cu Kα.radiation; and a DTA thermogram showing a broad endothermic event having an onset at about 29.0° C., and a sharp endothermic event having an onset at about 127.8° C.

In some embodiments, crystalline Pattern 4 of ralinepag is characterized as having a Thermogravimetric/Differential Thermal Analysis (TGA/DTA) thermogram substantially the same as shown in FIG. 10. In some embodiments, crystalline Pattern 4 of ralinepag is characterized as having a TG trace showing a significant loss in mass (21.6%) prior to melting.

In some embodiments, this loss in mass may be attributed to loss of residual solvent or water. In some embodiments, crystalline Pattern 4 of ralinepag is characterized as having a DTA thermogram showing a broad endothermic event having an onset at about 29.0° C., and a sharp endothermic event having an onset at about 127.8° C. In some embodiments, crystalline Pattern 4 of ralinepag is characterized as having a DTA thermogram showing a broad endothermic event having an onset at about 29.0° C. and a peak at about 64.0° C., and a sharp endothermic event having an onset at about 127.8° C. and a peak at about 130.4° C. In some embodiments, the broad endothermic event having an onset at about 29.0° C. may be attributed to loss of residual solvent or water and recrystallization of crystalline Pattern 4 and formation of crystalline Form 1. In some embodiments, the sharp endothermic event having an onset at about 127.8° C. may be attributed to crystalline Form 1. In some embodiments, crystalline Pattern 4 of ralinepag is characterized as having an XRPD that converts to Form 1 on drying. In some embodiments, crystalline Pattern 4 of ralinepag is characterized as having an XRPD that converts to Form 1 on drying in air at ambient conditions. In some embodiments, crystalline Pattern 4 of ralinepag is characterized as having an XRPD that converts to amorphous ralinepag on drying.

Salts of Ralinepag

In one aspect, pharmaceutically acceptable salts of ralinepag are prepared, including solvates, hydrates, and unsolvated forms thereof.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like.

Hydrates are formed when the solvent is water, or alcoholates are formed when the solvent is alcohol. Solvates of compounds described herein and crystalline forms thereof are conveniently prepared or formed during the processes described herein. In addition, the compounds and crystalline forms thereof provided herein optionally exist in unsolvated as well as solvated forms.

"Pharmaceutically acceptable," as used herein, refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties. Selection and Use*, Weinheim/Zürich:Wiley-VCH/VHCA, 2002. Pharmaceutical salts typically are more soluble and more rapidly dissolved in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, pharmaceutically acceptable salts are obtained by reacting ralinepag with a base. In such situations, the acidic proton of ralinepag is replaced by a metal ion, e.g., lithium, sodium, potassium, magnesium, calcium, or an aluminum ion. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like.

In some cases, ralinepag coordinates with an organic base, such as, but not limited to, ethanolamine, diethanolamine, triethanolamine, tromethamine, meglumine, N-methylglucamine, dicyclohexylamine, tris(hydroxymethyl)methylamine. In other cases, ralinepag forms salts with amino acids such as, but not limited to, arginine, lysine, and the like.

In some embodiments, ralinepag is prepared as a sodium salt, calcium salt, potassium salt, magnesium salt, meglumine salt, N-methylglucamine salt or ammonium salt.

In another aspect, cocrystals of ralinepag are prepared, including solvates, hydrates, and unsolvated forms thereof. Salts are formed by complete transfer of proton from one compound to another. Salts and cocrystals can be differentiated based by a proton transfer from an acid to base. A complete transfer of proton takes place between acid-base pairs, whereas, no proton transfer occurs during cocrystal formation.

Therapeutic agents, such as ralinepag, that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the preparation of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising ralinepag, or a pharmaceutically acceptable salt thereof, comprise an organic solvent(s). In some embodiments, compositions comprising ralinepag, or a pharmaceutically acceptable salt thereof, include a residual amount of an organic solvent(s).

In some embodiments, compositions comprising ralinepag, or a pharmaceutically acceptable salt thereof, comprise a residual amount of a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising ralinepag, or a pharmaceutically acceptable salt thereof, include a detectable amount of an organic solvent. In some embodiments, the pharmaceutically acceptable salt of ralinepag is a tosylate salt (i.e., ralinepag-Tosyl). In some embodiments, the organic solvent is a Class 3 solvent (i.e., 1-butanol).

In other embodiments are compositions comprising ralinepag, or a pharmaceutically acceptable salt thereof, wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising ralinepag, or a pharmaceutically acceptable salt thereof, wherein the composition comprises a detectable amount of solvent which is less than about 5000 ppm. In yet a further embodiment are compositions comprising ralinepag, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

Definitions

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), and topical administration. Those of skills in the art are familiar with administration techniques that can be employed with the compounds and methods described herein. In some embodiments, the compounds and compositions described herein are administered orally. In some embodiments, the compounds and compositions described herein are administered intranasally or by inhalation.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the diseases or conditions being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "about" means within a statistically meaningful range of a value, such as a stated concentration range, time frame, molecular weight, particle size, temperature or pH. Such a range can be within an order of magnitude, typically within 10%, more typically within 5%, and even more typically within 3% of the indicated value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

The term "substantially the same," as used herein to reference a figure is intended to mean that the figure is considered representative of the type and kind of characteristic data that is obtained by a skilled artisan in view of deviations acceptable in the art. Such deviations may be caused by factors related to sample size, sample preparation, particular instrument used, operation conditions, and other experimental condition variations known in the art. For example, one skilled in the art can appreciate that the endotherm onset and peak temperatures as measured by differential scanning calorimetry (DSC) may vary significantly from experiment to experiment. For example, one skilled in the art can readily identify whether two X-ray diffraction patterns or two DSC thermograms are substantially the same. In some embodiments, when characteristic peaks of two X-ray diffraction patterns do not vary more than 0.2°2-Theta, it is deemed that the X-ray diffraction patterns are substantially the same.

Pharmaceutical Compositions

In some embodiments, the compounds and solid state forms described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically.

Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds and solid state forms described herein are administered either alone or in combination with pharmaceutically acceptable carriers, excipients or diluents, in a pharmaceutical composition. Administration of the compounds and compositions described herein can be effected by any method that enables delivery of the compounds to the site of action.

In some embodiments, pharmaceutical compositions suitable for oral administration are presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art with regard to the type of formulation in question, for example those suitable for oral administration may include flavoring agents.

In some embodiments, the formulations described herein are suitable for oral or nasal inhalation. The inhalable formulations described herein include allow for rapid delivery of ralinepag into the circulatory system and/or target organ (e.g., the lungs) of a mammal in need thereof.

In certain embodiments, the inhalable formulation is in the form of a dry powder. In some embodiments, dry powders are delivered with propellants. In some embodiments, dry powders are delivered without propellants. In some instances, dry powders are one-phase solid-particle blends. In some instances, when actuated, dry powders are two-phase gas-solid systems wherein the dry powder is dispersed in air.

In some embodiments, dry powders contain at least one pharmaceutically acceptable excipient selected from pH-modifying agents, tonicity agents, propellants, preservatives, and surfactants.

In some embodiments, dry powders comprise micronized and/or nano-sized prostacyclin (IP) receptor agonist particles blended with larger carrier particles that prevent aggregation. The excipients and/or carriers in dry powders are endogenous to the lung and are easily metabolized or cleared.

In some instances, dry powders contain lactose as a carrier. In some instances, dry powders comprise starch, mannitol or glucose as a carrier. In some instances, dry powders are formulated as liposomes comprising phospholipids (e.g., phosphatidylcholine), cholesterol, or the like. A carrier particle has low hygroscopicity (e.g., lactose) to prevent aggregation or caking due to absorption of moisture.

In some instances, a dry powder inhalable formulation described herein comprises nano-particles of ralinepag. In some instances, dry powder inhalable formulations described herein comprise crystalline particles. In some embodiments, dry powder inhalable formulations described herein comprise amorphous particles.

In some embodiments, the inhalable formulation is administered with a dry powder inhaler (DPI), or a metered dose inhaler (MDI).

In some instances, the dry powder inhalable formulations described herein are administered with a dry power inhaler (DPI). The medication is usually loaded as a capsule inside a chamber of the inhaler, and then delivered by a patient's inhalation, preferably a deep and forceful inhalation.

In some embodiments, the inhalable formulations described herein are administered with a metered dose inhaler (MDI). In some embodiments, the inhalable formulations described herein comprise a propellant and are pressure packaged for administration of ralinepag using pressurized aerosols. In some embodiments, the metered-dose inhaler comprises three major parts: a canister, a metering val % e, and an actuator. In the case of a pressurized aerosol, the dosage unit may be determined by providing a valve to deliver a metered amount. In some instances, after pressing down the top of the canister, and actuating the MDI, a single metered dose containing the medication in the propellant is released, resulting an aerosol, which is then inhaled by the patient.

In some instances, the dry powder inhalable formulations described herein are administered with a puffer. The dry powder is placed in the puffer and the puffer is squeezed. A portion of the powder is ejected from the spout into the air and is inhaled. Capsules and cartridges of, such as, by way of example only, gelatin for use in an inhaler or insufflator may be formulated containing a dry powder formulation described herein.

Methods of Dosing and Treatment Regimens

In one embodiment, the compounds and solid state forms disclosed herein, or a pharmaceutically acceptable salt thereof, are used in the preparation of medicaments for the treatment of diseases or conditions in a mammal that would benefit from modulation of prostacyclin (IP) receptor agonist activity. Methods for treating any of the diseases or conditions described herein in a mammal in need of such treatment, involves administration of pharmaceutical compositions that include at least one compound disclosed herein or a pharmaceutically acceptable salt, active metabolite, prodrug, or pharmaceutically acceptable solvate thereof, in therapeutically effective amounts to said mammal.

In certain embodiments, the compositions containing the compounds and solid state forms described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-0.6 mg per day. In one embodiment, the desired dose is conveniently presented in a single dose or in divided doses administered simultaneously or at appropriate intervals, for example as two or more sub-doses per day. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

In any of the aforementioned aspects are further embodiments in which the effective amount of the compound disclosed herein, or a pharmaceutically acceptable salt thereof, is: (a) systemically administered to the mammal; and/or (b) administered orally to the mammal; and/or (c) administered by inhalation to the mammal.

In some embodiments, ralinepag, or a pharmaceutically acceptable salt thereof, is administered in an amount that is equivalent to about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.12 mg, about 0.13 mg, about 0.14 mg, about 0.15 mg, about 0.16 mg, about 0.17 mg, about 0.18 mg, about 0.19 mg, about 0.2 mg, about 0.21 mg, about 0.22 mg, about 0.23 mg, about 0.24 mg, about 0.25 mg, about 0.26 mg, about 0.27 mg, about 0.28 mg, about 0.29 mg, about 0.3 mg, about 0.31 mg, about 0.32 mg, about 0.33 mg, about 0.34 mg, about 0.35 mg, about 0.36 mg, about 0.37 mg, about 0.38 mg, about 0.39 mg, about 0.4 mg, about 0.41 mg, about 0.42 mg, about 0.43 mg, about 0.44 mg, about 0.45 mg, about 0.46 mg, about 0.47 mg, about 0.48 mg, about 0.49 mg, about 0.5 mg, about 0.51 mg, about 0.52 mg, about 0.53 mg, about 0.54 mg, about 0.55 mg, about 0.56 mg, about 0.57 mg, about 0.58 mg, about 0.59 mg, or about 0.6 mg of ralinepag. In some embodiments, ralinepag, or a pharmaceutically acceptable salt thereof, is administered at 0.05 mg per day. In some embodiments, ralinepag, or a pharmaceutically acceptable salt thereof, is administered at 0.10 mg per day. In some embodiments, ralinepag, or a pharmaceutically acceptable salt thereof, is administered at 0.15 mg per day. In some embodiments, ralinepag, or a pharmaceutically acceptable salt thereof, is administered at 0.20 mg per day. In some embodiments, ralinepag, or a pharmaceutically acceptable salt thereof, is administered at 0.25 mg per day. In some embodiments, ralinepag, or a pharmaceutically acceptable salt thereof, is administered at 0.30 mg per day. In some embodiments, ralinepag, or a pharmaceutically acceptable salt thereof, is administered at 0.35 mg per day. In some embodiments, ralinepag, or a pharmaceutically acceptable salt thereof, is administered at 0.40 mg per day. In some embodiments, ralinepag, or a pharmaceutically acceptable salt thereof, is administered at 0.45 mg per day. In some embodiments, ralinepag, or a pharmaceutically acceptable salt thereof, is administered at 0.5 mg per day. In some embodiments, ralinepag, or a pharmaceutically acceptable salt thereof, is administered at 0.55 mg per day. In some embodiments, ralinepag, or a pharmaceutically acceptable salt thereof, is administered at 0.60 mg per day. In some embodiments, ralinepag, or a pharmaceutically acceptable salt thereof, is administered at 0.65 mg per day. In some embodiments, ralinepag, or a pharmaceutically acceptable salt thereof, is administered at 0.70 mg per day. In some embodiments, ralinepag, or a pharmaceutically acceptable salt thereof, is administered at 0.75 mg per day. In some embodiments, ralinepag, or a pharmaceutically acceptable salt thereof, is administered at 0.80 mg per day. In some embodiments, ralinepag, or a pharmaceutically acceptable salt thereof, is administered at 0.85 mg per day. In some embodiments, ralinepag, or a pharmaceutically acceptable salt thereof, is administered at 0.9 mg per day. In some embodiments, ralinepag, or a pharmaceutically acceptable salt thereof, is administered at 0.95 mg per day. In some embodiments, ralinepag, or a pharmaceutically acceptable salt thereof, is administered at 1 mg per day. In some embodiments, the dose is administered once a day. In some embodiments, the dose is administered twice a day.

Other embodiments and uses will be apparent to one skilled in the art in light of the present disclosures. The following examples are provided merely as illustrative of various embodiments and shall not be construed to limit the invention in any way.

EXAMPLES

Abbreviations

HPLC-UV=High Performance Liquid Chromatography-Ultraviolet Detection
NMR=nuclear magnetic resonance
RH=relative humidity
v/v=volume ratio
w/w=weight ratio
2-methyl THF=2-methyltetrahydrofuran
tBME=tert-butylmethyl ether
t-BuOH=tert-butanol
DCM=dichloromethane, methylene chloride
DIPE=diisopropyl ether
DMA=N,N-dimethylacetamide
DMF=N,N-dimethylformamide
DMSO=dimethylsulfoxide
DIPE=diisopropyl ether
EtOAc=ethyl acetate
EtOH=ethanol
iPrAc=isopropyl acetate
MEK=methylethyl ketone
MeOH=methanol
MIBK=methylisobutyl ketone
NMP=N-methyl-2-pyrrolidone
THF=tetrahydrofuran
tol=toluene
mL=milliliter(s)
μL=microliter(s)

The following examples are provided for illustrative purposes only and not to limit the scope of the claims provided herein.

Example 1: Preparation of Ralinepag

The preparation of ralinepag has been previously described (see, WO 2009/117095, U.S. Pat. Nos. 8,895,776, 10,668,033, and US 2020/0375930, each of which is incorporated by reference in its entirety).

Example 2: Preparation of Amorphous Ralinepag from Crystalline Form 1 of Ralinepag Example 2a: Attempt 1

To prepare amorphous material for primary polymorph screening, 1.2 g of ralinepag was dissolved in 336 mL of 1,4-dioxane, split into 24 vials (~50 mg of ralinepag per sample). The vials of solution were frozen at −50° C. before being freeze-dried overnight. An aliquot of lyophilised solid was analysed by XRPD and confirmed to be poorly crystalline Form 1.

Example 2b: Attempt 2

The solids from Example 2a were redissolved in 100 mL methanol and the solvent was removed via rotary evaporation. An aliquot of solid was analysed by XRPD and confirmed to be Form 1.

Example 2c: Attempt 3

The solids from Example 2b were redissolved in 100 mL DCM and the solvent was removed via rotary evaporation. An aliquot of solid was analysed by XRPD and confirmed to be Form 1.

Example 2d: Attempt 4

The solids from Example 2c were dissolved in 240 mL tert-butanol, the solution split between 24 vials and freeze-dried as described in Example 2a. An aliquot of solid was analysed by XRPD and confirmed to be Form 1.

Example 2e: Attempt 5

The solid from one vial from Example 2d was dissolved in 200 μL DCM before 2 mL heptane was added in bulk as an anti-solvent to precipitate solid. A small amount of precipitate was noted which stuck to the sides of the vial. The solution was decanted and the solid was removed using a spatula for XRPD analysis. Form 1 was observed.

Example 2f: Attempt 6

All solids from Examples 2d and 2e were combined and redissolved in 336 mL of 1,4-dioxane, before being split into 24 vials and freeze-dried as described in Example 2a. An aliquot of solid was analysed by XRPD and confirmed to be amorphous ralinepag. This was used for the primary polymorph screen.

Example 2g: Attempt 7

To produce additional amorphous material, 300 mg of ralinepag was dissolved in 84 mL 1,4-dioxane, split equally between 6 vials and lyophilized as before. An aliquot of solid was analysed by XRPD and confirmed to be a new Pattern 2.

Example 2i: Attempt 8

The 6 vials of lyophilized ralinepag from Example 2g were each dissolved in 16 mL 1,4-dioxane and lyophilized as before. An aliquot of solid was analysed by XRPD and confirmed to be Pattern 2. The samples were dried under vacuum at 40° C. for approximately 21 h and an aliquot of solid was analysed by XRPD and found Pattern 2 to be retained. This was analysed by TGA/DTA.

Summary of Results

As seen in attempts 1 to 8, Fast evaporation of MeOH and DCM, heptane addition to a DCM solution, lyophilization of t-BuOH and 1,4-dioxane solutions produced Form 1. However, amorphous ralinepag was successfully prepared via lyophilization of a more dilute 1,4-dioxane solution of ralinepag.

Amorphous material was used for the primary polymorph screen to eliminate the presence of any potential seed material in the experiments.

Example 3: Solvent Solubility Study of Ralinepag

To prepare amorphous material for solubility testing, 330 mg of ralinepag was dissolved in 33 mL tert-butanol (with gentle heating applied via a heatgun) before being split evenly into 33 vials (~10 mg of ralinepag per sample). The vials of solution were frozen at −50° C. before being freeze-dried overnight. One vial of solid was analyzed by XRPD to confirm that ralinepag had been rendered amorphous. However, as in Example 2g, a poorly crystalline Pattern 2 was observed.

32 solvents and solvent systems were added to 32×10 mg of lyophilized ralinepag in 50 μL aliquots for the first 300 μL or until complete dissolution was noted. If complete dissolution was not observed, 100 μL aliquots were added thereafter up to 1 mL total solvent. Between each addition, the mixture was manually shaken for a few seconds and if complete dissolution was not apparent, the mixture was heated to about 40° C. and checked again.

Where complete dissolution occurred, the solvent was allowed to evaporate at ambient temperature. Where complete dissolution was not observed, the solids were isolated via centrifuge filtration. Recovered solids were analyzed by XRPD.

Results from the solvent screen are outlined in Table 1.

TABLE 1

Solvent solubility results for amorphous* ralinepag

| Solvent | Estimated Solubility (mg/mL) | XRPD of Recovered Solids |
| --- | --- | --- |
| 1,1-dimethoxymethane | 50 (H) | Form 1* |
| 1,2-dichloroethene | 200 (H) | Form 1 |
| 1,4-dioxane | 200 (H) | Form 1† |
| 1-butanol | 50 (H) | no solid recovered |
| 1-propanol | 50 (H) | Form 1† |
| 2-ethoxyethanol | 200 (H) | Form 1† |
| 2-methyltetrahydrofuran | 200 | Form 1† |
| 2-methyl-1-propanol | 50 (H) | Form 1† |
| 2-propanol | 50 (H) | Form 1 |
| ethanol/water (48:52% v/v) | <10 | Form 1 |
| ethanol/water (93:7% v/v) | 100 (H) | Form 1† |
| ethanol/water (98.5:1.5% v/v) | 100 | Form 1† |
| acetone | 200 | Form 1* |
| acetonitrile | 40 (H) | Form 1† |
| anisole | 200 | Form 1 |

TABLE 1-continued

Solvent solubility results for amorphous* ralinepag

| Solvent | Estimated Solubility (mg/mL) | XRPD of Recovered Solids |
| --- | --- | --- |
| benzyl alcohol | 200 | no solid recovered |
| butyl acetate | 50 (H) | Form 1† |
| dimethylsulfoxide | 200 (H) | Form 3 |
| ethanol | 100 (H) | Form 1† |
| ethyl acetate | 100 (H) | Form 1† |
| heptane | <10 | Form 1 |
| isopropyl acetate | 66.7 (H) | Form 1 |
| methanol | 200 (H) | Form 1† |
| methylethyl ketone | 200 (H) | Form 1† |
| methylisobutyl ketone | 100 (H) | Form 1† |
| N,N-dimethylacetamide | 200 | Form 1 |
| N,N-dimethylformamide | 200 | Form 1 |
| N-methyl-2-pyrrolidone | 200 | no solid recovered |
| tert-butylmethyl ether | 25 (H) | Form 1† |
| tetrahydrofuran | 200 (H) | Form 1† |
| toluene | 14.3 (H) | Form 1† |
| water | <10 | Form 1* |

(H) = heated to 40° C.;
*poorly crystalline;
†preferred orientation

The poorly crystalline ralinepag was found to be soluble in 29 of the 32 solvent systems at a concentration of 10 mg/mL or greater.

No solid was obtained from 1-butanol, benzyl alcohol, or N-methylpyrrolidone.

A new pattern was produced from the solid recovered upon evaporation of dimethylsulfoxide, Form 3.

Poorly crystalline Form 1 was recovered upon evaporation of 1,1-dimethoxymethane, acetone, and water.

The remaining solvent systems produced Form 1.

The following samples produced crystalline Form 1 of ralinepag in a preferred orientation, as described herein: 1,4-dioxane, 1-propanol, 2-ethoxyethanol, 2-methyltetrahydrofuran, 2-methyl-1-propanol, ethanol/water (93:7% v/v), ethanol/water (98.5:1.5% v/v), acetonitrile, butyl acetate, ethanol, ethyl acetate, methanol, methylethyl ketone, methylisobutyl ketone, tert-butylmethyl ether, tetrahydrofuran, and toluene.

Example 4: Polymorph Screen of Ralinepag

Using amorphous material prepared from Example 2f above, various solvent systems were added in attempt to form slurries (where possible). The slurries/solutions were thermally cycled (with agitation) between ambient temperature and 40° C. (4-hour cycles) for 72 h (no specified heat/cool rate).

Any solid material remaining post-temperature cycle was isolated by centrifuge filtration and the isolated material was analyzed by XRPD. The solids were dried in a vacuum oven at 40° C. for 2 h before being analyzed by XRPD again.

The isolated mother liquors were split evenly into 3 and the following experiments were carried out:
 (a) Evaporation at ambient temperature.
 (b) Crash cooling at 5° C. initially, and then −20° C. if no solid was observed.
 (c) Anti-solvent addition: 2 mL of anti-solvent was added, and the samples were left overnight at ambient temperature.

Where no solids were recovered post-thermal cycling, the slurries produced after anti-solvent addition were thermally cycled as described above. Any solids recovered were analysed by XRPD, dried as described above and analysed by XPRD again. All patterns were analyzed TGA/DTA and NMR where material amounts allowed.

Results from the polymorph screen are found in Tables 2 and 3.

TABLE 2

Solvents used in the polymorph screening of ralinepag

| Solvent | Volume Added (µL) | Slurry Post-Solvent Addition? | Slurry Post-Thermal Cycling? | Anti-Solvent |
|---|---|---|---|---|
| 1,4-dioxane | 100 | Yes | No* | heptane |
| 1-propanol | 300 | Yes | Yes | heptane |
| 2-ethoxyethanol | 200 | Yes | No* | heptane |
| 2-methyltetrahydrofuran | 100 | Yes | Yes | heptane |
| 2-propanol | 300 | Yes | Yes | heptane |
| ethanol/water (93:7% v/v) | 300 | Yes | Yes | water |
| ethanol/water (98.5:1.5% v/v) | 300 | Yes | Yes | water |
| acetone | 200 | Yes | No* | heptane |
| acetonitrile | 600 | Yes | Yes | water |
| anisole | 200 | Yes | Yes | heptane |
| benzyl alcohol | 100 | Yes | Yes | heptane |
| butyl acetate | 300 | Yes | Yes | heptane |
| dimethylsulfoxide | 100 | Yes | No* | water |
| ethanol | 210 | Yes | Yes | heptane |
| ethyl acetate | 210 | Yes | Yes | heptane |
| isopropyl acetate | 300 | Yes | Yes | heptane |
| methanol | 100 | Yes | Yes | heptane |
| methylethyl ketone | 100 | Yes | Yes | heptane |
| methylisobutyl ketone | 210 | Yes | Yes | heptane |
| N,N-dimethylformamide | 100 | No | No* | water |
| tert-butylmethyl ether | 900 | Yes | No* | heptane |
| tetrahydrofuran | 100 | No | No* | heptane |
| toluene | 1500 | Yes | Yes | heptane |
| water | 2000 | Yes | Yes | — |
| 1-butanol | 400 | Yes | Yes | heptane |
| 2-methoxyethanol | 150 | Yes | No* | heptane |
| diisopropyl ether | 600 | Yes | Yes | heptane |
| chloroform | 200 | No | No* | heptane |
| N,N-dimethylacetamide | 100 | No | No* | water |
| N-methyl-2-pyrrolidone | 100 | No | No* | water |

*anti-solvent added and the resulting solution/slurry was thermally cycled as before

TABLE 3

XRPD results of solids obtained from polymorph screening of ralinepag

| | XRPD of Recovered Solids | | | | |
|---|---|---|---|---|---|
| Solvent | Post-Thermal Cycling | Post-Thermal Cycling (dried) | Evaporation | Crash Cooling | Anti-Solvent Addition |
| 1,4-dioxane | Form 1** | Form 1 | Form 1† | n.s. | Form 1 |
| 1-propanol | Form 1 | Form 1 | n.s. | n.s. | Form 1† |
| 2-ethoxyethanol | Form 1**; additional peak at 11° 2θ | Form 1; additional peak at 5.6° 2θ | Form 1† | Form 1† | Form 1† |
| 2-methyltetrahydrofuran | Am., with some Form 1 peaks | Form 1 | n.s. | n.s. | Am., with some Form 1 peaks |
| 2-propanol | Form 1 | Form 1 | n.s. | n.s. | n.s. |
| ethanol/water (93:7% v/v) | Form 1 | Form 1 | n.s. | n.s. | Am. |
| ethanol/water (98.5:1.5% v/v) | Form 1 | Form 1 | n.s. | n.s. | Am. |
| acetone | Form 1**,† | Form 1† | Form 1† | Am., with some Form 1 peaks | Am., with some Form 1 peaks |
| acetonitrile | Form 1 | Form 1 | Form 1† | n.s. | Am. |
| anisole | Form 1 | Form 1 | n.s. | n.s. | n.s. |
| benzyl alcohol | Am., with some Form 1 peaks | Form 1* | n.s. | n.s. | n.s. |
| butyl acetate | Form 1 | Form 1 | n.s. | n.s. | Am., with some Form 1 peaks |
| dimethylsulfoxide | Form 1*,** | Form 1; additional peak at 8.2° 2θ | Form 3; some additional peaks | n.s. | Form 1 |
| ethanol | Form 1 | Form 1 | n.s. | n.s. | Am., with some Form 1 peaks |
| ethyl acetate | Form 1 | Form 1 | n.s. | n.s. | Am., with some Form 1 peaks |
| isopropyl acetate | Form 1 | Form 1 | n.s. | n.s. | insufficient solid for XRPD |
| methanol | Form 1 | Form 1 | n.s. | n.s. | n.s. |
| methylethyl ketone | Form 1; weak peak at 10.5° 2θ | Form 1 | n.s. | n.s. | n.s. |

TABLE 3-continued

XRPD results of solids obtained from polymorph screening of ralinepag

| Solvent | Post-Thermal Cycling | Post-Thermal Cycling (dried) | Evaporation | Crash Cooling | Anti-Solvent Addition |
|---|---|---|---|---|---|
| methylisobutyl ketone | Form 1 | Form 1 | n.s. | n.s. | Form 1† |
| N,N-dimethylformamide | Form 1*,** | Form 1 | Form 1† | n.s. | Form 1; weak peaks at 4 and 10.5 2θ |
| tert-butylmethyl ether | Form 1*,* | Form 1* | Form 1† | n.s. | Form 1 |
| tetrahydrofuran | Am. | Form 1 | Form 1† | n.s. | Form 1 |
| toluene | Form 1 | Form 1 | n.s. | n.s. | Form 1 |
| water | Form 1; some Am. | Form 1 | n.s. | n.s. | — |
| 1-butanol | Form 1 | Form 1 | n.s. | n.s. | n.s. |
| 2-methoxyethanol | n.s.** | n.s. | Form 1† | n.s. | n.s. |
| diisopropyl ether | Form 1 | Form 1 | n.s. | n.s. | n.s. |
| chloroform | Form 1** | Form 1 | Form 1†; additional peak at 10° 2θ | n.s. | Form 1** |
| N,N-dimethylacetamide | Am.** | Form 1* | Form 1† | n.s. | Pattern 4 |
| N-methyl-2-pyrrolidone | Am.** | Form 1* | n.s. | n.s. | Pattern 4 |

Figure 14A:
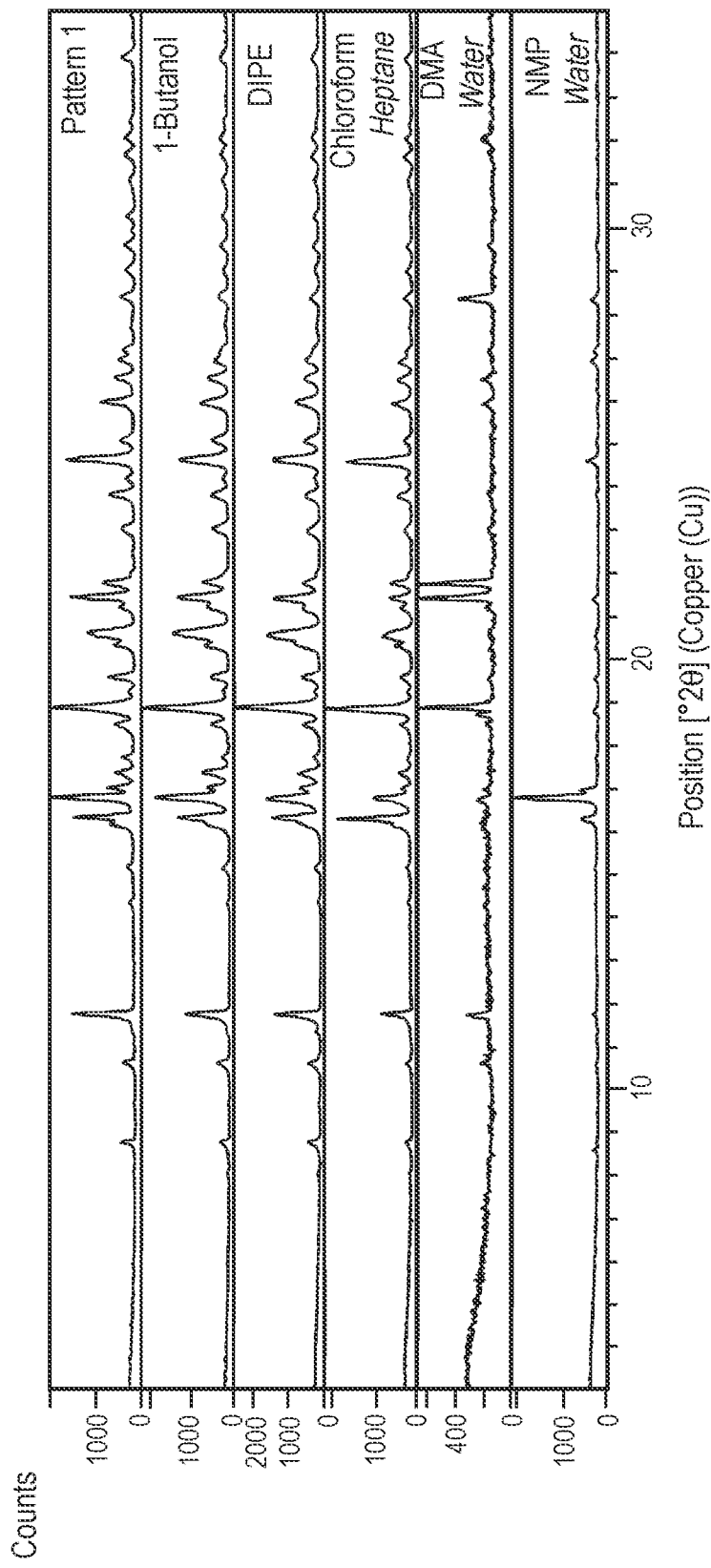
FIG. 14*a* to FIG. 14*e*. display X-Ray Powder Diffraction (XRPD) patterns of Crystalline Form 1 of ralinepag obtained from the post-thermal cycling and drying in a vacuum oven at 40° C. in Example 4. All figures display a reference X-Ray Powder Diffraction (XRPD) pattern of Form 1 at the top. XRPD patterns marked with a (PO) correspond to preferred orientations.
Figure 14B:
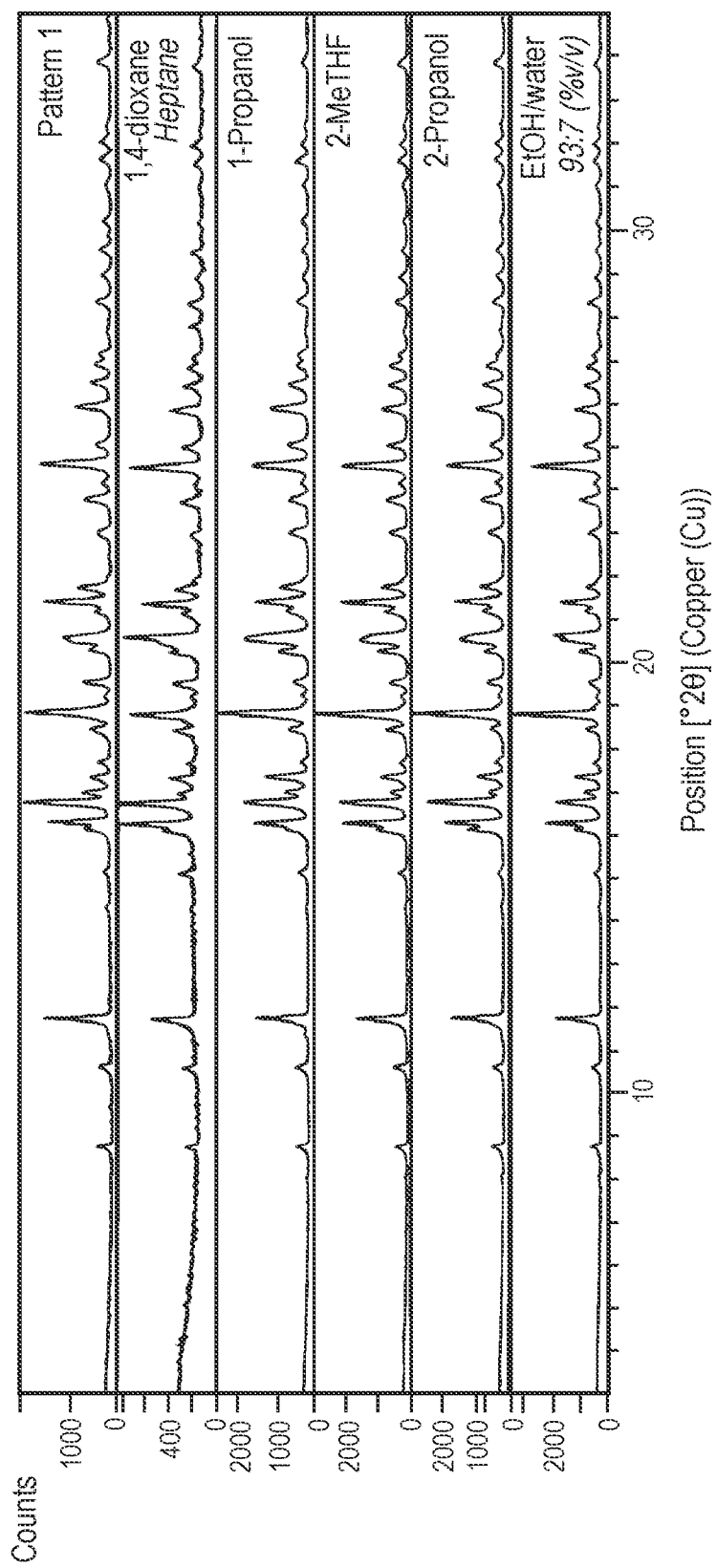
Figure 14C:
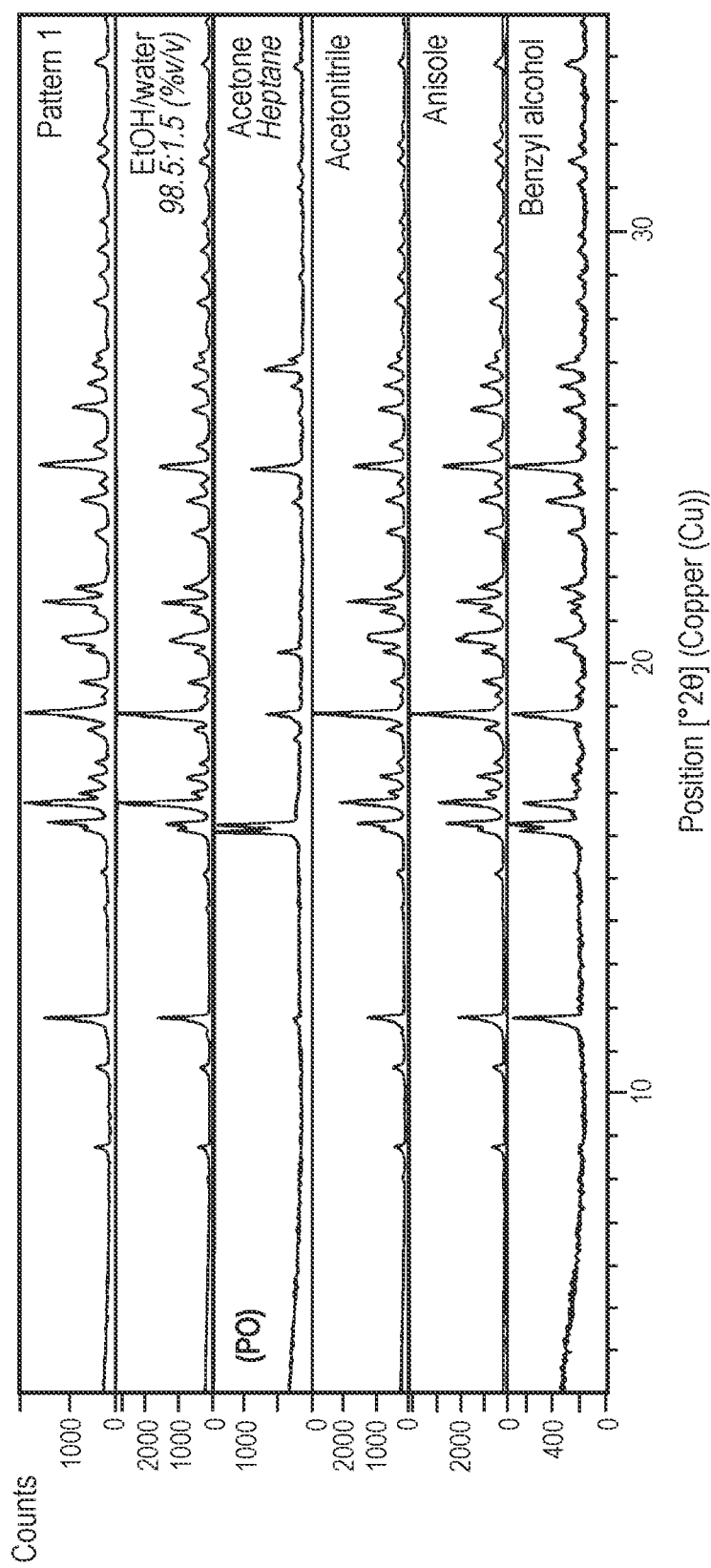
Figure 14D:
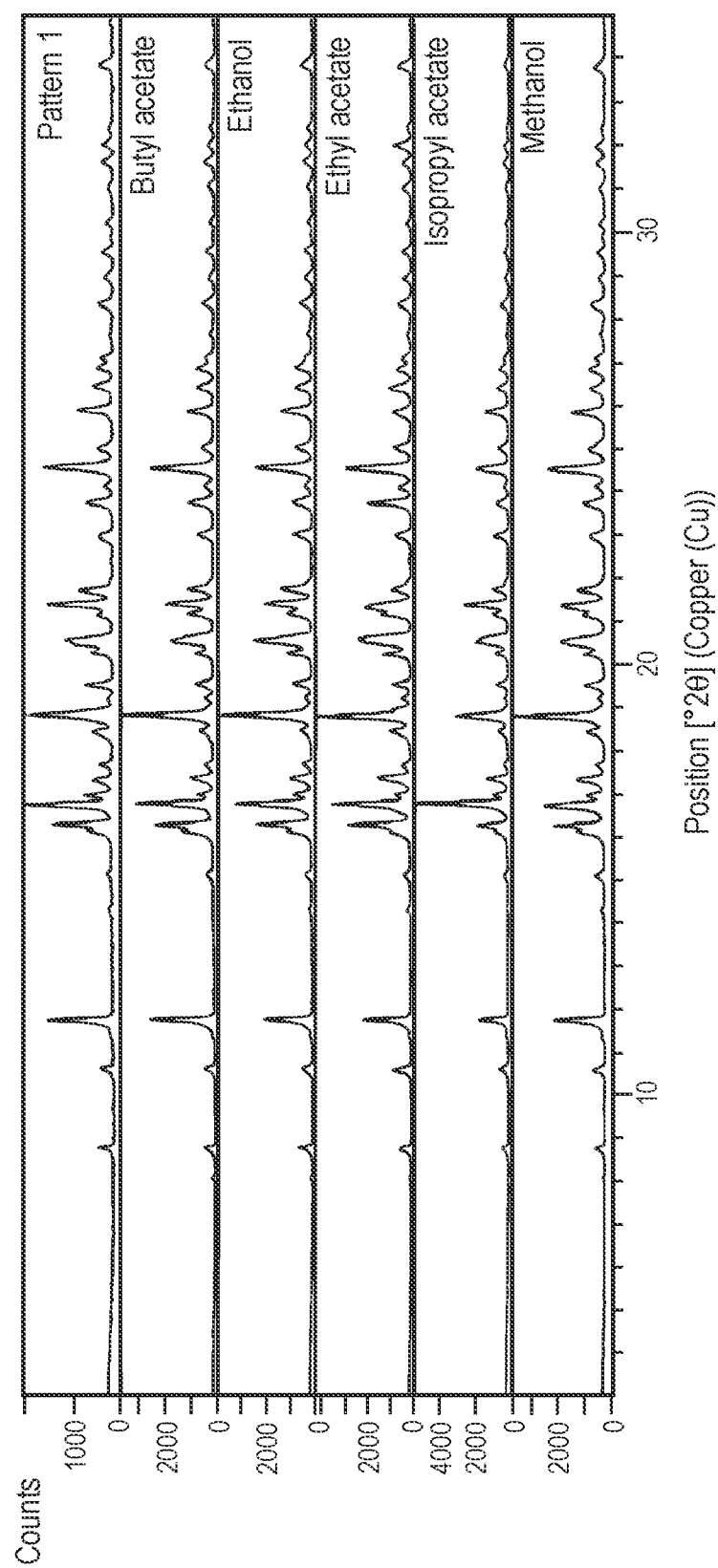
Figure 14E:
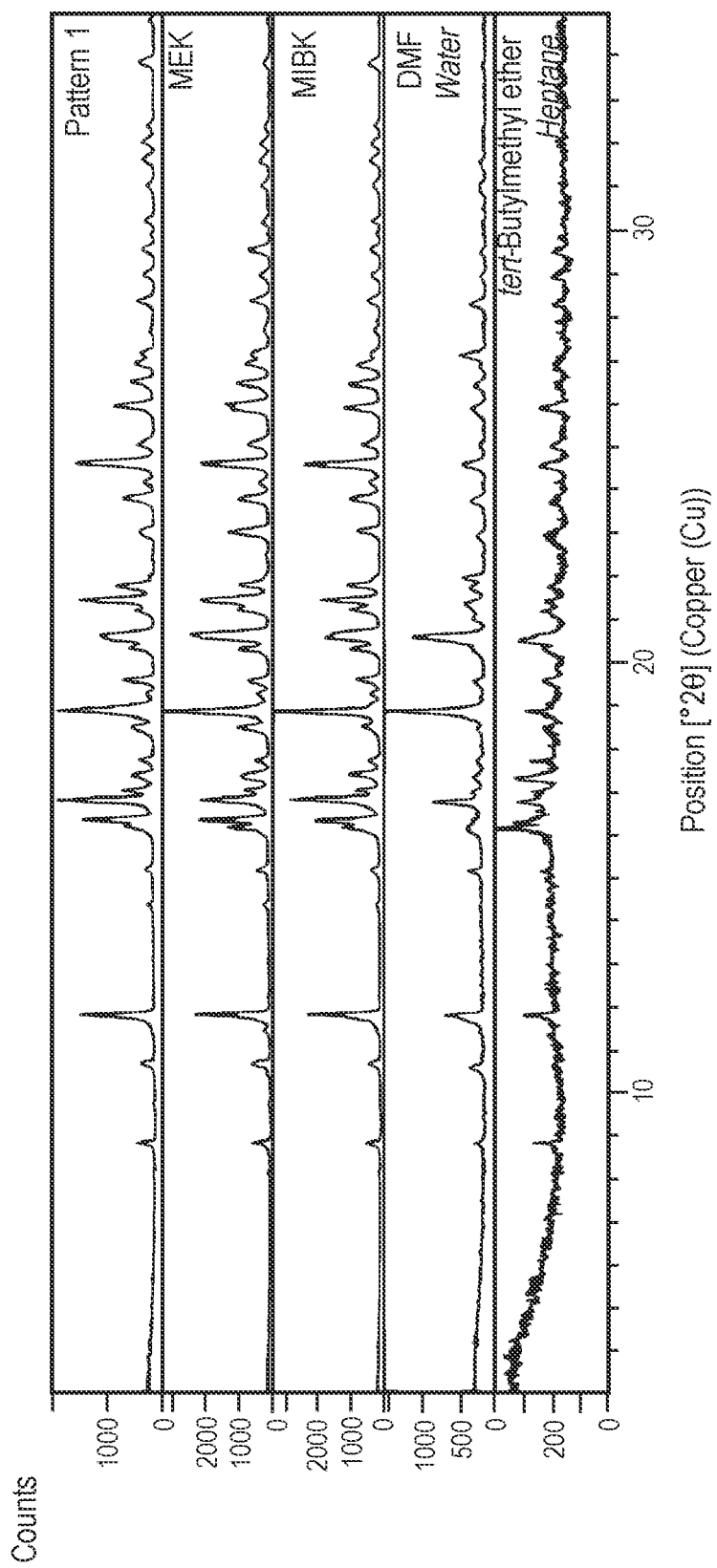
Figure 14F:
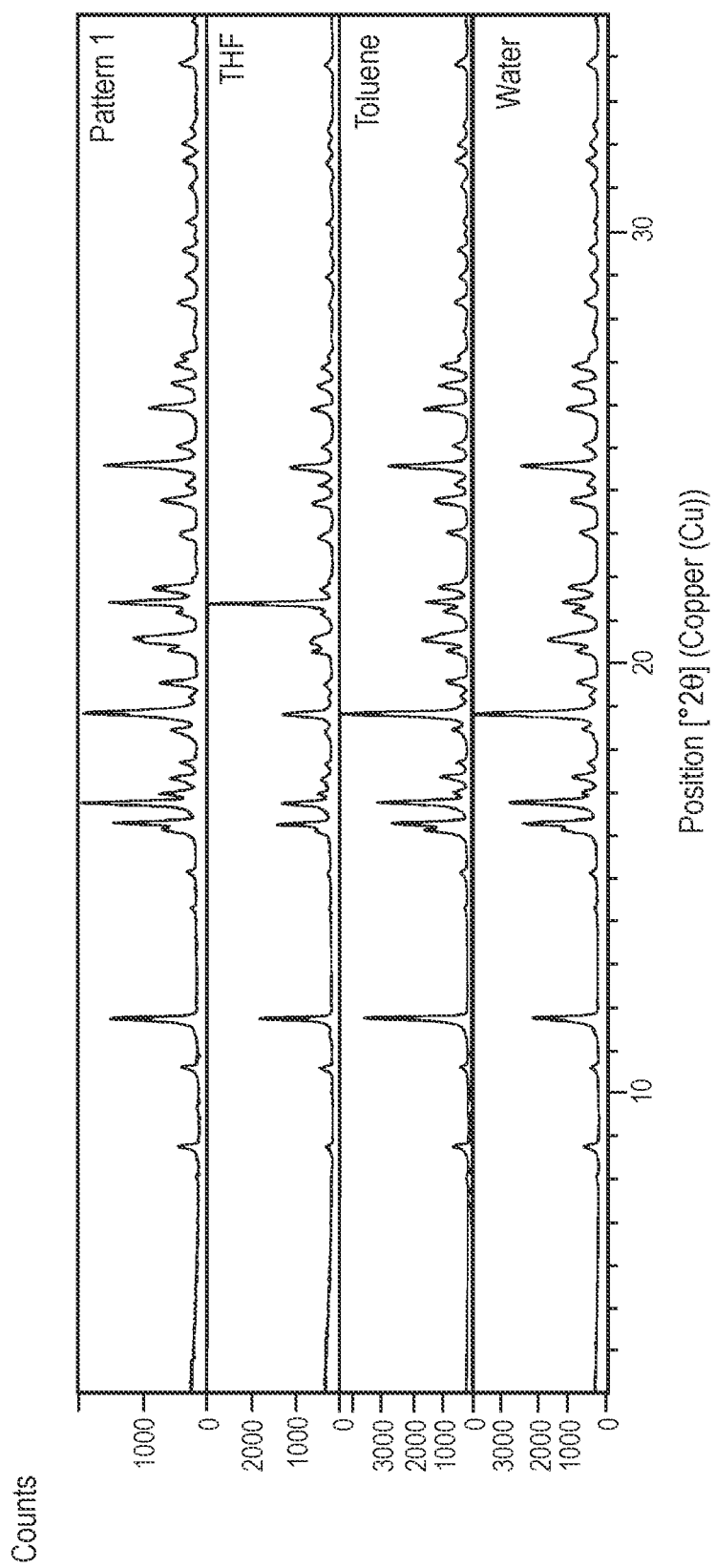
FIG. 14*f* displays X-Ray Powder Diffraction (XRPD) patterns of Crystalline Form 1 of ralinepag post-thermal cycling. Only Form 1 was recovered in all samples when dried.
Figure 14G:
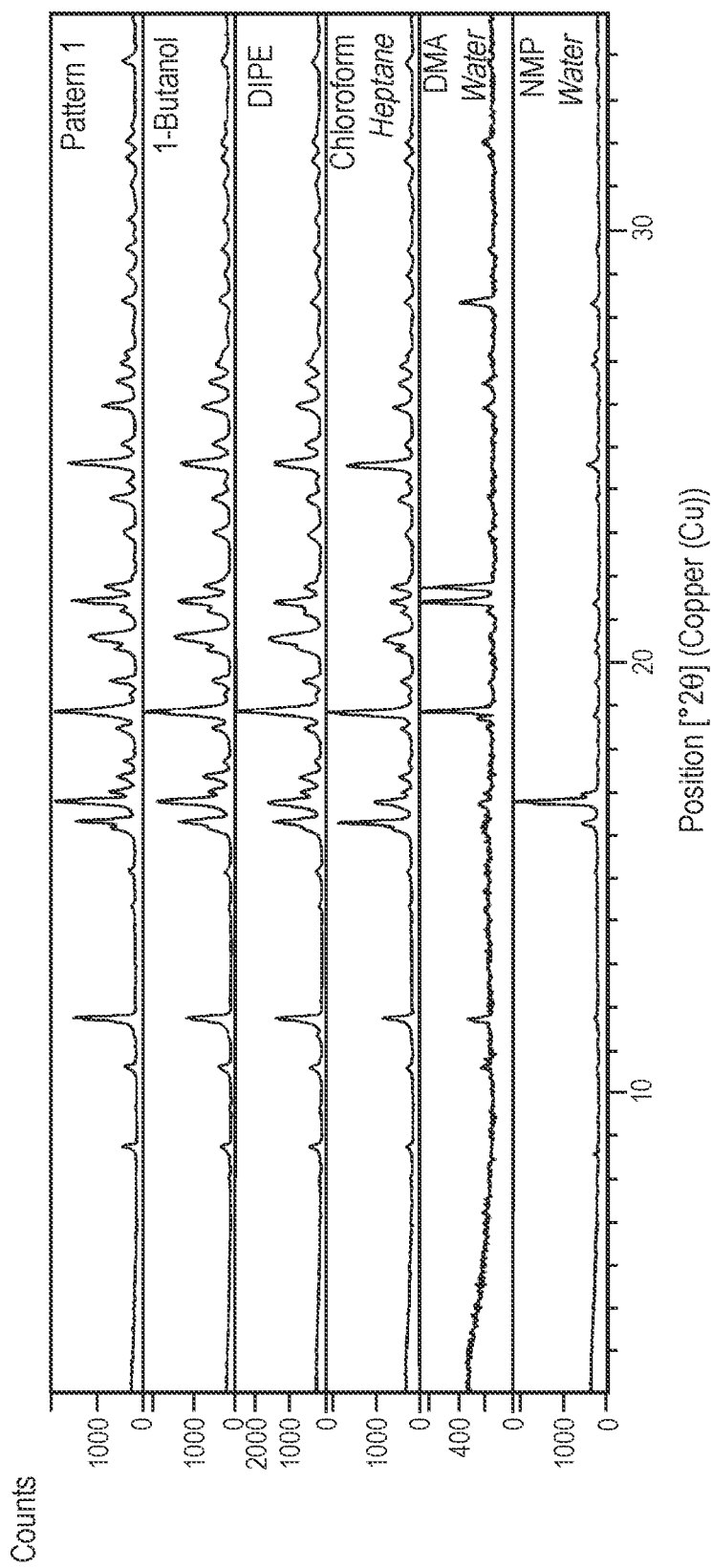
FIG. 14*g* displays X-Ray Powder Diffraction (XRPD) patterns of Crystalline Form 1 of ralinepag post-thermal cycling. Form 1 was produced from 3 out of 5 solids recovered post-thermal cycling. The form was retained on drying. Amorphous solids from DMA/water and NMP/water were found to dry to Form 1.
Figure 15A:
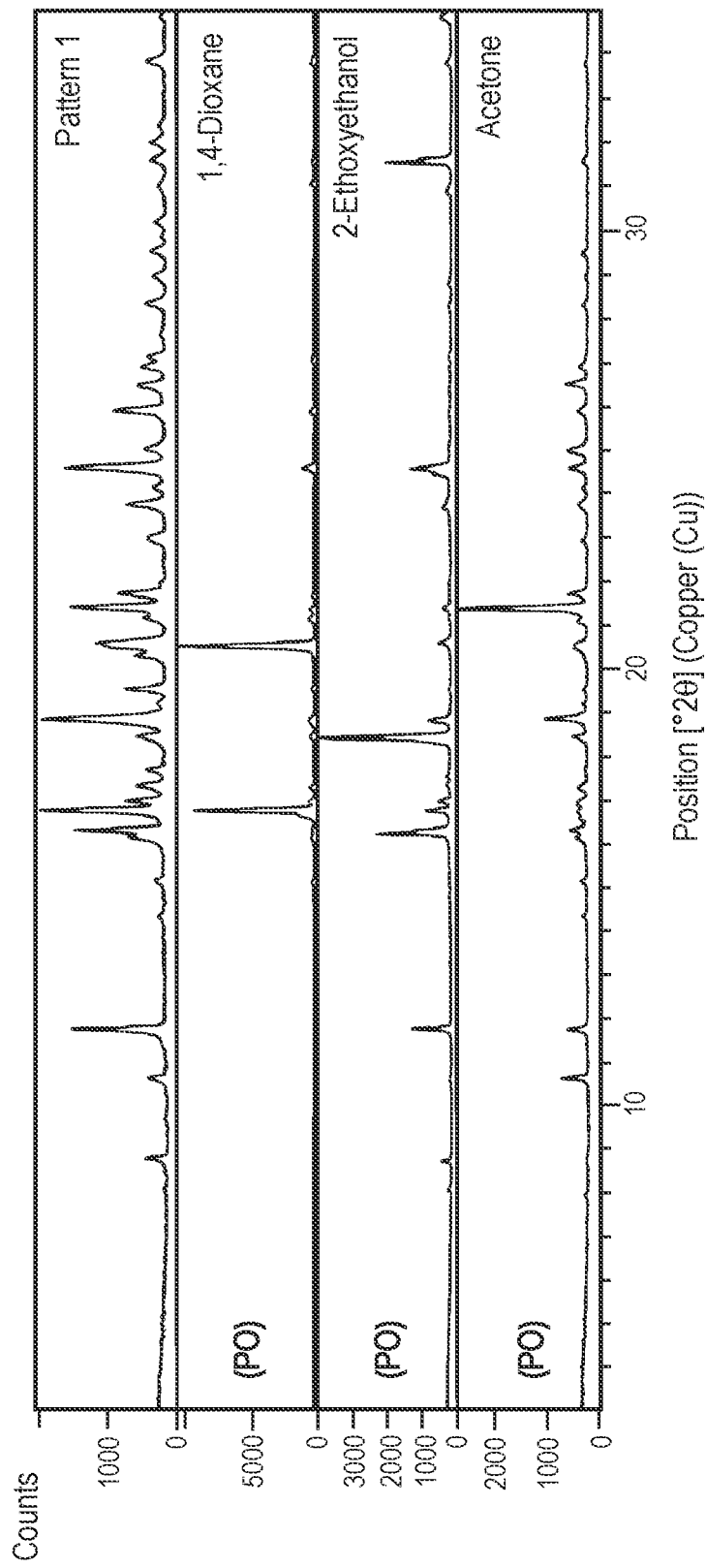
FIG. 15*a* to FIG. 15*c*. display X-Ray Powder Diffraction (XRPD) patterns of Crystalline Form 1 of ralinepag obtained after evaporation of the mother liquors in Example 4. (The last sample depicted was obtained after anti-solvent addition of the mother liquor in Example 4). All figures display a reference X-Ray Powder Diffraction (XRPD) pattern of Form 1 at the top. XRPD patterns marked with a (PO) correspond to preferred orientations.
Figure 15B:
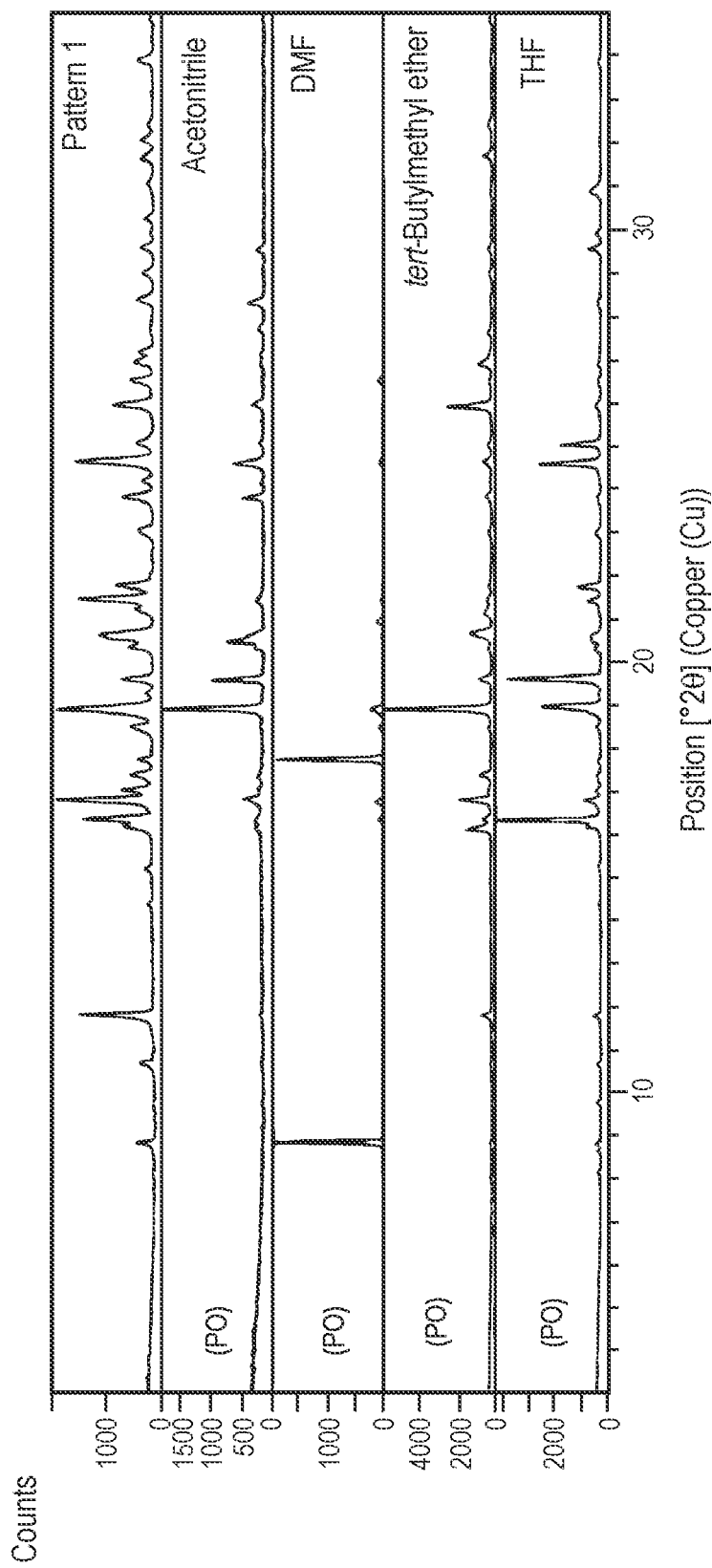
Figure 15C:
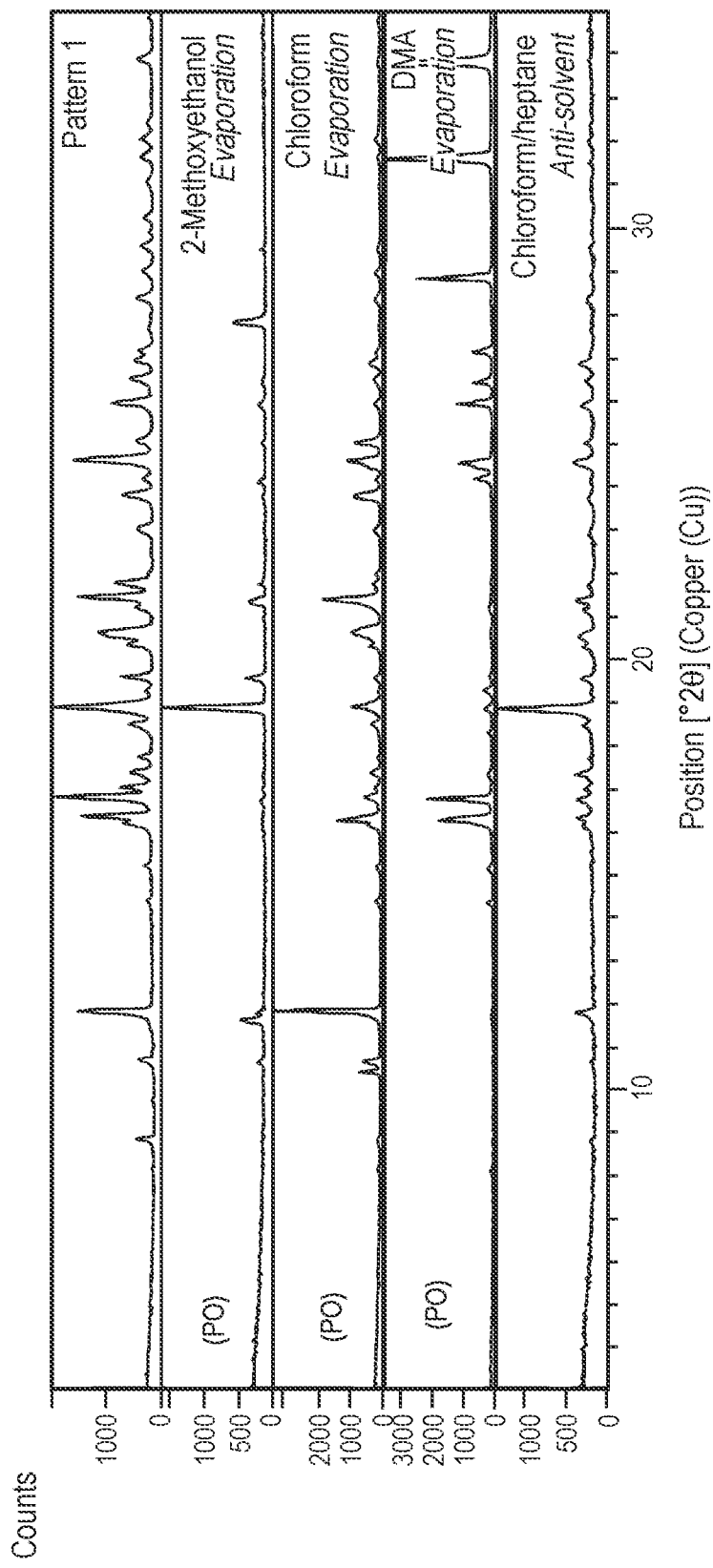
Figure 16:
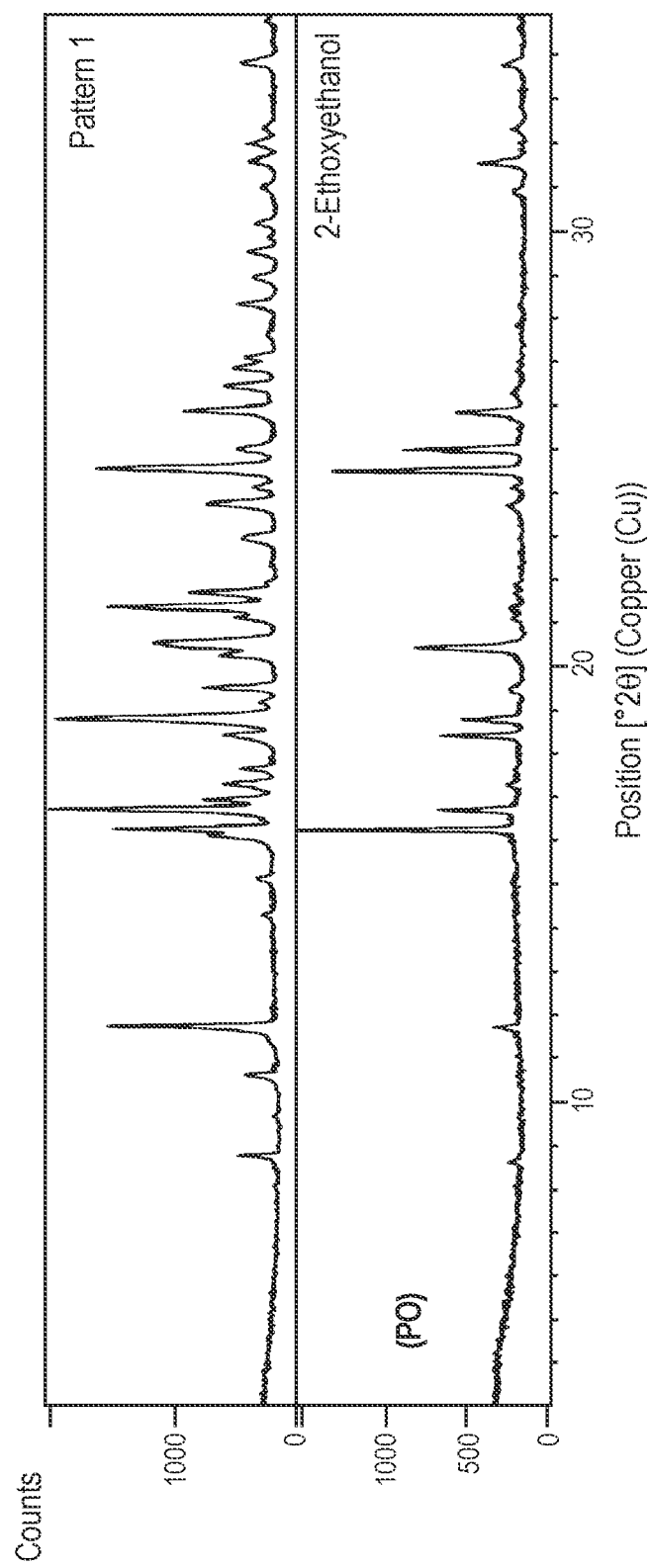
FIG. 16. displays X-Ray Powder Diffraction (XRPD) patterns isolated Crystalline Form 1 of ralinepag obtained after crash cooling of the mother liquors in Example 4. All figures display a reference X-Ray Powder Diffraction (XRPD) pattern of Form 1 at the top. XRPD patterns marked with a (PO) correspond to preferred orientations.
Figure 17A:
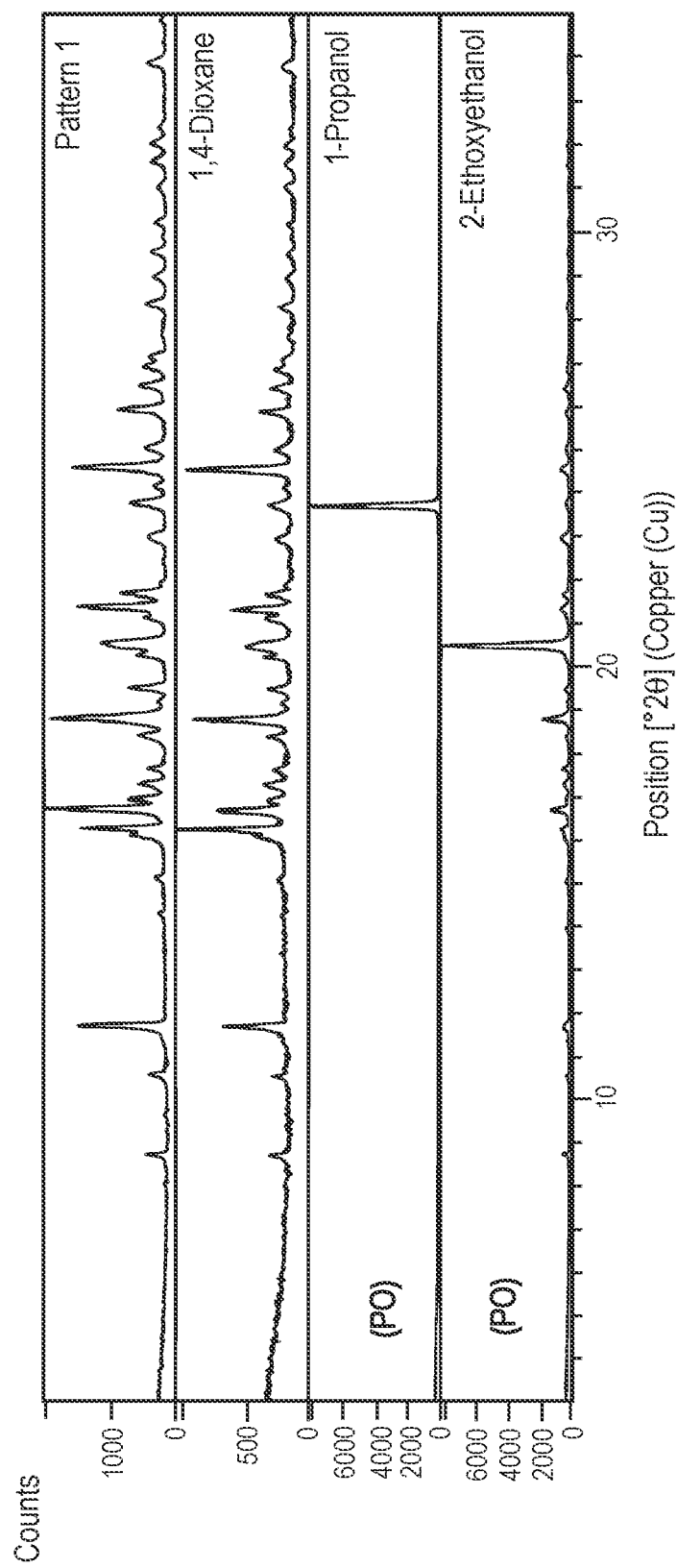
FIG. 17*a* and FIG. 17*b*. display X-Ray Powder Diffraction (XRPD) patterns of Crystalline Form 1 of ralinepag obtained after anti-solvent addition of the mother liquors in Example 4. All figures display a reference X-Ray Powder Diffraction (XRPD) pattern of Form 1 at the top. XRPD patterns marked with a (PO) correspond to preferred orientations.
Figure 17B:
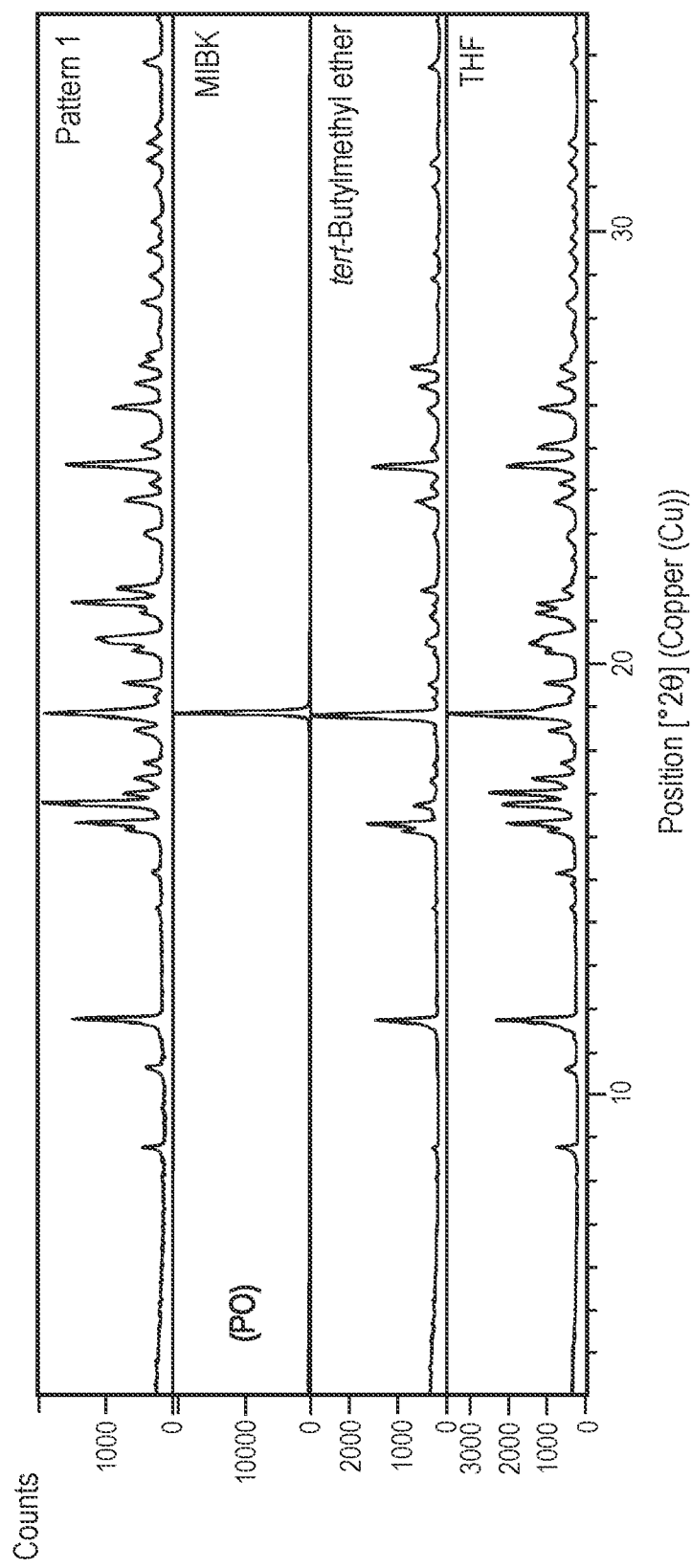

*poor crystallinity;
**anti-solvent added;
Am. = amorphous;
n.s. = no solid recovered;
†preferred orientation Thermal Cycling Post-thermal cycling, only Form 1 was recovered (or amorphous materials containing Form 1 peaks), with the exception of N,N-dimethylacetamide/water and N-methyl-2-pyrrolidone/water mixtures, which produced amorphous material. See FIG. 14f and FIG. 14g. All Form 1 solids appeared to be highly crystalline with slight reductions in crystallinity noted in the solids recovered from N,N-dimethylformamide, tert-butyl methyl ether, and water.

Form 1 was recovered in all samples when dried. Several solids which were amorphous/predominantly amorphous when wet, dried to Form 1, for example, solids from 2-methyl-tetrahydrofuran, benzyl alcohol, toluene, N,N-dimethylacetamide/water, and N-methyl-2-pyrrolidone/water.

Evaporation

All samples which produced solids on evaporation provided Form 1, with the exception of dimethylsulfoxide, which provided Form 3.

Crash Cooling

Only 2-ethoxyethanol (Form 1) and acetone (amorphous with some Form 1 peaks) provided solids on crash cooling.

Anti-Solvent Addition

The solids isolated from 1,4-dioxane/heptane, 1-propano/heptane, 2-ethoxyethanol/heptane, dimethylsulfoxide/water, methyl isobutyl ketone/heptane, N,N-dimethylformamide/water, tert-butyl methyl ether/heptane, tetrahydrofuran/heptane, toluene/heptane, and chloroform/heptane provided Form 1. Amorphous material was obtained from 2-methyl-tetrahydrofuran/heptane, ethanol/water, acetone/heptane, acetonitrile/water, butyl acetate/heptane, ethanol/heptane, and ethyl acetate/heptane.

A new pattern was recovered from N,N-dimethylacetamide and N-methyl-2-pyrrolidone when water was added as an anti-solvent, Pattern 4. Upon drying, Form 1 was produced from Pattern 4. To carry out analysis of Pattern 4, another sample was prepared from N-methyl-2-pyrrolidone/water.

The manner of sample preparation can impact relative intensities of the peaks. That is, many of the sample preparations of Crystalline Form 1 displayed a preferred orientation, including:
  samples prepared by thermal cycling of acetone;
  all samples prepared by solvent evaporation; and
  samples prepared by anti-solvent addition of 1-propanol/heptane, 2-ethoxyethanol/heptane, and methyl isobutyl ketone/heptane.

Example 5: X-Ray Powder Diffraction (XRPD)

Although the following diffractometers were used, other types of diffractometers can be used. Furthermore, other wavelengths can be used and converted to the Cu Kα. In some embodiments, Synchrotron Radiation X-Ray Powder Diffraction (SR-XRPD) can be used to characterize the crystalline forms.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2°2-Theta.

XRPD analysis was carried out on a PANalytical X'pert pro with PIXcel detector (128 channels), scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation (α1 λ=1.54060 Å; α2=1.54443 Å; β=1.39225 Å; α1:α2 ratio=0.5) running in transmission mode (step size 0.0130° 2θ, step time 18.87 s) using 40 kV/40 mA generator settings.

Data were visualized and images generated using the HighScore Plus 4.7 desktop application (PANalytical, 2017).

For samples with only one XRPD pattern and no other means to evaluate whether the sample provides a good approximation of the powder average, peak tables contain data identified only as "Prominent Peaks." These peaks are a subset of the entire observed peak list. Prominent peaks are selected from observed peaks by identifying preferably non-overlapping, low-angle peaks, with strong intensity.

Characterization of Crystalline Form 1 of Ralinepag

The X-Ray powder diffraction pattern for Crystalline Form 1 of ralinepag is displayed in FIG. 1. Representative peaks include the peaks listed in the following table:

| Angle 2-Theta (°) | Rel. Intensity [%] |
|---|---|
| 8.8 | 17.56 |
| 11.7 | 72.81 |
| 16.1 | 27.95 |
| 16.2 | 70.90 |
| 16.7 | 100.00 |
| 18.8 | 91.82 |
| 20.4 | 44.58 |
| 20.5 | 54.04 |
| 21.3 | 74.49 |
| 24.5 | 78.44 |
| 25.8 | 41.18 |
| 33.8 | 16.18 |

Characteristic peaks of Crystalline Form 1 of ralinepag can include 8.8±0.2°2-Theta, 11.7±0.2°2-Theta, 16.2±0.2°2-Theta, 21.3±0.2°2-Theta, and 33.8±0.2°2-Theta. Characteristic peaks of Crystalline Form 1 of ralinepag can include peaks at 8.8±0.2°2-Theta, 11.7±0.2°2-Theta, and 16.2±0.2°2-Theta.

The manner of sample preparation can impact relative intensities of the peaks. For example, as described in Example 4, all samples prepared via solvent evaporation, and many samples prepared by other methods, displayed a preferred orientation. Additional X-Ray powder diffraction patterns obtained from isolated crystalline Form 1 of ralinepag throughought the examples described herein are displayed in FIG. 12a to FIG. 12f, FIG. 13a to FIG. 13e, FIG. 14a to FIG. 14e, FIG. 15a to FIG. 15c, FIG. 16, FIG. 17a and FIG. 17b. These additional patterns show the variation in the XRPD pattern of crystalline Form 1 of ralinepag obtained throughout the examples herein.

If multiple diffraction patterns are available, then assessments of particle statistics (PS) and/or preferred orientation (PO) are possible. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks.".

The term "preferred orientation" as used herein refers to an extreme case of non-random distribution of the crystallites of a solid state form. In XRPD, the ideal sample is homogenous and the crystallites are randomly distributed in the bulk solid. In a truly random sample, each possible reflection from a given set of planes will have an equal number of crystallites contributing to it. However, when the solid state form is in a preferred orientation this is not the case. Accordingly, comparing the intensity between a randomly oriented diffraction pattern and a preferred oriented diffraction pattern can look entirely different. Quantitative analysis depending on intensity ratios are greatly distorted by preferred orientation.

Characterization of Crystalline Pattern 2 of Ralinepag

The X-Ray powder diffraction pattern for Crystalline Pattern 2 of ralinepag is displayed in FIG. 2. Representative peaks include the peaks listed in the following table:

| Angle 2-Theta (°) | Rel. Intensity [%] |
|---|---|
| 4.1 | 31.97 |
| 15.5 | 30.35 |
| 16.9 | 95.99 |
| 17.9 | 100.00 |
| 18.8 | 54.17 |
| 21.6 | 57.14 |
| 22.8 | 74.31 |
| 23.7 | 66.02 |

Pattern 2 was recovered only post-lyophilization from tert-butanol and 1,4-dioxane and is a poorly crystalline form.

Pattern 2 converts to Form 1 on heating.

Characterization of Crystalline Form 3 of Ralinepag

The X-Ray powder diffraction pattern for Crystalline Form 3 of ralinepag is displayed in FIG. 3. Representative peaks include the peaks listed in the following table:

| Angle 2-Theta (°) | Rel. Intensity [%] |
|---|---|
| 3.6 | 29.06 |
| 18.7 | 100.00 |
| 20.9 | 39.98 |
| 22.2 | 52.81 |
| 24.2 | 69.93 |
| 24.3 | 75.28 |

Form 3 was recovered only from DMSO, and is highly crystalline.

Characterization of Crystalline Pattern 4 of Ralinepag

The X-Ray powder diffraction pattern for Crystalline Pattern 4 of ralinepag is displayed in FIG. 4. Representative peaks include the peaks listed in the following table:

| Angle 2-Theta (°) | Rel. Intensity [%] |
|---|---|
| 15.0 | 38.08 |
| 16.7 | 100.00 |
| 18.0 | 73.16 |
| 18.7 | 48.43 |
| 18.9 | 75.35 |
| 22.6 | 53.51 |
| 22.7 | 42.43 |
| 24.5 | 33.19 |

Pattern 4 was observed only in wet solids obtained from N,N-dimethylacetamide (DMA) and N-methyl-2-pyrrolidone (NMP) when water was added as a cosolvent.

Pattern 4 made from NMP/water converts to Form 1 upon drying (even with air drying).

Pattern 4 made from DMA/water converts to a predominantly amorphous form with some Form 1 peaks present.

Characterization of Amorphous Ralinepag

Figure 5:
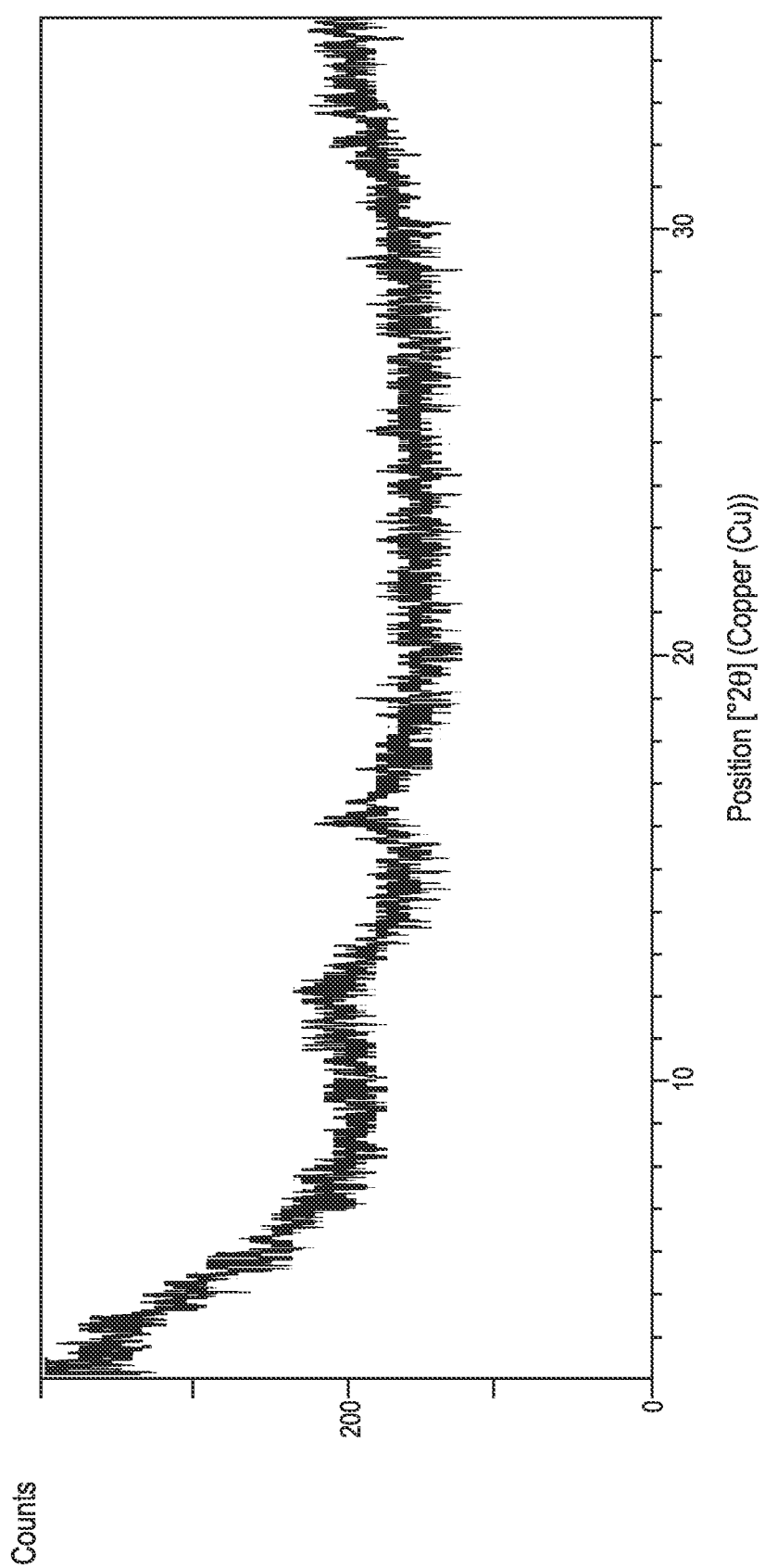
FIG. 5. displays the X-Ray Powder Diffraction (XRPD) pattern of amorphous ralinepag.

The X-Ray powder diffraction pattern for Amorphous of ralinepag, as prepared in Example 2f, is displayed in FIG. 5. The XRPD shows a lack of crystallinity.

Example 6: Thermogravimetric/Differential Thermal Analysis (TGA/DTA)

Approximately, 5 mg of material was weighed into an open aluminum pan and loaded into a simultaneous thermogravimetric/differential thermal analyzer (TGA/DTA) and held at room temperature. The sample was then heated at a rate of 10° C./min from 20° C. to 350° C. during which time the change in sample weight was recorded along with any differential thermal events (DTA). Nitrogen was used as the purge gas, at a flow rate of 300 cm$^3$/min.

The TGA/DTA thermogram for Crystalline Form 1 of ralinepag is displayed in FIG. 6. The TGA/DTA thermogram for Crystalline Pattern 2 of ralinepag is displayed in FIG. 8. The TGA/DTA thermogram for Crystalline Form 3 of ralinepag is displayed in FIG. 9. The TGA/DTA thermogram for Crystalline Pattern 4 of ralinepag is displayed in FIG. 10.

Thermogravimetric/Differential Thermal Analysis (TGA/DTA) patterns for the ralinepag solid state forms are as described in the following table.

TABLE 4

Representative TGA/DTA patterns

| Solid State Form | TGA Trace | DTA Thermogram |
| --- | --- | --- |
| Form 1 | no significant loss in mass prior to decomposition above approx. 235° C. | endothermic event (onset at 127.2° C.; peak at 129.5° C.) |
| Pattern 2 | no significant loss in mass prior to decomposition above approx. 250° C. | weak endothermic and exothermic events from 81 to 89° C.; broad endothermic event (onset at 124.7° C.; peak at 127.3° C.) |
| Form 3 | mass loss of 17.8% from the onset of heating up to approx. 238° C.; decomposition observed above 267° C. | sharp endothermic event (onset at 74.6° C.; peak at 78.9° C.) |
| Pattern 4 | significant loss in mass (21.6%) prior to melting*; decomposition observed above 300° C. | broad endothermic event (onset at 29.0° C.; peak at 64.0° C.)*; sharp endothermic event (onset at 127.8° C.; peak at 130.5 |

*sample not dried prior to TGA/DTA analysis

Example 7: Differential Scanning Calorimetry (DSC)

To assess the possibility of recrystallisation, Crystalline Form 1 of ralinepag was heated beyond the melting point before being cooled back to 20° C. and subsequently re-heated.

Approximately, 1-5 mg of material was weighed into an aluminium DSC pan and sealed nonhermetically with an aluminium lid. The sample pan was then loaded into a TA Instruments Discovery DSC 2500 differential scanning calorimeter equipped with a RC90 cooler. The sample and reference were heated above the melting temperature at a scan rate of 10° C./min and the resulting heat flow response was monitored. The sample was re-cooled to 20° C. and then reheated again beyond melting at 10° C./min. Nitrogen was used as the cell purge gas, at a flow rate of 50 cm$^3$/min.

The DSC thermogram for Crystalline Form 1 of ralinepag is displayed in FIG. 7. A sharp endothermic event consistent with the melt onset in the TGA/DTA was observed in the first heating step (onset at about 127.5° C.; peak at about 129.2° C.). No further events observed in the first heating step. No thermal events were observed on cooling post-melting. A weak thermal event was observed at approximately 193° C. in the second heating step, potentially due to onset of decomposition.

Example 8: Dynamic Vapour Sorption (DVS)

Approximately, 10 mg of sample was placed into a mesh vapor sorption balance pan and loaded into a DVS-1/DVS Intrinsic/DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 min, maximum step length 500 min) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined.

Crystalline Form 1 of ralinepag is non-hygroscopic. Reversible water uptake for crystalline Form 1 as determined by DVS was 0.1% (w/w) between 0% and 90% RH.

XRPD analysis was then carried out on any solid retained, and indicated that the material was unchanged after DVS analysis, remaining as Crystalline Form 1.

Example 9: High Performance Liquid Chromatography-Ultraviolet Detection (HPLC-UV)

Purity analysis was performed using HPLC. The full method details are provided below:

| Parameter | Value | | |
| --- | --- | --- | --- |
| Column | Waters XBridge BEH Shield RP18 150 × 4.6 mm, 2.5 µm | | |
| Column Temperature (° C.) | 40 | | |
| Autosampler Temperature (° C.) | ambient | | |
| Wavelength, Bandwidth (nm) | 240 | | |
| Injection Volume (µL) | 7 | | |
| Flow Rate (mL/min) | 1.0 | | |
| Mobile Phase A | 0.02% ammonia in water | | |
| Mobile Phase B | acetonitrile | | |
| Timetable | Time (min) | % Phase A | % Phase B |
| | 0.0 | 95 | 5 |
| | 1.0 | 95 | 5 |
| | 10.0 | 60 | 40 |
| | 15.0 | 15 | 85 |

-continued

| | | |
|---|---|---|
| 17.0 | 5 | 95 |
| 19.0 | 5 | 95 |
| 19.1 | 95 | 5 |
| 25.0 | 95 | 5 |

Crystalline Form 1 of ralinepag was determined to be 99.7% pure by relative area.

Example 10: Single Crystal X-Ray Diffraction (SXRD) of Crystalline Form 1 of Ralinepag Crystalline Form 1 of ralinepag from isopropyl acetate when heptane was added as an anti-solvent consisted of very large lath-like particles. The particles appeared birefringent under polarized light, consistent with a crystalline material.

A suitable crystal was elected and mounted in a loop using paratone oil. Data were collected using a Bruker D8 Venture diffractometer equipped with a Photon III detector operating in shutterless mode at 100(2) K with Cu-Kα radiation (1.54178 Å). The structure was solved in the Olex2 software package (Dolomanov, O. V., Bourhis, L. J., Gildea, R. J, Howard, J. A. K. & Puschmann, H. *J. Appl. Cryst.*, 2009, 42, 339-341.) with the ShelXT (intrinsic phasing) (Sheldrick, G. M. *Acta Cryst.*, 2015, A71, 3-8.) structure solution program and refined with the ShelXL (Sheldrick, G. M. *Acta Cryst.*, 2015, C71, 3-8.) refinement package using Least Squares minimisation. Data were collected, solved and refined in the triclinic space-group P-1.

All non-hydrogen atoms were located in the Fourier map and their positions refined prior to describing the thermal movement of all non-hydrogen atoms anisotropically. Within the asymmetric unit, one complete ralinepag formula unit was refined. All hydrogen atoms were placed in calculated positions using a riding model with fixed Uiso at 1.2 times for all CH and CH$_2$ groups, and 1.5 times for all OH groups.

The highest residual Fourier peak was found to be 0.79 e·Å$^{-3}$ approx. 0.68 Å from Cl(1A) and the deepest Fourier hole was found to be −0.43 e·Å$^{-3}$ approx. 0.52 Å from Cl(1A).

The asymmetric unit was found to contain only one complete molecule of ralinepag.

The crystallographic parameters and refinement indicators were found to be as follows:

Crystal Data of Crystalline Form 1 of Ralinepag at 100K

| | |
|---|---|
| Empirical formula | C$_{23}$H$_{26}$ClNO$_5$ |
| Formula weight | 431.90 |
| Temperature (K) | 100.0 |
| Crystal system | triclinic |
| Space group | P-1 |
| a (Å) | 10.1269(9) |
| b (Å) | 10.7838(8) |
| c (Å) | 11.1906(8) |
| α (°) | 80.888(3) |
| β (°) | 71.953(3) |
| γ (°) | 68.331(4) |
| Volume (Å$^3$) | 1078.51(15) |
| Z, Z' | 2, 1 |
| Calculated Density (g/cm$^3$) | 1.330 |
| Absorption coefficient (mm$^{-1}$) | 1.858 |
| F(000) | 456.0 |
| Crystal size (mm$^3$) | 0.16 × 0.16 × 0.14 |
| Radiation | CuKα (λ = 1.54178) |
| 2 Θ range for data collection (°) | 8.32 to 144.78 |
| Index ranges | −12 ≤ h ≤ 12, −13 ≤ k ≤ 13, −13 ≤ l ≤ 13 |
| Reflections collected | 72049 |
| Independent reflections | 4253 [R$_{int}$ = 0.0415, R$_{sigma}$ = 0.0160] |
| Data/restraints/parameters | 4253/0/275 |
| S | 1.118 |
| Final R indexes [F$^2$ > 2σ (F$^2$)] | R$_1$ = 0.0471, wR$_2$ = 0.1030 |
| Final R indexes [all data] | R$_1$ = 0.0475, wR$_2$ = 0.1032 |
| Δρmax, Δρmin (e Å$^{-3}$) | 0.79/−0.43 |

$R_1 = (\Sigma |F_o| − |F_c|)/\Sigma |F_o|)$
$wR_2 = \{\Sigma [w(F_o^2 − F_c^2)^2]/\Sigma [w(F_o^2)^2]\}^{1/2}$
$S = \{\Sigma [w(F_o^2 − F_c^2)^2]/(n − p)\}^{1/2}$ Fractional Atomic Coordinates for Crystalline Form 1 of Ralinepag at 100K

| Atom | x | y | z |
|---|---|---|---|
| Cl1 | −4187.5(6) | 10554.2(6) | 8422.0(7) |
| O1 | 13336.3(14) | 1059.1(12) | 5066.3(13) |
| O2 | 14028.7(14) | −1175.8(12) | 5278.2(13) |
| O3 | 10406.6(13) | 1265.0(12) | 5619.4(12) |
| O4 | 4317.8(13) | 6561.9(12) | 8015.1(13) |
| O5 | 2743.1(14) | 8690.2(12) | 8287.0(13) |
| N1 | 1964.4(16) | 7001.0(14) | 8116.5(14) |
| C1 | 13046.5(19) | 31.9(18) | 5255.3(16) |
| C2 | 11519.8(19) | −2.1(18) | 5466.7(19) |
| C3 | 10056(2) | 1744.5(19) | 6842.3(17) |
| C4 | 8646.2(19) | 2946.8(18) | 7056.3(17) |
| C5 | 8141(2) | 3307.8(19) | 8431.2(17) |
| C6 | 6728(2) | 4522.4(19) | 8707.8(17) |
| C7 | 6898(2) | 5728.9(18) | 7840.2(17) |
| C8 | 7417(2) | 5375.9(19) | 6464.2(18) |
| C9 | 8828(2) | 4155.3(19) | 6196.9(18) |
| C10 | 5501(2) | 6946.9(19) | 8126.9(19) |
| C11 | 2993.7(19) | 7528.9(18) | 8150.8(16) |
| C12 | 2368.6(19) | 5610.1(17) | 7897.2(17) |
| C13 | 3218(2) | 5115(2) | 6731.8(19) |
| C14 | 3575(3) | 3775(2) | 6541(2) |
| C15 | 3067(2) | 2957(2) | 7505(2) |
| C16 | 2221(2) | 3454(2) | 8667(2) |
| C17 | 1865(2) | 4792(2) | 8869.3(19) |
| C18 | 457.1(19) | 7828.0(17) | 8255.8(17) |
| C19 | −306(2) | 8730.7(17) | 9200.6(17) |
| C20 | −1755(2) | 9549.2(18) | 9284.5(18) |
| C21 | −2430(2) | 9449.8(19) | 8421(2) |
| C22 | −1705(2) | 8522.3(19) | 7506.0(19) |
| C23 | −258(2) | 7711.2(19) | 7423.3(17) |
| Cl1A | 3759(6) | 1183(6) | 7725(6) |

Hydrogen Atom Coordinates for Crystalline Form 1 of Ralinepag at 100K

| Atom | x | y | z |
|---|---|---|---|
| H2 | 14866.39 | −1119.59 | 5156.22 |
| H2A | 11501.26 | −409.4 | 4741.57 |
| H2B | 11297.39 | −581.1 | 6226.19 |
| H3A | 10875.53 | 1996.6 | 6908.74 |
| H3B | 9926.79 | 1029.77 | 7493.85 |
| H4 | 7864.51 | 2700.29 | 6884.7 |
| H5A | 7968.77 | 2535.94 | 8980.8 |
| H5B | 8933.23 | 3496.95 | 8629.71 |
| H6A | 5907.98 | 4299.39 | 8600.63 |
| H6B | 6471.15 | 4750.47 | 9593.14 |
| H7 | 7695.2 | 5956.32 | 8007.09 |
| H8A | 7600 | 6147.48 | 5920.94 |
| H8B | 6628.42 | 5193.72 | 6252.8 |
| H9A | 9095.04 | 3930.04 | 5309.26 |
| H9B | 9644.89 | 4373.32 | 6315.81 |
| H10A | 5283.63 | 7226.2 | 8988.44 |
| H10B | 5619.45 | 7700.8 | 7522.6 |
| H13 | 3554.07 | 5686.84 | 6067.1 |
| H14 | 4168.96 | 3422.88 | 5746.97 |
| H15 | 3299.76 | 2043.32 | 7368.84 |
| H16 | 1882.22 | 2881.73 | 9329.84 |

-continued

| Atom | x | y | z |
|---|---|---|---|
| H17 | 1280.91 | 5139.29 | 9667.11 |
| H19 | 165.47 | 8788.1 | 9792.88 |
| H20 | −2276.03 | 10170.76 | 9927.98 |
| H22 | −2194.72 | 8440.98 | 6938.12 |
| H23 | 249.1 | 7071.88 | 6794.4 |

The structure was observed to have efficient packing with a calculated density of 1.330 g/cm$^3$ and no regions of spurious electron density that could be attributed to solvent nor any large voids or channels within which solvent or water could reside. The packing can be seen when viewed along unit cell axes a, b and c. A strong hydrogen bonding interaction was observed between opposite carboxylic acid termini, providing the drive for crystallization of ralinepag: O(1) . . . H(2)–O(2)=1.78355(16) Å.

Figure 11:
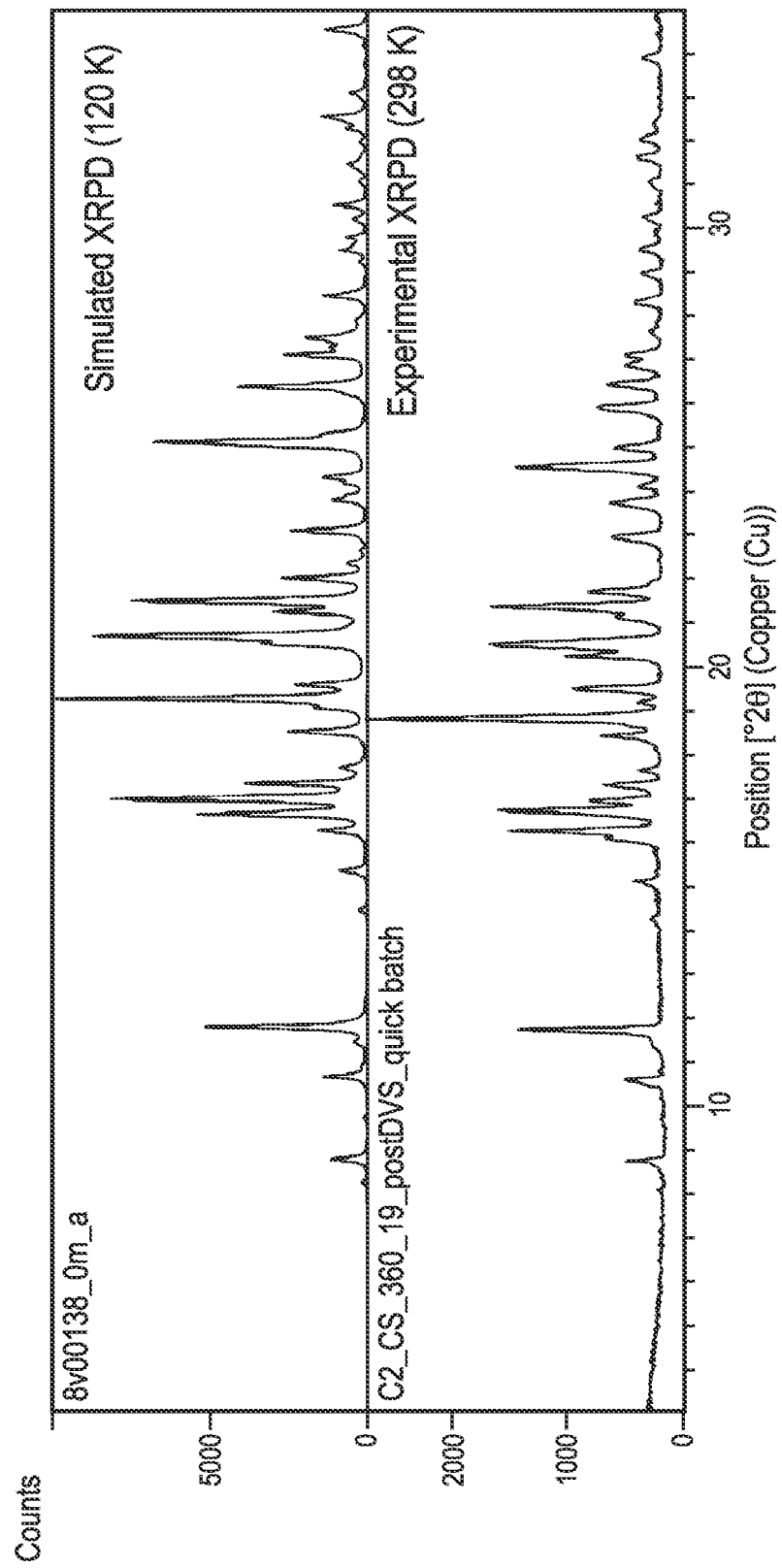
FIG. 11. displays the overlay of simulated (top) and experimental (bottom) XRPD diffraction patterns of crystalline Form 1 of ralinepag.
Figure 12A:
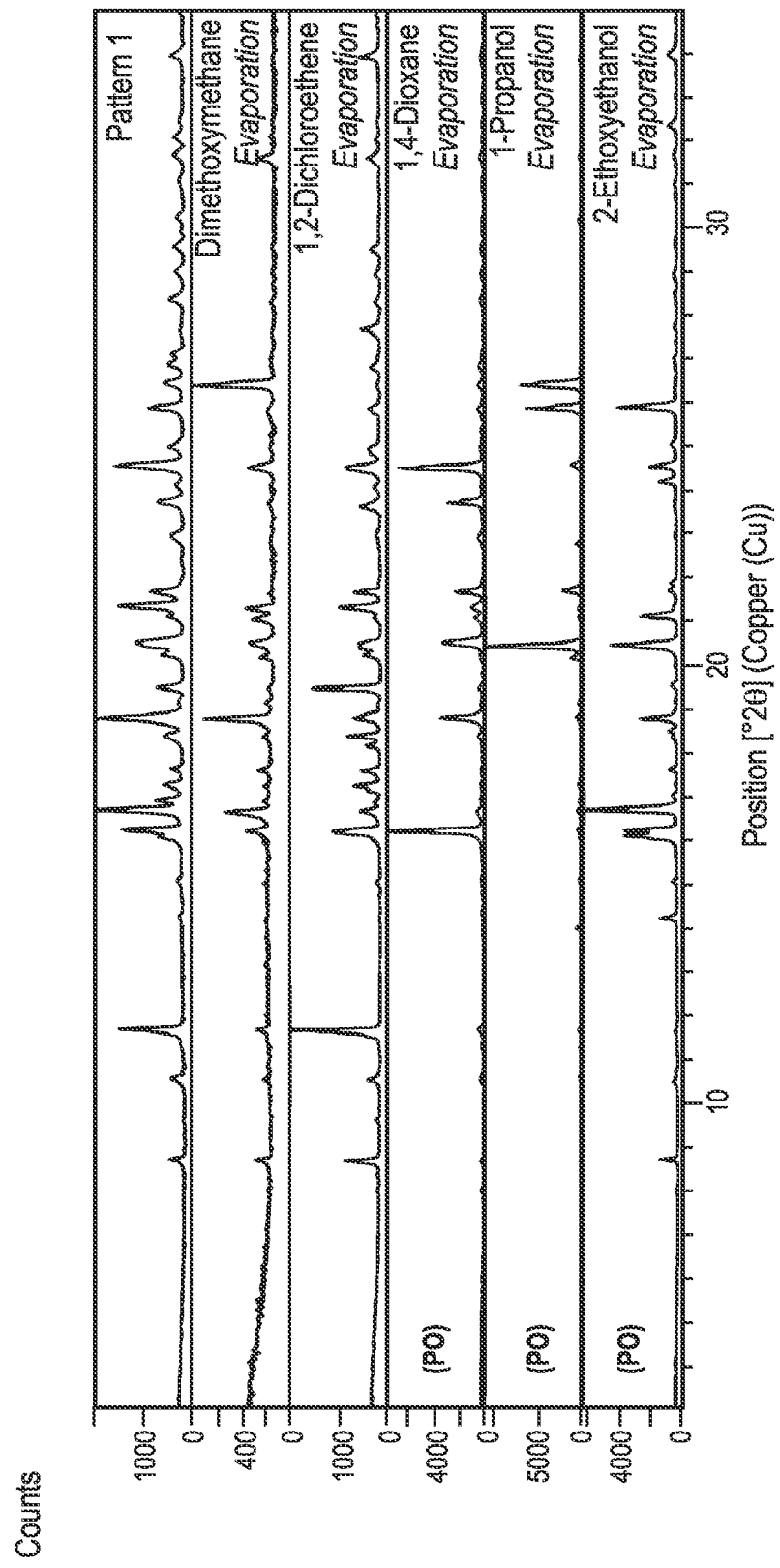
FIG. 12*a* to FIG. 12*f.* display X-Ray Powder Diffraction (XRPD) patterns of Crystalline Form 1 of ralinepag obtained from the solvent solubility study screen in Example 3. All figures display a reference X-Ray Powder Diffraction (XRPD) pattern of Form 1 at the top. XRPD patterns marked with a (PO) correspond to preferred orientations.
Figure 12B:
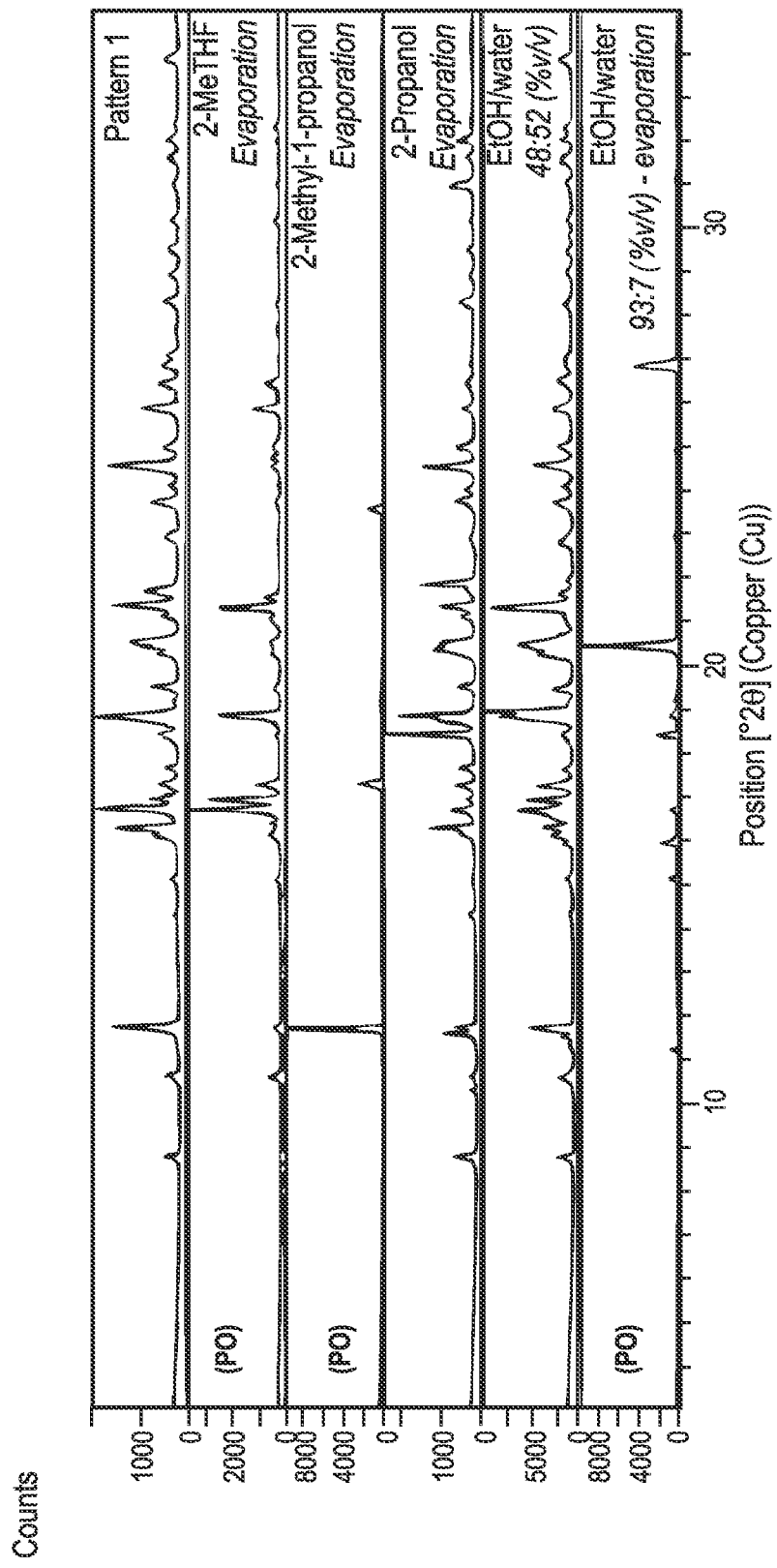
Figure 12C:
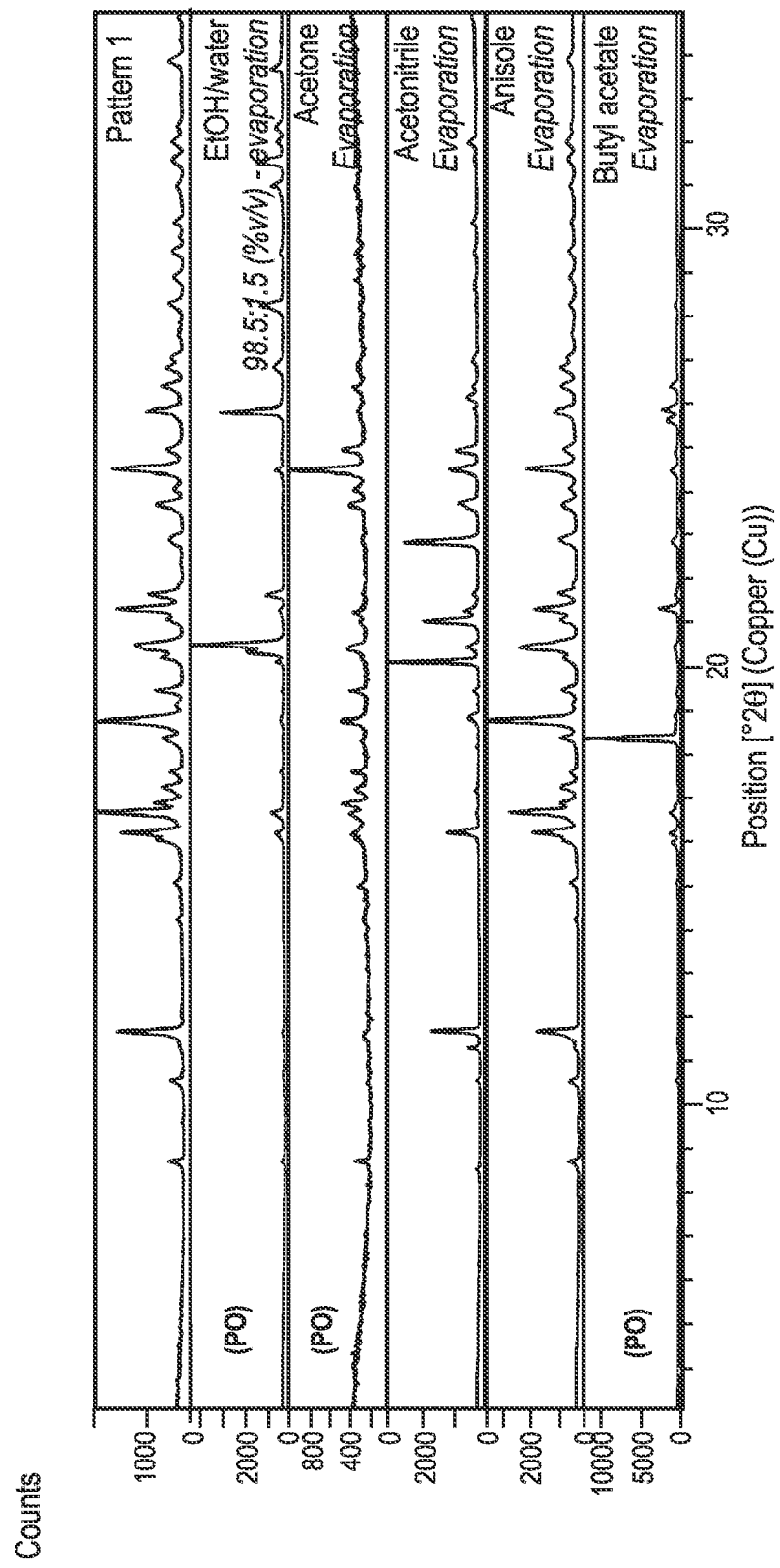
Figure 12D:
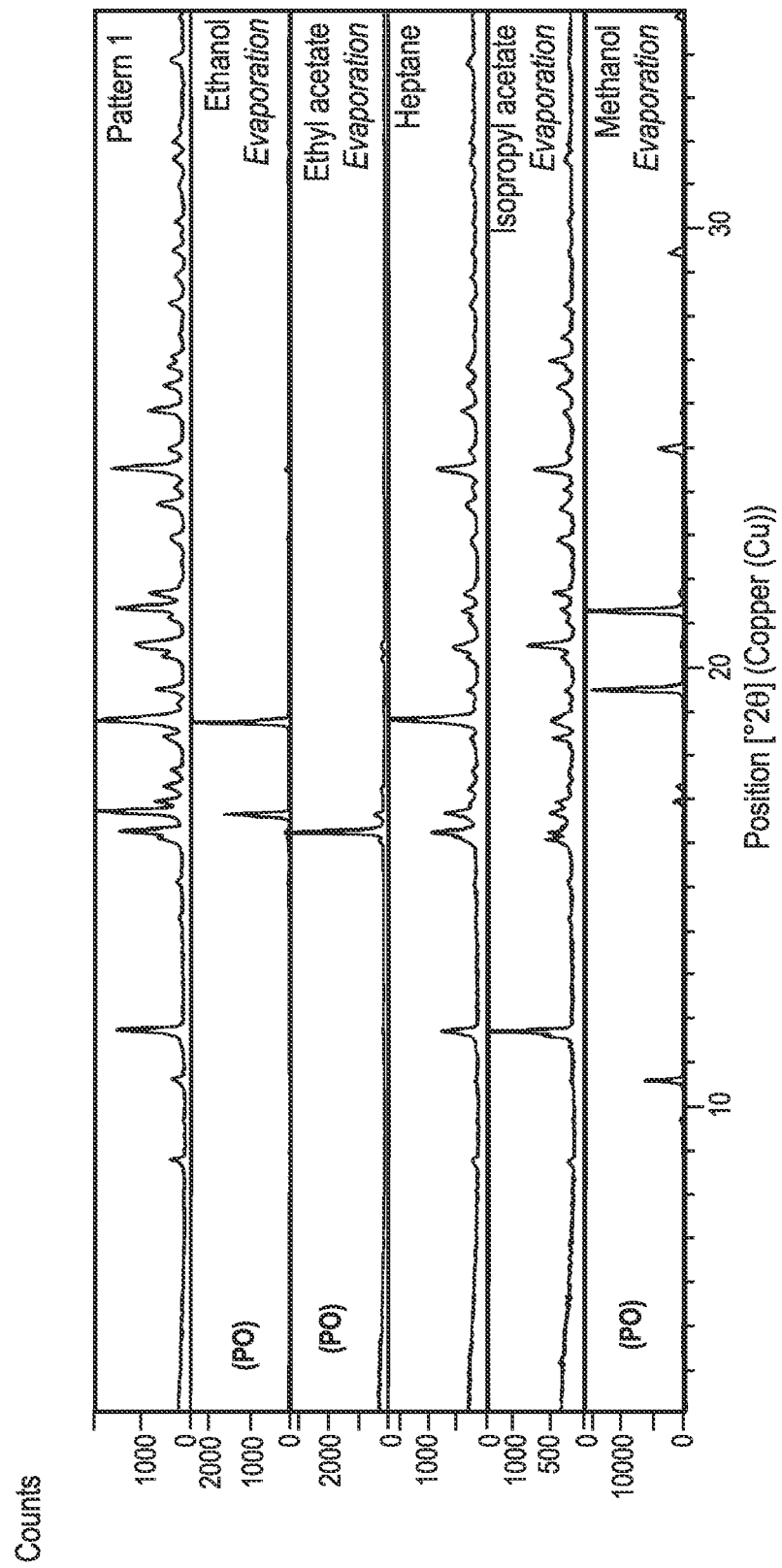
Figure 12E:
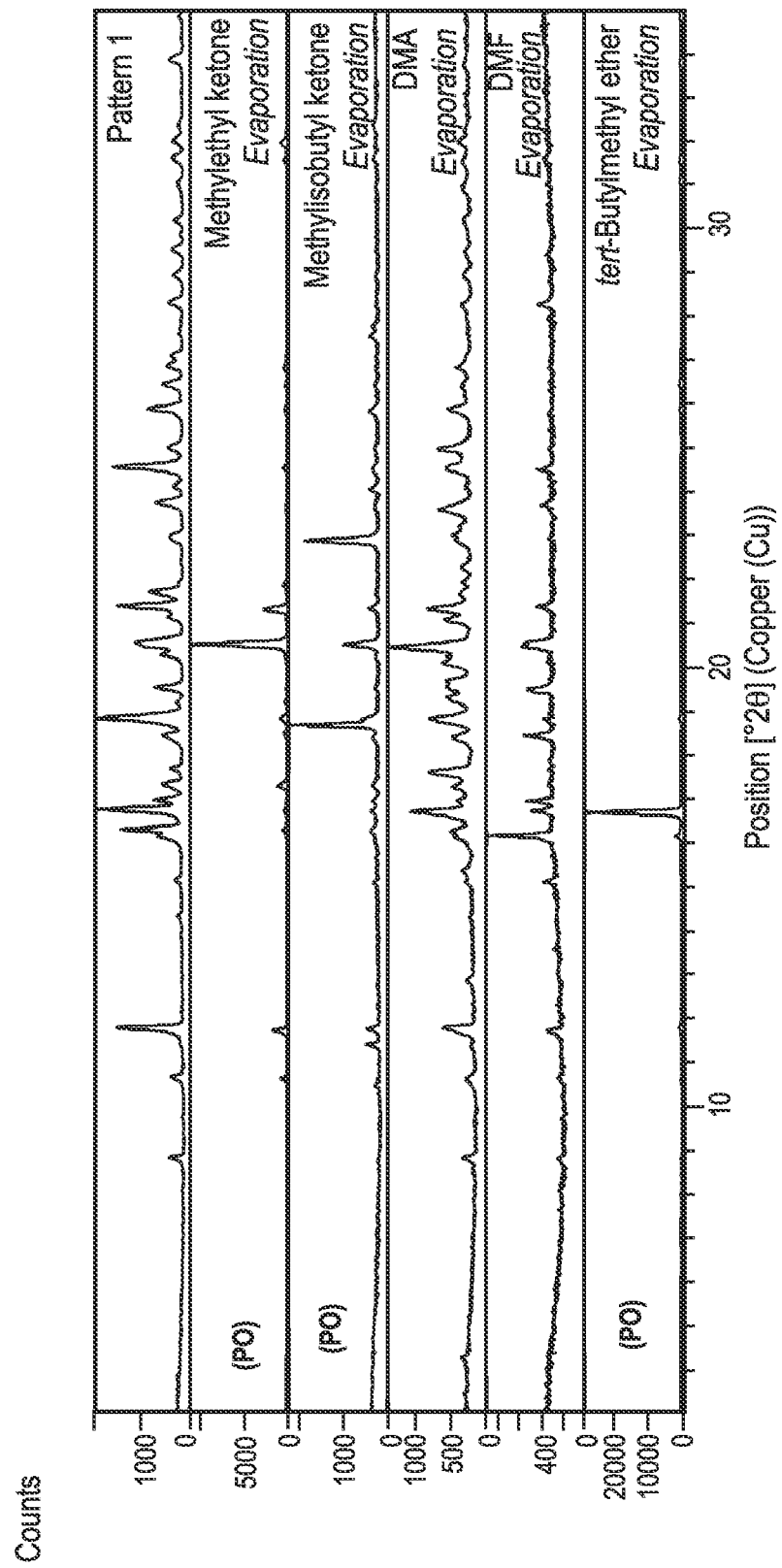
Figure 12F:
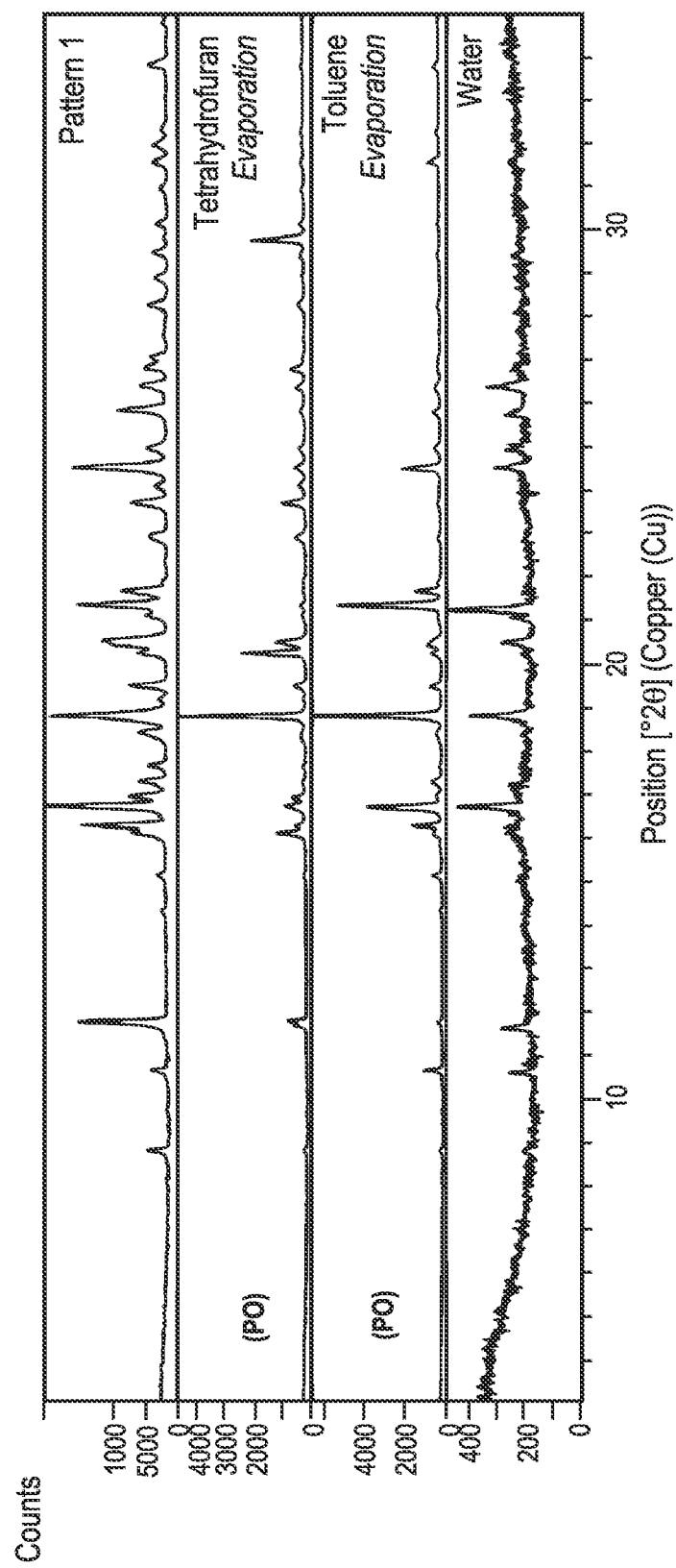
Figure 13A:
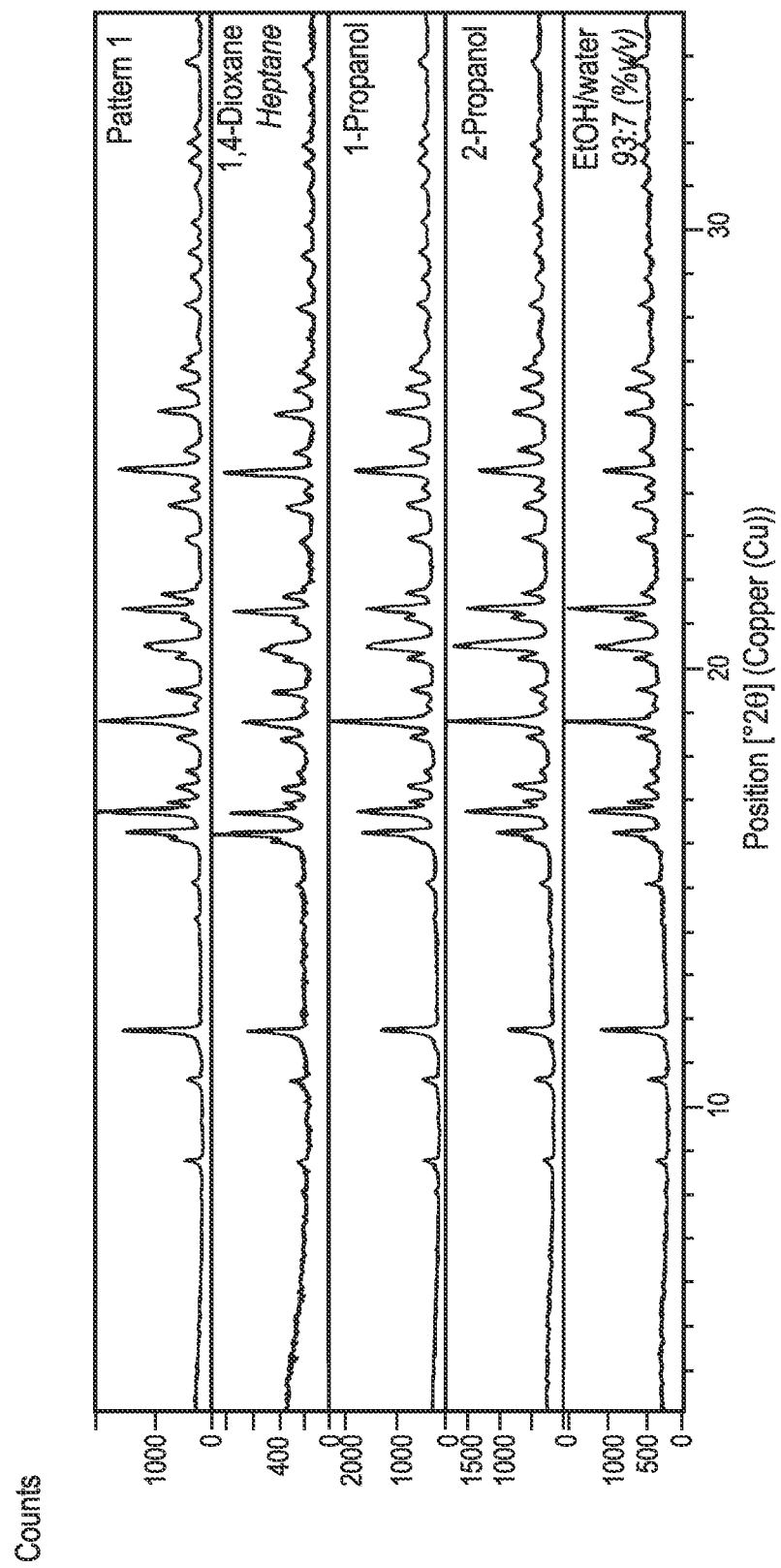
FIG. 13*a* to FIG. 13*e*. display X-Ray Powder Diffraction (XRPD) patterns of Crystalline Form 1 of ralinepag obtained from the post-thermal cycling experiments in Example 4. All figures display a reference XRPD pattern of Form 1 at the top. XRPD patterns marked with a (PO) correspond to preferred orientations.
Figure 13B:
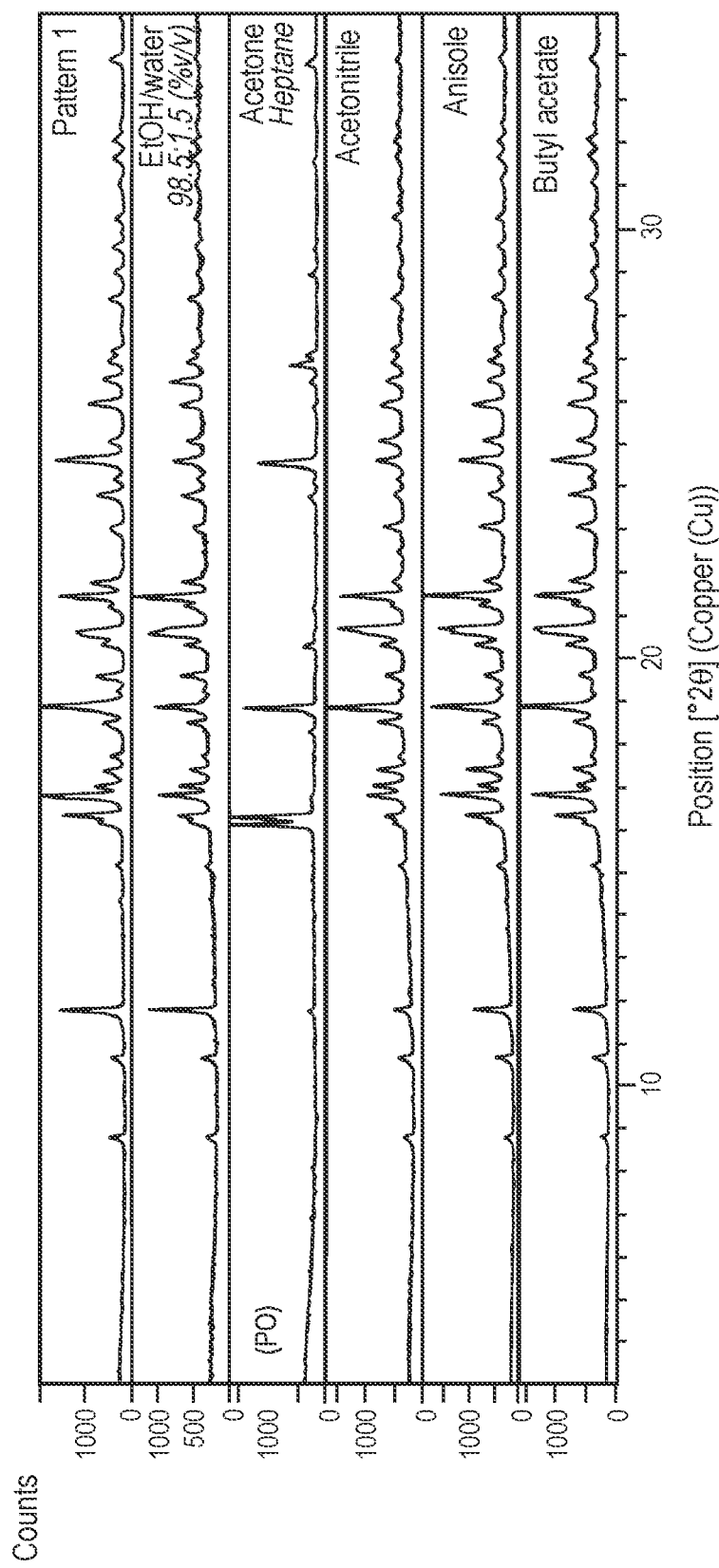
Figure 13C:
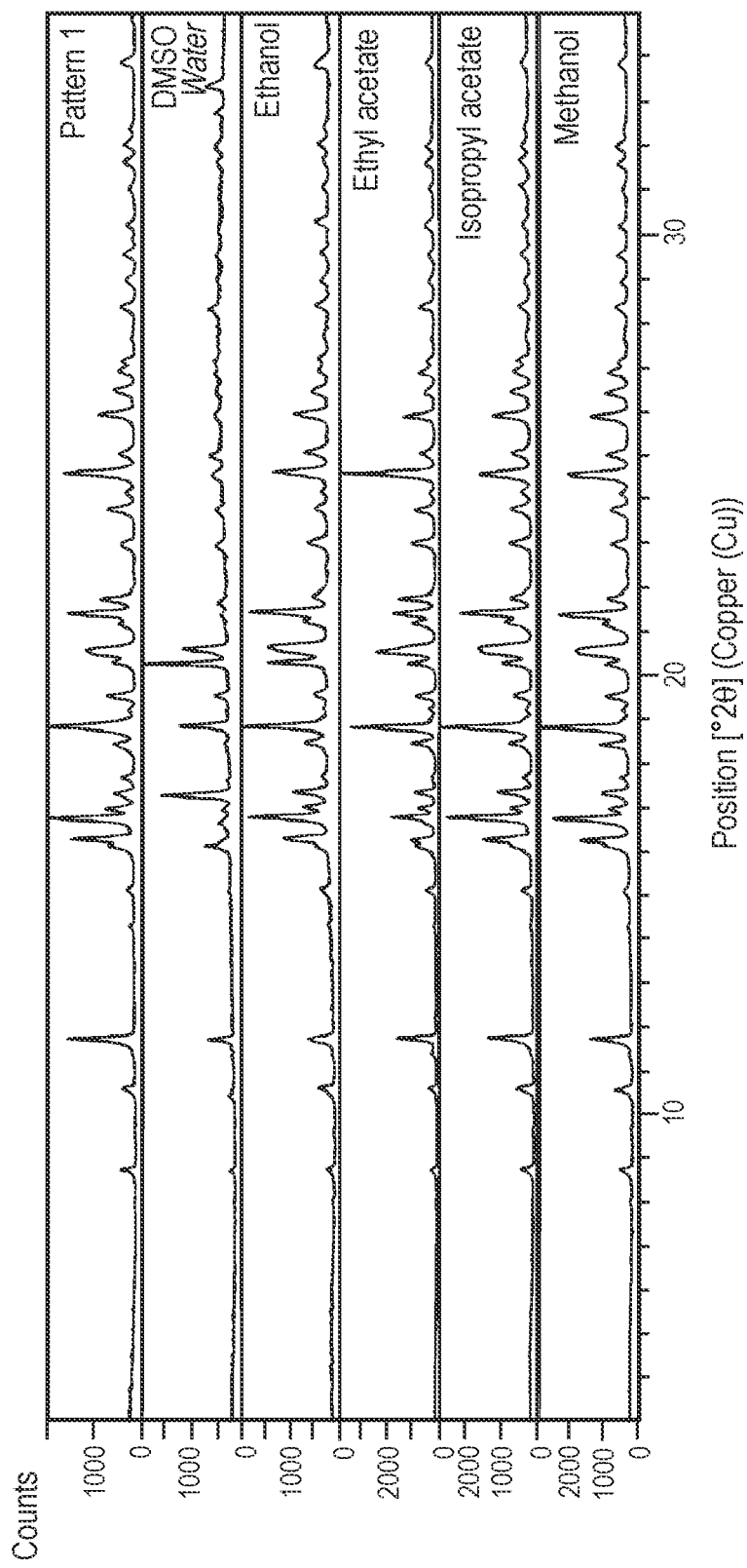
Figure 13D:
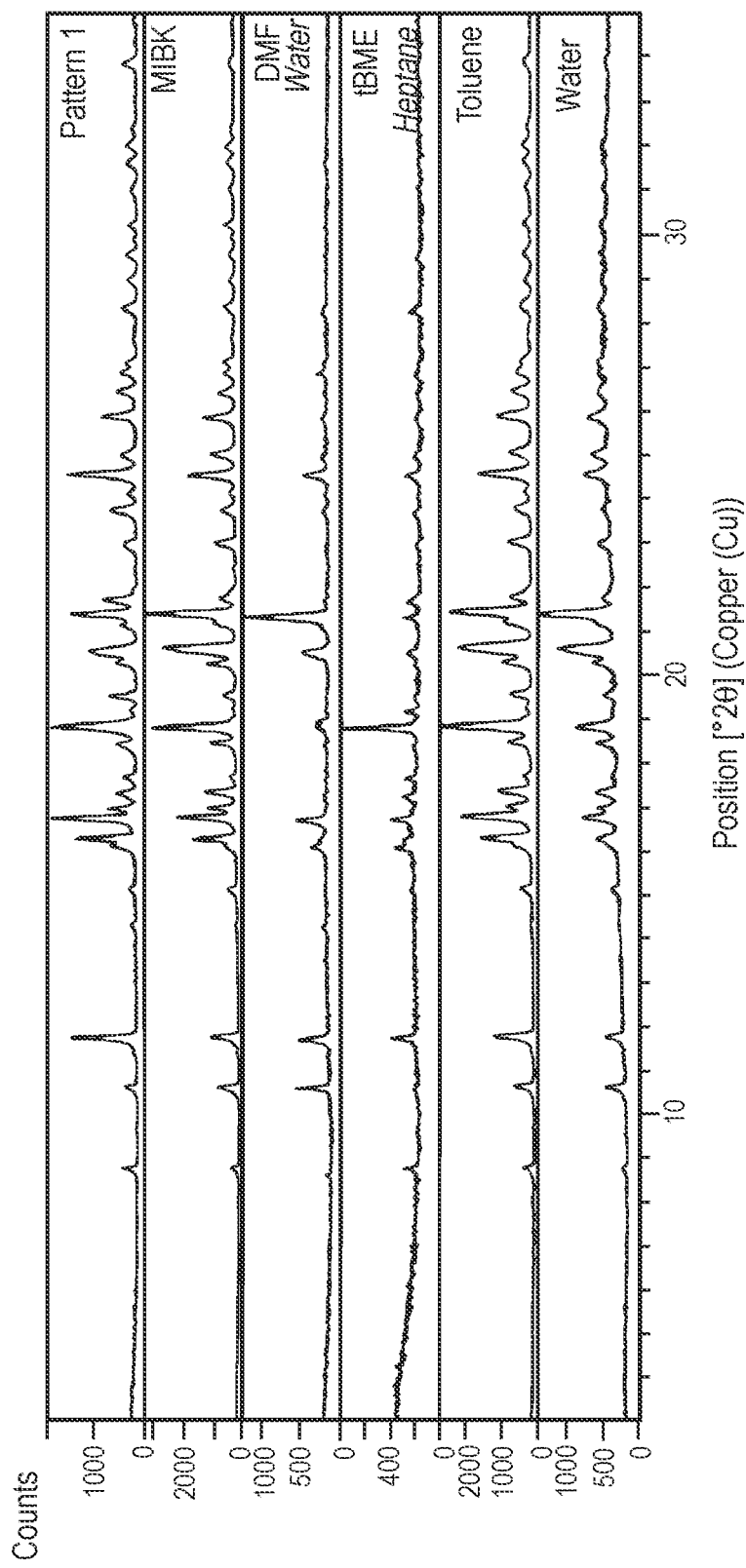
Figure 13E:
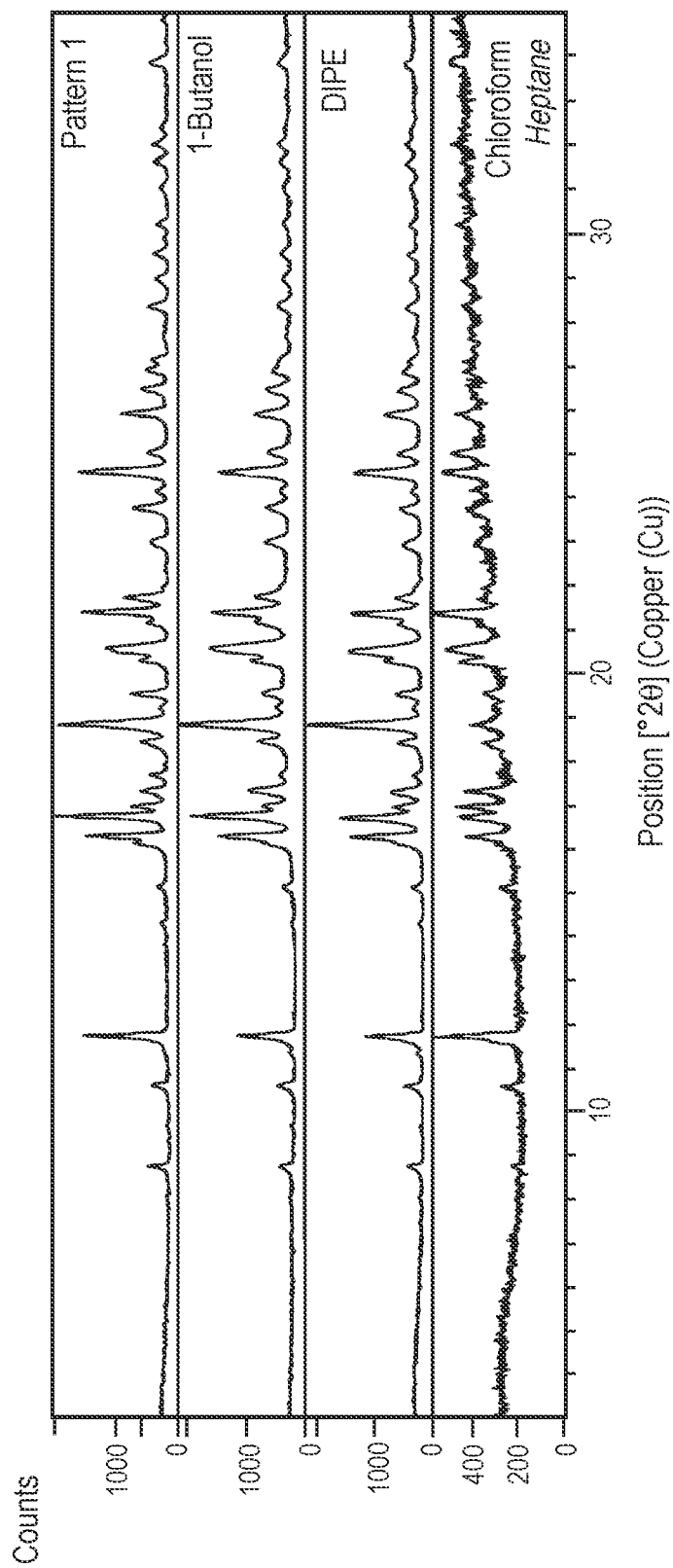

A simulated XRPD 2θ was calculated and compared with the experimental diffractogram of Crystalline Form 1 of ralinepag, excellent overlap was observed, as shown in FIG. 11. Any deviations in the diffractograms may be attributed to the temperature difference at which the sets of data were collected.

TABLE 5

Simulated XRPD 2θ diffractogram of ralinepag form 1 (20 most intense peaks).

| Pos. [°2θ] | d-spacing [Å] | Height [cts] | Rel. Int. [%] |
|---|---|---|---|
| 11.8 | 7.4743 | 5288.98 | 52.89 |
| 16.2 | 5.4388 | 1608.20 | 16.08 |
| 16.6 | 5.3137 | 5525.53 | 55.26 |
| 17.0 | 5.2107 | 8199.12 | 81.99 |
| 17.3 | 5.1055 | 3939.87 | 39.40 |
| 18.5 | 4.7814 | 2506.89 | 25.07 |
| 19.0 | 4.6498 | 1592.55 | 15.93 |
| 19.2 | 4.5993 | 9999.88 | 100.00 |
| 19.6 | 4.5255 | 2303.06 | 23.03 |
| 20.5 | 4.3254 | 3279.75 | 32.80 |
| 20.6 | 4.2882 | 8732.75 | 87.33 |
| 21.2 | 4.1758 | 2985.12 | 29.85 |
| 21.4 | 4.1298 | 7528.36 | 75.28 |
| 22.0 | 4.0336 | 2744.76 | 27.45 |
| 23.0 | 3.8483 | 2447.71 | 24.48 |
| 25.1 | 3.5424 | 6817.29 | 68.17 |
| 26.3 | 3.3783 | 4148.83 | 41.49 |
| 27.0 | 3.2886 | 2662.12 | 26.62 |
| 27.4 | 3.2427 | 1962.80 | 19.63 |
| 36.0 | 2.4913 | 2155.43 | 21.55 |

Example A-1: Oral Capsule (Immediate-Release Formulation)

To prepare a pharmaceutical composition for oral delivery, 0.01 to 0.4 mg of ralinepag form disclosed herein, or a pharmaceutically acceptable salt thereof, is dissolved in Kolliphor® RH4 or another suitable solubilizer, and is optionally thickened with silicon dioxide or another suitable thickener, and/or stabilized with butylated hydroxytoluene (BHT) or another suitable stabilizer. The liquid mixture is incorporated into an oral dosage unit such as a hard gelatin capsule, which is suitable for oral administration.

Example A-2: Oral Capsule (Extended-Release Formulation)

To prepare a pharmaceutical composition for extended release oral delivery, 0.01 to 0.4 mg of ralinepag, or a pharmaceutically acceptable salt thereof, is mixed with poloxamer P188 or another suitable solubilizer, and or glycerol monostearate or another suitable emulsifier. The liquid mixture is incorporated into an oral dosage unit such as a hard gelatin capsule, which is suitable for oral administration. The ratio of excipients can be varied to control the drug release rate.

Example A-3: Oral Tablet (Extended-Release Formulation)

A tablet is prepared by mixing 0.05-0.4 mg of ralinepag, or a pharmaceutically acceptable salt thereof, with 20-50% by weight of microcrystalline cellulose, 40-60% by weight of release modifying excipient such as a blend of hydroxypropyl methylcellulose (HPMC) K4M and HPMC K100LV, and 20-40% by weight of mannitol, silicon dioxide, magnesium stearate, or other appropriate excipients. Tablets are prepared by direct compression. The total weight of the compressed tablets is maintained at 100-200 mg.

The examples and embodiments described herein are for illustrative purposes only and various modifications or changes suggested to persons skilled in the art are to be included within the spirit and purview of this application and scope of the appended claims.

What is claimed is:

1. A crystalline form of ralinepag that is characterized as having:
   an XRPD pattern with peaks at 4.1±0.2°2-Theta, 15.5±0.2°2-Theta, and 16.9±0.2°2-Theta as measured using Cu Kα.radiation; and
   a TGA/DTA thermogram showing weak endothermic and exothermic events from 81 to 89° C. and a broad endothermic event having an onset at about 124.7° C.

2. The crystalline form of ralinepag of claim 1, wherein the crystalline form of ralinepag is characterized as having:
   an XRPD pattern substantially the same as shown in FIG. 2 as measured using Cu Kα.radiation; and
   a Thermogravimetric/Differential Thermal Analysis (TGA/DTA) thermogram substantially the same as shown in FIG. 8.

3. A crystalline form of ralinepag that is characterized as having:
   an XRPD pattern with peaks at 3.6±0.2°2-Theta, 18.7±0.2°2-Theta, and 22.2±0.2°2-Theta as measured using Cu Kα.radiation; and
   a Thermogravimetric Analysis (TGA) trace showing mass loss of about 17.8% from the onset of heating up to approximately 238° C. and a Differential Thermal Analysis (DTA) thermogram showing a sharp endothermic event having an onset at about 74.6° C.

4. The crystalline form of ralinepag of claim 3 wherein the crystalline form of ralinepag is characterized as having:
   an XRPD pattern substantially the same as shown in FIG. 3 as measured using Cu Kα.radiation; and
   a Thermogravimetric/Differential Thermal Analysis (TGA/DTA) thermogram substantially the same as shown in FIG. 9.

5. A crystalline form of ralinepag that is characterized as having:
   an XRPD pattern with peaks at 15.0±0.2°2-Theta, 16.7±0.2°2-Theta, and 18.0±0.2°2-Theta as measured using Cu Kα radiation; and
   a Differential Thermal Analysis (DTA) thermogram showing a broad endothermic event having an onset at about 29.0° C., a sharp endothermic event having an onset at about 127.8° C., or both.

6. The crystalline form of ralinepag of claim 5, wherein the crystalline form of ralinepag is characterized as having:
   an XRPD pattern substantially the same as shown in FIG. 4 as measured using Cu Kα.radiation; and
   a Thermogravimetric/Differential Thermal Analysis (TGA/DTA) thermogram substantially the same as shown in FIG. 10.

7. A solid form pharmaceutical composition comprising the crystalline ralinepag of claim 1 and at least one pharmaceutically acceptable excipient, wherein the pharmaceutical composition is suitable for administration by oral administration, intranasal administration, or inhalation; or the pharmaceutical composition is in the form of a tablet, a pill, or a capsule; or the pharmaceutical composition is suitable for administration with a dry powdered inhaler (DPI) or a metered dose inhaler (MDI).

8. The pharmaceutical composition of claim 7, wherein the pharmaceutical composition is a tablet, a pill, or a capsule.

9. The pharmaceutical composition of claim 7, wherein the pharmaceutical composition is suitable for administration with a dry powdered inhaler (DPI) or a metered dose inhaler (MDI).

10. A method of treating pulmonary arterial hypertension (PAH) in a subject in need thereof, comprising administering the crystalline form of ralinepag of claim 1, wherein the subject has World Health Organization (WHO)/New York Heart Association (NYHA) functional class II to IV symptoms.

11. A solid form pharmaceutical composition comprising the crystalline ralinepag of claim 3 and at least one pharmaceutically acceptable excipient, wherein the pharmaceutical composition is suitable for administration by oral administration, intranasal administration, or inhalation; or the pharmaceutical composition is in the form of a tablet, a pill, or a capsule; or the pharmaceutical composition is suitable for administration with a dry powdered inhaler (DPI) or a metered dose inhaler (MDI).

12. The pharmaceutical composition of claim 11, wherein the pharmaceutical composition is a tablet, a pill, or a capsule.

13. The pharmaceutical composition of claim 11, wherein the pharmaceutical composition is suitable for administration with a dry powdered inhaler (DPI) or a metered dose inhaler (MDI).

14. A method of treating pulmonary arterial hypertension (PAH) in a subject in need thereof, comprising administering the crystalline form of ralinepag of claim 3, wherein the subject has World Health Organization (WHO)/New York Heart Association (NYHA) functional class II to IV symptoms.

15. A solid form pharmaceutical composition comprising the crystalline ralinepag of claim 5 and atleast one pharmaceutically acceptable excipient, wherein the pharmaceutical composition is suitable for administration by oral administration, intranasal administration, or inhalation; or the pharmaceutical composition is in the form of a tablet, a pill, or a capsule; or the pharmaceutical composition is suitable for administration with a dry powdered inhaler (DPI) or a metered dose inhaler (MDI).

16. The pharmaceutical composition of claim 15, wherein the pharmaceutical composition is a tablet, a pill, or a capsule.

17. The pharmaceutical composition of claim 15, wherein the pharmaceutical composition is suitable for administration with a dry powdered inhaler (DPI) or a metered dose inhaler (MDI).

18. A method of treating pulmonary arterial hypertension (PAH) in a subject in need thereof, comprising administering the crystalline form of ralinepag of claim 5, wherein the subject has World Health Organization (WHO)/New York Heart Association (NYHA) functional class II to IV symptoms.

* * * * *